US012213743B2

(12) United States Patent
Mahfouz

(10) Patent No.: US 12,213,743 B2
(45) Date of Patent: Feb. 4, 2025

(54) ULTRA-WIDEBAND POSITIONING FOR WIRELESS ULTRASOUND TRACKING AND COMMUNICATION

(71) Applicant: TechMah Medical LLC, Knoxville, TN (US)

(72) Inventor: Mohamed R. Mahfouz, Knoxville, TN (US)

(73) Assignee: TECHMAH MEDICAL LLC, Knoxville, TN (US)

(*) Notice: Subject to any disclaimer, the term of this patent is extended or adjusted under 35 U.S.C. 154(b) by 1162 days.

(21) Appl. No.: 17/022,176

(22) Filed: Sep. 16, 2020

(65) Prior Publication Data
US 2021/0015559 A1    Jan. 21, 2021

Related U.S. Application Data

(63) Continuation of application No. 16/128,215, filed on Sep. 11, 2018, which is a continuation of application
(Continued)

(51) Int. Cl.
*A61B 17/15*    (2006.01)
*A61B 8/00*    (2006.01)
(Continued)

(52) U.S. Cl.
CPC ............ *A61B 34/20* (2016.02); *A61B 8/4472* (2013.01); *A61B 8/56* (2013.01); *A61B 17/1703* (2013.01);
(Continued)

(58) Field of Classification Search
CPC ....... A61B 34/30; A61B 34/10; A61B 8/4472; A61B 8/56; A61B 17/1703;
(Continued)

(56) References Cited

U.S. PATENT DOCUMENTS 5,653,714 A    8/1997 Dietz et al.
5,749,876 A    5/1998 Duvillier et al.
(Continued)

FOREIGN PATENT DOCUMENTS

DE    202006010728    9/2006
EP    1634536    3/2006
(Continued)

OTHER PUBLICATIONS

Mahfouz et al., A Robust Method of Registration of Three-Dimensional Knee Implant Models to Two-Dimensional Fluoroscopy Images, IEEE Transactions on Medical Imaging, vol. 22, No. 12, Nov. 24, 2003, entire document.
(Continued)

*Primary Examiner* — Eduardo C Robert
*Assistant Examiner* — David C Comstock
(74) *Attorney, Agent, or Firm* — ALLEN, DYER, DOPPELT + GILCHRIST, P.A.

(57) ABSTRACT

A method of designing an orthopedic implant comprising: (a) iteratively evaluating possible shapes of a dynamic orthopedic implant using actual anatomical shape considerations and kinematic shape considerations; and, (b) selecting
(Continued)

a dynamic orthopedic implant shape from one of the possible shapes, where the dynamic orthopedic implant shape selected satisfies predetermined kinematic and anatomical constraints.

22 Claims, 58 Drawing Sheets

Related U.S. Application Data

No. 15/458,934, filed on Mar. 14, 2017, now abandoned.

(60) Provisional application No. 62/384,521, filed on Sep. 7, 2016, provisional application No. 62/308,176, filed on Mar. 14, 2016.

(51) Int. Cl.

| | | |
|---|---|---|
| *A61B 17/17* | (2006.01) | |
| *A61B 34/10* | (2016.01) | |
| *A61B 34/20* | (2016.01) | |
| *A61F 2/30* | (2006.01) | |
| *A61F 2/32* | (2006.01) | |
| *A61F 2/38* | (2006.01) | |
| *A61F 2/40* | (2006.01) | |
| *A61F 2/42* | (2006.01) | |
| *A61F 2/46* | (2006.01) | |
| A61B 17/00 | (2006.01) | |
| A61B 90/00 | (2016.01) | |
| A61B 90/50 | (2016.01) | |
| G06F 30/00 | (2020.01) | |
| G06T 7/62 | (2017.01) | |
| G06T 19/00 | (2011.01) | |

(52) U.S. Cl.
CPC .......... *A61B 34/10* (2016.02); *A61F 2/30942* (2013.01); *A61F 2/32* (2013.01); *A61F 2/38* (2013.01); *A61F 2/40* (2013.01); *A61F 2/4202* (2013.01); *A61F 2/4603* (2013.01); *A61B 2017/00221* (2013.01); *A61B 2034/105* (2016.02); *A61B 2034/108* (2016.02); *A61B 2034/2048* (2016.02); *A61B 2034/2063* (2016.02); *A61B 2090/365* (2016.02); *A61B 2090/366* (2016.02); *A61B 2090/368* (2016.02); *A61B 2090/371* (2016.02); *A61B 2090/376* (2016.02); *A61B 2090/378* (2016.02); *A61B 2090/502* (2016.02); *A61F 2002/30943* (2013.01); *A61F 2002/30948* (2013.01); *A61F 2002/30952* (2013.01); *G06F 30/00* (2020.01); *G06T 7/62* (2017.01); *G06T 19/006* (2013.01); *G06T 2207/10121* (2013.01); *G06T 2207/30008* (2013.01)

(58) Field of Classification Search
CPC ........ A61B 2034/105; A61B 2034/108; A61B 2034/2048; A61B 2034/2063; A61B 2090/365; A61B 2090/366; A61B 2090/368; A61B 2090/371; A61B 2090/376; A61B 2090/378; A61B 2090/502; A61B 2017/00221; A61F 2/30942; A61F 2/32; A61F 2/38; A61F 2/40; A61F 2/4202; A61F 2/4603; A61F 2002/30943; A61F 2002/30948; A61F 2002/30952; G06T 7/62; G06T 19/006; G06T 2207/10121; G06T 2207/30008; G06F 30/00

USPC .............. 606/53, 79, 82, 87, 96, 97; 73/1.38
See application file for complete search history.

(56) References Cited

U.S. PATENT DOCUMENTS

| | | |
|---|---|---|
| 6,174,314 B1 | 1/2001 | Waddell |
| 7,377,924 B2 | 5/2008 | Raistrick et al. |
| 7,641,660 B2 | 1/2010 | Lakin et al. |
| 8,486,079 B2 | 7/2013 | Heavener et al. |
| 2002/0087274 A1 | 7/2002 | Alexander et al. |
| 2002/0115934 A1 | 8/2002 | Tuke |
| 2002/0198531 A1 | 12/2002 | Millard et al. |
| 2004/0243148 A1* | 12/2004 | Wasielewski .......... A61B 5/062 977/932 |
| 2004/0260301 A1 | 12/2004 | Lionberger et al. |
| 2005/0119661 A1 | 6/2005 | Hodgson et al. |
| 2006/0122618 A1 | 6/2006 | Claypool et al. |
| 2006/0155291 A1 | 7/2006 | Farrar et al. |
| 2006/0293681 A1 | 12/2006 | Claypool et al. |
| 2007/0015995 A1 | 1/2007 | Lang et al. |
| 2007/0100462 A1 | 5/2007 | Lang et al. |
| 2007/0287911 A1* | 12/2007 | Haid ...................... A61B 90/36 606/130 |
| 2008/0140081 A1 | 6/2008 | Heavener et al. |
| 2009/0042167 A1 | 2/2009 | Van Der Zel |
| 2009/0163923 A1 | 6/2009 | Flett et al. |
| 2009/0264894 A1 | 10/2009 | Wasielewski |
| 2010/0076563 A1 | 3/2010 | Otto et al. |
| 2010/0256504 A1 | 10/2010 | Moreau-Gaudry et al. |
| 2011/0071802 A1 | 3/2011 | Bojarski et al. |
| 2011/0087465 A1 | 4/2011 | Mahfouz |
| 2011/0251694 A1 | 10/2011 | Wasielewski |
| 2011/0275957 A1 | 11/2011 | Bhandari |
| 2011/0276052 A1* | 11/2011 | Hasselman ............. A61B 17/15 606/87 |
| 2011/0304332 A1 | 12/2011 | Mahfouz |
| 2011/0320153 A1* | 12/2011 | Lightcap .............. G01C 21/166 702/94 |
| 2012/0157887 A1 | 6/2012 | Fanson et al. |
| 2012/0209394 A1 | 8/2012 | Bojarski et al. |
| 2012/0265496 A1 | 10/2012 | Mahfouz |
| 2013/0144396 A1 | 6/2013 | Wasielewski |
| 2013/0158557 A1 | 6/2013 | Komistek |
| 2013/0211531 A1 | 8/2013 | Steines et al. |
| 2013/0237811 A1 | 9/2013 | Mihailescu et al. |
| 2014/0228860 A1 | 8/2014 | Steines et al. |
| 2014/0244220 A1 | 8/2014 | McKinnon et al. |
| 2014/0247336 A1 | 9/2014 | Vilsmeier et al. |
| 2014/0330416 A1 | 11/2014 | Wasielewski |
| 2015/0313684 A1 | 11/2015 | Fanson et al. |
| 2015/0328004 A1 | 11/2015 | Mahfouz |
| 2016/0045317 A1 | 2/2016 | Lang et al. |
| 2016/0176242 A1 | 6/2016 | Nakamata |
| 2016/0296335 A1 | 10/2016 | Wasielewski |
| 2017/0156798 A1 | 6/2017 | Wasielewski |
| 2017/0258526 A1* | 9/2017 | Lang ................... H05K 999/99 |
| 2017/0367766 A1 | 12/2017 | Mahfouz |
| 2019/0038361 A1 | 2/2019 | Wasielewski |
| 2019/0167352 A1 | 6/2019 | Mahfouz |
| 2020/0214844 A1 | 7/2020 | Wasielewski |
| 2021/0015559 A1 | 1/2021 | Mahfouz |
| 2021/0022810 A1 | 1/2021 | Mahfouz |
| 2022/0168045 A1 | 6/2022 | Wasielewski |
| 2022/0273450 A1 | 9/2022 | Steines et al. |

FOREIGN PATENT DOCUMENTS

| | | |
|---|---|---|
| EP | 3429497 A1 | 1/2019 |
| EP | 3426179 | 3/2023 |
| EP | 4385446 | 6/2024 |
| JP | 2011515163 | 5/2011 |
| WO | 2010128409 | 11/2010 |
| WO | 2010151564 A1 | 12/2010 |
| WO | 2011028624 A1 | 3/2011 |
| WO | 2014145267 A1 | 9/2014 |
| WO | 2014176207 | 10/2014 |

(56) References Cited

FOREIGN PATENT DOCUMENTS

| WO | 2015089118 A1 | 6/2015 |
| WO | 2015192117 | 12/2015 |
| WO | 2016007936 | 1/2016 |
| WO | 2014200016 | 2/2017 |
| WO | 2017160889 A1 | 9/2017 |

OTHER PUBLICATIONS

W. Hu and S.-C. Zhu, "Learning 3D Object Templates by Quantizing Geometry and Appearance Spaces," in IEEE Transactions on Pattern Analysis and Machine Intelligence, vol. 37, No. 6, pp. 1190-1205, Jun. 1, 2015, doi: 10.1109/TPAMI.2014.2362141.
Deangelis et al., "Indoor positioning by ultrawide band radio aided inertial navigation", Metrology and Measurement Systems, PAN Journals, vol. 18, No. 3, 2010, pp. 447-460.

\* cited by examiner

Table 1 Evaluation Score Function

Algorithm Evaluate score

Input: shape parameters θ, fluoro image
Output: score
1: initialize score=0;
2: render the reconstructed surface model (θ) on 2D;
3: for i=1:9
4:   calculate edge score (e) of the ith fluoro image;
5:   calculate region score (r) of the ith fluoro image;
6:   score = score + 0.82*e+ 0.12*r;
7: end for (A)

(B)

ULTRA-WIDEBAND POSITIONING FOR WIRELESS ULTRASOUND TRACKING AND COMMUNICATION

CROSS REFERENCE TO RELATED APPLICATIONS

The present application is a continuation of U.S. application Ser. No. 16/128,215, filed Sep. 11, 2018, which is a continuation of U.S. application Ser. No. 15/458,934, filed Mar. 14, 2017, which claims the benefit of U.S. Provisional Patent Application Ser. No. 62/308,176, titled "Ultra-wideband positioning for wireless ultrasound tracking and communication," filed Mar. 14, 2016, and U.S. Provisional Patent Application Ser. No. 62/384,521, titled "Ultra-wideband positioning for wireless ultrasound tracking and communication," filed Sep. 7, 2016, the disclosure of each of which is incorporated herein by reference.

INTRODUCTION TO THE INVENTION

The present disclosure is directed to dynamic orthopedic implants, methods of creating the same, methods of manufacturing the same, and mounting the dynamic implants as part of a surgical procedure, as well as tracking devices used to track surgical instruments, implants, patient anatomy, and a surgeon as part of carrying out a surgical plan that may include displaying an augmented reality scene over real-world images of a patient, surgical tools, and implants as part of surgical navigation.

It is a first aspect of the present invention to provide a method of designing an orthopedic implant comprising: (a) iteratively evaluating possible shapes of a dynamic orthopedic implant using actual anatomical shape considerations and kinematic shape considerations; and, (b) selecting a dynamic orthopedic implant shape from one of the possible shapes, where the dynamic orthopedic implant shape selected satisfies predetermined kinematic and anatomical constraints.

In a more detailed embodiment of the first aspect, the orthopedic implant comprises at least one of a tibial implant and a femoral implant. In yet another more detailed embodiment, the method further includes gathering dynamic imaging data prior to iteratively evaluating possible shapes of a dynamic orthopedic implant. In a further detailed embodiment, the dynamic imaging data is fluoroscopic data. In still a further detailed embodiment, the dynamic imaging data is subjected to an image correction process to reduce distortion. In a more detailed embodiment, the dynamic imaging data is subjected to a feature extraction process to establish an edge of a bone. In a more detailed embodiment, the dynamic imaging data is subjected to an initialization process to estimate a pose of a bone. In another more detailed embodiment, the dynamic imaging data is subjected to a sequential shape and pose estimation process to generate a three dimensional virtual model of a bone. In yet another more detailed embodiment, the sequential shape and pose estimation process utilizes inputs from a statistical shape model creation process. In still another more detailed embodiment, the dynamic imaging data is segmented and classified as part of the shape and pose estimation process.

In yet another more detailed embodiment of the first aspect, the dynamic imaging data is utilized to generate multiple bone models that change position with respect to one another across a range of motion. In yet another more detailed embodiment, the method further includes constructing virtual anatomical models using the dynamic imaging data. In a further detailed embodiment, the virtual anatomical models comprise an anatomical joint comprising at least two bones. In still a further detailed embodiment, the anatomical joint includes at least one of a shoulder joint, a knee joint, a hip joint, and an ankle joint. In a more detailed embodiment, the anatomical models include soft tissue. In a more detailed embodiment, the soft tissue includes a ligament. In another more detailed embodiment, the predetermined kinematic constraint is derived from predicting normal kinematics. In yet another more detailed embodiment, normal kinematics is extracted from a kinematic database. In still another more detailed embodiment, the method further includes establishing implant geometry constraints for the orthopedic implant.

In a more detailed embodiment of the first aspect, the method further includes establishing manufacturing constraints for the orthopedic implant. In yet another more detailed embodiment, the method further includes establishing a surgical plan to effectuate implantation of the orthopedic implant. In a further detailed embodiment, the surgical plan includes instructions for a surgical navigation system to guide in making a predetermined bone cut. In still a further detailed embodiment, the instructions include orientation information indicating the orientation the predetermined bone cut with respect to a patient bone. In a more detailed embodiment, the instructions include position information indicating the position the predetermined bone cut with respect to a patient bone. In a more detailed embodiment, the instructions include attachment of a position tracker to a patient bone. In another more detailed embodiment, the instructions include attachment of a position tracker to a patient. In yet another more detailed embodiment, the surgical plan includes instructions for the surgical navigation system to guide in making a series of predetermined bone cuts.

It is a second aspect of the present invention to provide a patient-specific orthopedic implant comprising a bearing surface optimized for an anatomical shape of the patient, the bearing surface having been virtually generated and evaluated kinematically prior to fabrication.

In a more detailed embodiment of the second aspect, the orthopedic implant comprises at least one of a tibial implant and a femoral implant. In yet another more detailed embodiment, the anatomical shape of the patient was gathered using dynamic imaging data generated responsive to movement of the patient. In a further detailed embodiment, the dynamic imaging data is fluoroscopic data. In still a further detailed embodiment, the dynamic imaging data is subjected to an image correction process to reduce distortion. In a more detailed embodiment, the dynamic imaging data is subjected to a feature extraction process to establish an edge of a bone. In a more detailed embodiment, the dynamic imaging data is subjected to an initialization process to estimate a pose of a bone. In another more detailed embodiment, the dynamic imaging data is subjected to a sequential shape and pose estimation process to generate a three dimensional virtual model of a bone. In yet another more detailed embodiment, the sequential shape and pose estimation process utilizes inputs from a statistical shape model creation process. In still another more detailed embodiment, the dynamic imaging data is segmented and classified as part of the shape and pose estimation process.

In yet another more detailed embodiment of the second aspect, the dynamic imaging data is utilized to generate multiple bone models that change position with respect to one another across a range of motion. In yet another more detailed embodiment, the implant further includes constructing virtual anatomical models using the dynamic imaging data. In a further detailed embodiment, the virtual anatomical models comprise an anatomical joint comprising at least two bones. In still a further detailed embodiment, the anatomical joint includes at least one of a shoulder joint, a knee joint, a hip joint, and an ankle joint. In a more detailed embodiment, the anatomical models include soft tissue. In a more detailed embodiment, the soft tissue includes a ligament.

It is a third aspect of the present invention to provide a surgical navigation system comprising: (a) a first ultrawide band and inertial measurement unit; (b) a second ultrawide band and inertial measurement unit; (c) a processor communicatively coupled to the first and second ultrawide band and inertial measurement units; and, (d) a graphical display communicatively coupled to the processor, the graphical display configured to display augmented reality images that are capable of changing in at least one of position and orientation as the graphical display is repositioned with respect to at least one of the first and second ultrawide band and inertial measurement units.

In a more detailed embodiment of the third aspect, the second ultrawide band and inertial measurement unit, the processor, and the graphical display are integrated as part of a user wearable helmet. In yet another more detailed embodiment, the helmet includes a visor upon which the graphical display projects the augmented reality images. In a further detailed embodiment, the system further includes a camera. In still a further detailed embodiment, augmented reality images are generated by a projector. In a more detailed embodiment, the projector comprises a laser projector.

It is a fourth aspect of the present invention to provide a method of planning a surgical procedure, the method comprising: (a) generating instructions allowing for generation of a dynamic orthopedic implant, where the dynamic orthopedic implant is generated as a result of iteratively evaluating possible surface bearing shapes using actual anatomical shape considerations and kinematic shape considerations; (b) generating instructions for generation of at least one of a tangible guide and a virtual guide, where the instructions are patient-specific; and, (c) generating navigation instructions to be facilitate implantation of the dynamic orthopedic implant, where the navigation instruction include concurrently tracking at least a portion of a patient and a surgical tool using a combination ultrawide band and inertial measurement unit

DETAILED DESCRIPTION

The exemplary embodiments of the present disclosure are described and illustrated below to encompass dynamic orthopedic implants, methods of creating the same, methods of manufacturing the same, and mounting the dynamic implants as part of a surgical procedure, as well as tracking devices used to track surgical instruments, implants, patient anatomy, and a surgeon as part of carrying out a surgical plan that may include displaying an augmented reality scene over real-world images of a patient, surgical tools, and implants as part of surgical navigation. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Ultra-Wideband Positioning for Wireless Ultrasound Tracking and Communication

Currently, wireless ultrasound probe can communicate ultrasound information and provide real-time position and orientation information as part of a single unit/package. Disclosed herein is a system that allows for a wireless ultrasound probe with integrated communication and incorporating ultrawide band (UWB) technology. An exemplary wireless ultrasound probe comprising part of the exemplary system includes a first UWB unit for ultrasound wireless data streaming and a second UWB unit for real-time position tracking and wireless control/feedback. The wireless ultrasound probe also integrates the two UWB units with an IMU and microcontroller (MCU) for processing position, orientation, and ultrasound data.

Ultrasound Probe Design

Figure 1:
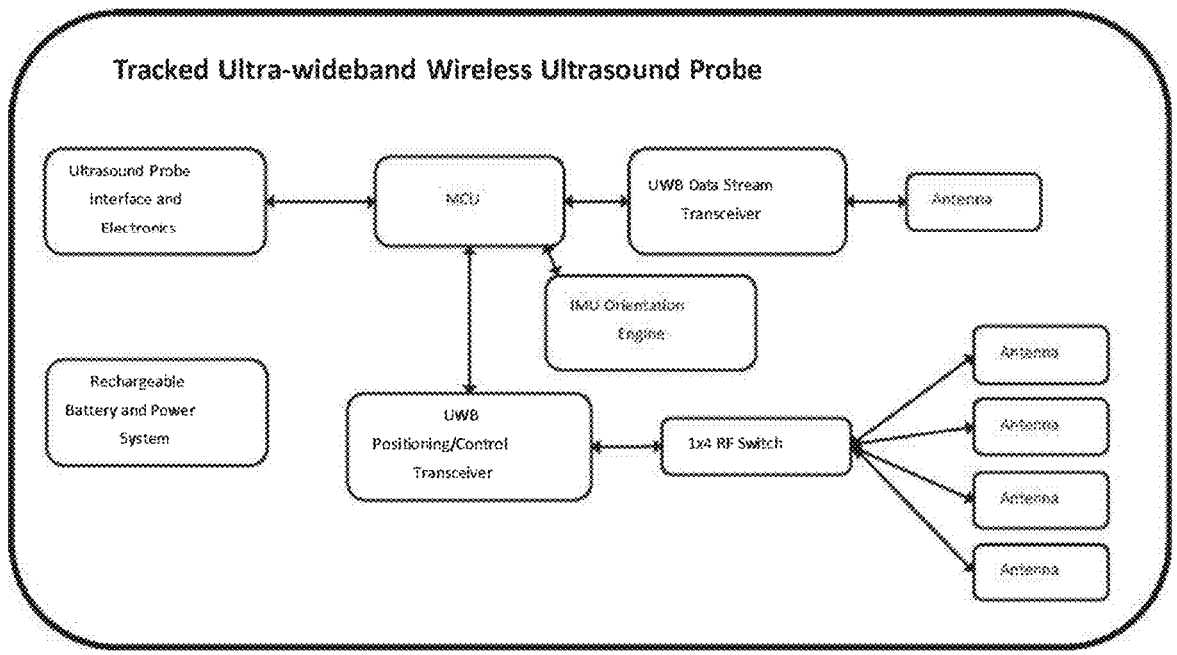
FIG. 1 is a block diagram of the components in an example tracked UWB enabled ultrasound probe in accordance with the instant disclosure.

In accordance with the instant disclosure, an exemplary wireless ultrasound probe 100 may include any number of (one or a plurality) ultrasound transducers. By way of further example, the wireless ultrasound probe may integrated one or more UWB transceiver units, containing one or more antennas for positioning/control and real-time data streaming, as well as one or more inertial measurement units (IMUs) that include one or more accelerometers, gyroscopes, and magnetometers. FIG. 1 comprises an exemplary block diagram depicting exemplary components of an exemplary wireless, UWB enabled ultrasound probe.

Figure 3:
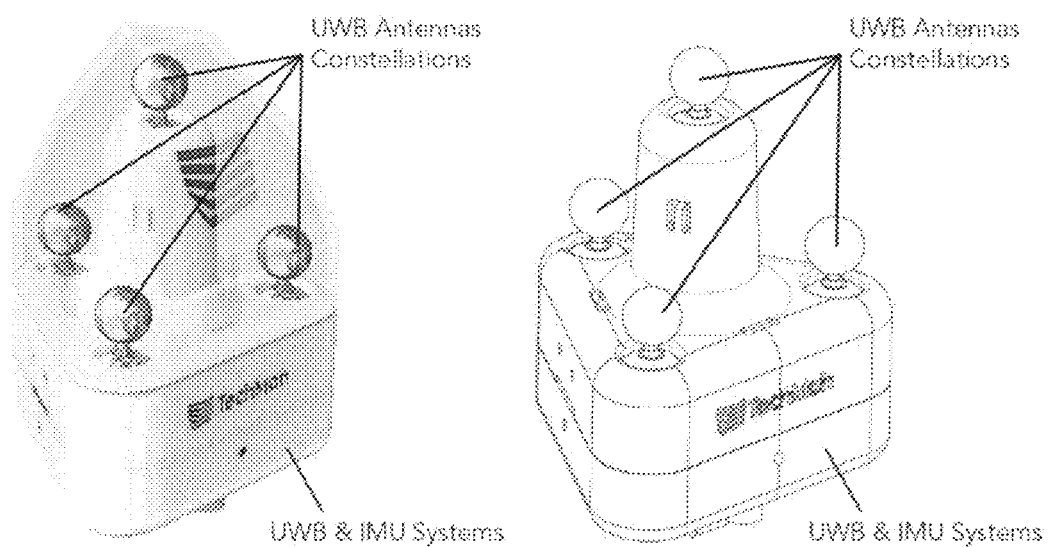
FIG. 3 is a pair of diagrams depicting exemplary designs for UWB and IMU hybrid tracking system in accordance with the instant disclosure.

By way of further example, as depicted in FIG. 3, an exemplary UWB unit (or UWB & IMU Systems) 300 may contain four or more antennas (or UWB Antennas Constellations) 301 (such as in a tetrahedral layout). By having at least four antennas that are not all coplanar with one another, the antennas operate to be capable of resolving three dimensional orientation changes given that any three antennas form a unique plane and perpendicular axis in three dimensional (3D) space. The antennas may be connected to an UWB transceiver using a 1×N radio frequency (RF) switch, where "N" is any integer. By way of further example, the UWB unit may include a MCU operative to control activation and deactivation of the RF switch, as well channel switching of the RF switch. In this fashion, each antenna generates signals that allow for derivation of position and orientation information associated with each of the antenna. In exemplary form, determining the position of each of the four antennas occurs from determining the time it takes for signals to be sent from a central UWB anchor unit and received by each of the four antennas. In other words, determining the position of each UWB tracking unit is performed between each tag within the UWB tracking unit and the central UWB anchor unit, which may be connected to a central processing unit (CPU) for processing and generation of visual display instructions.

UWB Positioning

An exemplary UWB tracking unit in accordance with the instant disclosure may connect multiple antennas to a single transceiver, which allows ranging, positioning, and tracking multiple UWB antennas (targets) utilizing the same UWB transceiver unit. By way of example, the antennas within the UWB tracking unit may serve a master role/unit or a peripheral role/unit, where the master role serves to generate a timing reference for the peripherals antenna within the system. The antennas within each UWB tracking unit may be arranged in any configuration with the condition that there are four or more antennas and that one of these antennas does not reside on the same plane with the other three antennas. For example, as mentioned previously, a tetrahedron antenna configuration satisfies the foregoing condition. Regardless of the antenna configuration, the four antennas may connect to a single UWB transceiver, where each antenna serves as a reference point for positioning. With single timing circuitry, and a single transceiver to feed the UWB pulses into multiple antennas, this configuration enables clock synchronization among all reference points in the UWB tracking unit. This configuration may tremendously improve the flexibility of the installation of the master unit, as well as easing the calibration procedure. In short range localization applications, a single master unit may be sufficient to provide adequate positioning data for localization. In large area localization applications, multiple master units may be used. By way of example, the timing circuitry of the master units may be synchronized during operation with either wired or wireless methods.

The foregoing exemplary tetrahedral design may allow for determination of the position and orientation of each UWB unit. The addition of the IMU can be used to accurately determine orientation. Both sensor system outputs are fused, so that errors from the UWB and the IMU are reduced through fusion and filtering techniques. One example of a method would be use of a recursive Bayesian estimation filter to compliment the orientation estimation between the UWB and IMU system. The IMU system may be inaccurate and subject to magnetic artifact, where the UWB system can be used to provide correction. In addition, the tetrahedral design of the UWB unit may allow monitoring and improved translation estimations among the antennas.

Figure 2:
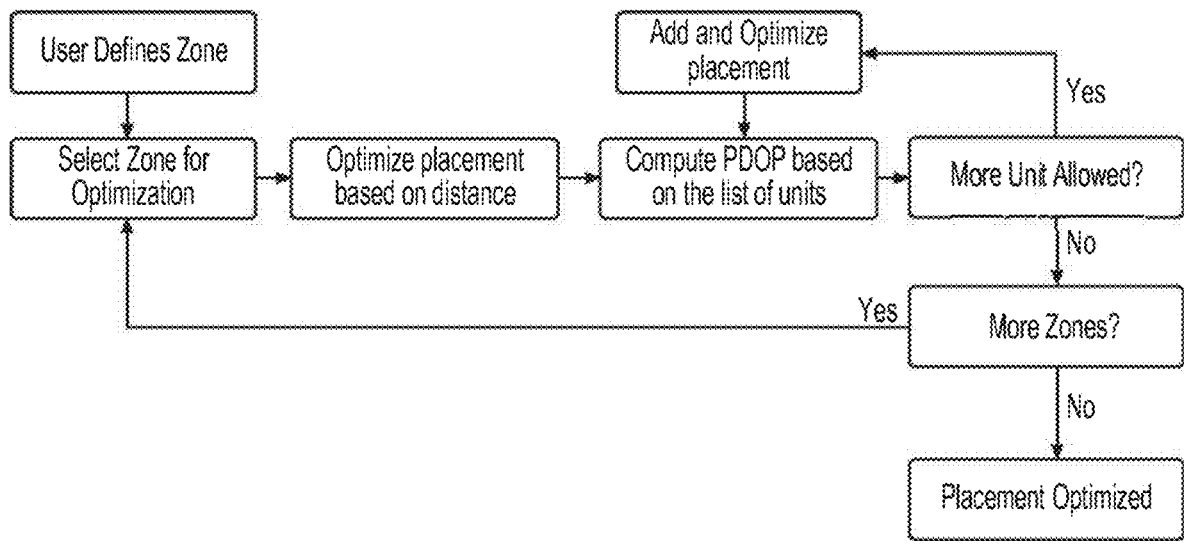
FIG. 2 is a flow diagram for optimizing reference unit locations using Position Dilution of Precision (PDOP).

As part of the exemplary system, one or more UWB tracking units may communicate with one or more external reference units, which may be mounted or located in differing locations within a use environment (e.g., an operating room during a surgical procedure). In exemplary form, a reference unit may include one or more antennas in any number of orientations and configurations. And the reference unit may communicate with other reference units and the master unit via wire or wireless connections. In exemplary form, the reference unit may behave as the master unit to other UWB tracking units, and may also be configured to determine a position of any other reference units or UWB tracking unit based on positioning techniques such as received signal strength, time difference of arrival, time of flight, and/or angle of arrival. The placement of the reference units may be arbitrary or optimized using an estimation based on position dilution of precision (PDOP) (see FIG. 2). The user may input the tracking area of interest, the desired accuracy and the number of reference units available. The optimization software determines the optimal locations of the reference unit. The software may also be configured to optimize reference unit placement in 2D or 3D.

Figure 5:
FIG. 5 is an illustration of UWB and IMU systems optionally rigidly fixed to a mobile platform.

In another alternate exemplary configuration, the UWB and/or IMU tracking systems may be rigidly fixed to a mobile platform 500, which may be in the form of a surgical robotic system, to improve performance without relying on placing external reference units around the operating room (see FIG. 5)

UWB Communication

One exemplary advantage of the exemplary system is wireless position and orientation tracking of an ultrasound probe. A second exemplary advantage of the proposed system is wireless communication between an ultrasound probe and central processing unit (CPU) using UWB technology. The high throughput obtained with UWB communication makes the proposed system ideal for transmitting the real-time ultrasound acquisition information. Transmitting the B-Mode data, radio frequency (RF) data, I/Q data, or any other acquired ultrasound signal to a CPU in real-time is performed by an UWB transceiver with a data throughput capability preferably on the order of at least 6-7 Mbps. Lossless data compression may be utilized to compress the real-time data stream so that at least 20-30 frames per second of RF, IQ, and/or B-mode data can be transmitted wirelessly for real-time processing and display.

Real-Time Virtual Guides for Joint Replacement with Augmented Reality and IMU Tracking Arthroplasty is a surgical procedure to restore the function of a joint by resurfacing one or more of the bones comprising the joint. Arthroplasty may include surgical treatments that provide restoration of normal extremity alignment, accurate implant design and optimization, secure implant fixation, and/or proper soft tissue balancing and stability. As discussed in more detail hereafter, the instant disclosure provides virtual cutting guides configured in an AR system to provide one or more computer-generated images to be overlaid on a real-world view of a surgeon/user to guide the surgeon during the surgical procedure, such as a joint replacement procedure in an operating room. In conjunction with advancing augmented reality technologies, a self-referenced hybrid navigation module based on the UWB and IMU technologies is used to improve the accuracy of simultaneous translational and rotational tracking of surgical tools and surgeon/user during a surgical procedure, as well as evaluation of intra- and post-operative kinematics of the patient.

In exemplary form, the subject matter disclosed herein corresponds to a medical application of augmented reality as part of a surgical procedure, such as a joint arthroplasty, using a head-mounted or hand-held (or body-attached) display, a regular computer screen, mobile device screen, or any combination thereof for viewing augmented reality contents. Specifically, this exemplary embodiment encompasses systems and methods for guiding surgical procedures with computer-generated images in high precision by placing virtual objects on top of a real-world view of a user in a consistent way that may provide a circumstance where a user can no longer distinguish between real objects and virtual ones.

Augmented Reality

Augmented reality (AR) is a field of computer vision and computer graphics that integrates embed synthetic information into the real-world environments. In an augmented reality experience, an end-user can be provided with additional information about the surrounding real-world of the user from computer generated images superimposed onto the real-world view of the user. Rather than virtual reality, which immerses a user only in a synthetic environment, augmented reality allows a user to interact with the synthetic world superimposed over the real-world environment. As will be discussed in more detail hereafter, the exemplary embodiment has applications outside of surgery such as, without limitation, computer gaming, simulations, engineering, training, and various other applications.

An exemplary AR system in accordance with the instant disclosure may compose of one or more color cameras, one or more depth cameras, one or more image processing units, a central processing unit, one or more network communication systems (such as Bluetooth LE, UWB, or Wifi), and any of the following feedback mechanisms: (a) optical see through feedback, which is typically a head-mounted display where information is overlaid on a visor (see FIG. 20); (b) video overlay feedback, which can be a handheld device where the display renders the video capture by the cameras and information is overlaid on top of the video; and, (c) spatial projection feedback, which may be achieved via one or more laser projector where information is projected directly onto the object (see FIG. 21). As used herein, the AR vision/tracking system, in general, refers to hardware and software operative to track objects within the user's viewing volume via computer vision, object recognition, tracking and motion estimation.

One of the primary problems confronted when one wants to provide an augmented reality experience is registration of the projected image with respect to the natural environment. More specifically, it has been previously impossible to precisely position virtual objects on top of corresponding targets in the real-world (i.e., natural environment) and update this positioning as the objects in the natural environment and the user moves. But precise alignment between the real-world objects and the augmented reality projected objects is critical for an image-guided surgery because inaccurate or jittery registration can cause misalignment of bone cuts, implant placement, and an overall negative impact on principal performance of surgical procedures.

Figure 6:
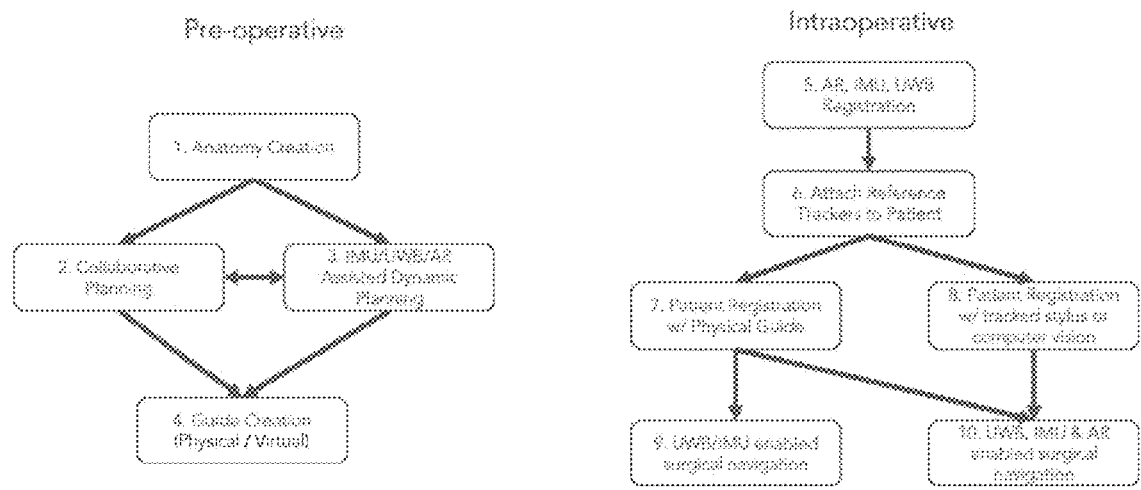
FIG. 6 is a workflow for augmented reality for joint arthroplasty in accordance with the instant disclosure.

Referring to FIG. 6, a left side flow diagram depicts a process for creating cutting guides preoperatively that may include creation of physical alignment guides, physical cutting guides, virtual alignment guides, and virtual cutting guides utilized as part of an augmented reality enabled surgery. The pre-operative steps include creating a virtual model of the patient-specific anatomy that will be the subject of the surgical procedure. The virtual anatomical model may be created from a static imaging modalities, such as computed tomography (CT), magnetic resonance imaging (MRI) and/or X-ray, or from dynamic imaging modalities such as fluoroscopy or tracker enabled ultrasound. In exemplary form, the virtual anatomical model may comprise any bone or groups of bones such as a joint including the knee, hip, shoulder, ankle and/or spine segment. Moreover, the virtual anatomical model may be used in an augmented reality system to perform collaborative surgical planning.

Collaborative surgical planning may involve a process of having two or more users connected on a network, which does not need to be local, via augmented reality hardware (helmet) to create a pre-operative surgical plan. The users creating the surgical plan can view common virtual anatomical models and implants and adjust surgical planning parameters (implant size and position) until the desired surgical plan is achieved. As changes are made to the virtual anatomical model by any user, these changes are relayed over the network to the other users and each user's visual display is updated accordingly. In a similar fashion, using avatars, users may see the position of the other users relative to the anatomical models as will be discussed in more detail hereafter.

IMU/UWB/AR assisted dynamic planning may include capturing dynamic data of the patient anatomy through one or more imaging modalities or after imaging using a combination of IMUs and/or UWB positioning systems. Communication and data transfer between each subsystem (IMU, UWB, augmented reality (AR)) may be accomplished through use of application program interfaces (API's) that translate the data from each subsystem into a format readable by the others or by a CPU. This set of communication through software API's is a common framework for all AR/IMU/UWB integrations. This dynamic data may optionally be included in the surgical planning process to establish pre- and post-operative joint conditions in the planning process.

Creation of virtual and physical alignment and cutting guides may be created using a combination of pre-operative data and an agreed upon surgical plan. Each physical alignment guide need not be a cutting guide, but rather may be a placement guide that has one or more surfaces configured to match or align with the unique bone surface of a patient. The physical alignment guide may be used to register the AR system to the patient in the operating room by being placed in a unique position on the patient based on the patient matched shape of the alignment guide. Apart from a physical guide, a virtual cutting guide—consisting of virtual parameters for cutting planes, axes for surgical axes or pin positions, patient geometry and implant parameters—may be created as part of the surgical plan. The virtual cutting guide parameters may be stored and transferred electronically, without the need for physical manufacturing processes that might otherwise be necessary for a physical cutting guide.

Referring back to FIG. 6, a right side flow diagram depicts a process for an intraoperative workflow as part of utilizing an augmented reality surgical cutting guide or a physical cutting guide. This exemplary workflow includes registration and calibration of the applicable tracking systems, which maybe AR, UWB, or IMU or any combination of those. The registration step ensures all tracking systems are synchronized to the same coordinate systems. A more detailed discussion of the registration step among various tracking systems is explained in more detail with respect to FIG. 10.

Figure 22:
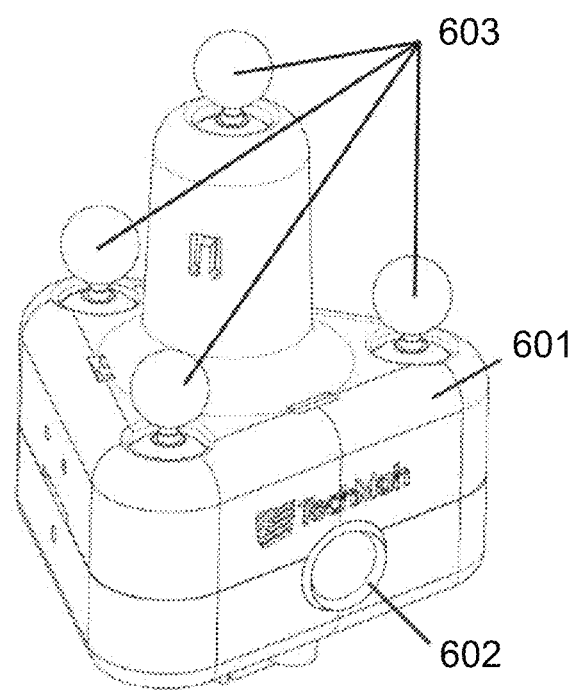
FIG. 22 is a depiction of an exemplary integral camera and UWB and IMU device that provides the capabilities to integrate optical tracking into positioning algorithms.

In an exemplary configuration, an optical tracking system may be integrated with a UWB reference unit, where it may assist and/or provide a standard frame of reference for each applicable tracking system to synchronize to (see FIG. 22).

It should also be understood that the AR system have similar limitations as an optical tracking system where it can only track objects within its field of view, and/or its viewing volume, and line-of-sight restriction. It is understood that the AR system may circumvent these limitations if it is to operate in combination with the UWB/IMU system (see FIG. 20), and that there can be more than one AR system operating at the same time. The UWB/IMU system may be attached to the patient, instruments, or any other objects such that their locations can be tracked wirelessly even they are outside the vision tracking volume of the AR system (see FIG. 25). The surgeon and surgical assistant may each have an AR system, where information captured by each system is shared wirelessly. For example, if the surgeon's AR vision tracking system has a better view of the patient joint, the tracking information may be relayed to other AR systems that do not have the patient's joint in their vision tracking volumes.

Figure 20:
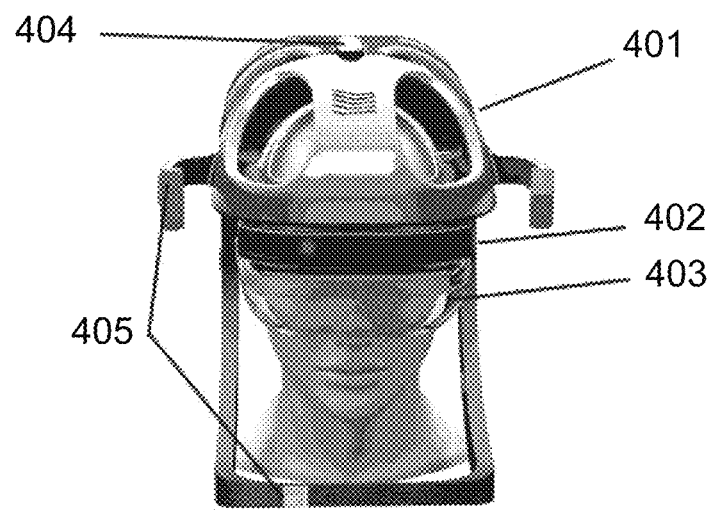
FIG. 20 is a depiction of an exemplary augmented reality system using in combination with IMU and UWB systems, and a head mounted display (AR Visor) to display information to the user.
Figure 21:
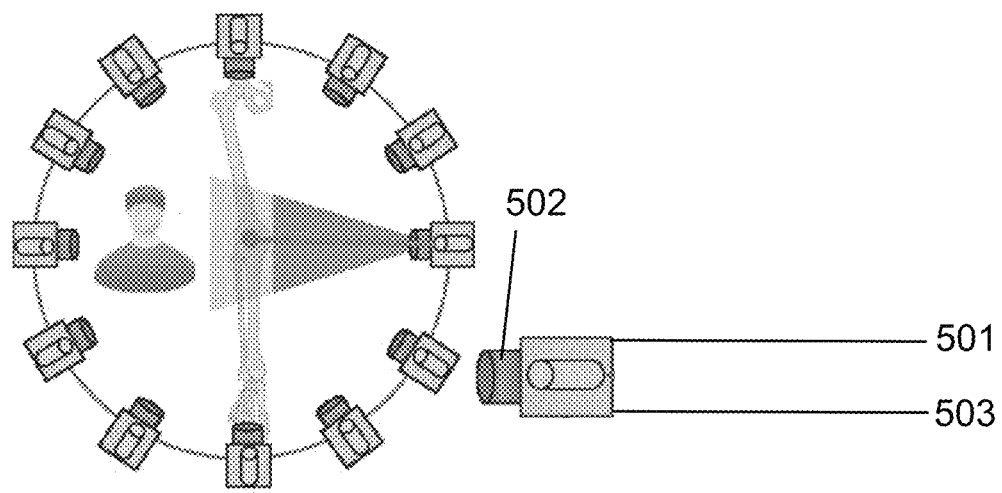
FIG. 21 is a depiction of an exemplary augmented reality system utilizing laser projectors to display information to the user.

It should further be understood that the AR information display/feedback may be implemented in the form of a head-mounted display, where information is relayed into the AR visor (see FIG. 20) or it may be implemented as a laser projecting system, where information is projected directly onto the patient (see FIG. 21). For the head-mounted display, there may be indicators overlaid in the AR visor for objects that are currently outside the viewing volume of the AR system.

Post registration and calibration, one or more reference trackers may be attached to the patient and/or applicable surgical tool. Exemplary reference trackers may each comprise an IMU and/or UWB and be attached to the patient to dynamically track the location of the patient's bone or other tissue in question. It should be noted that the AR enabled system of the instant disclosure need not require a reference tracker because one may utilize a vision tracking system to track the patient's bone (or other surgical tissue of interest) and applicable surgical instrument as long as objects are within the viewing volume of the AR cameras (see FIGS. 15 and 16). Nevertheless, utilization of reference trackers provides additional assurance that the patient's bone(s) will always be monitored even it is outside of the tracking volume of the AR system (see FIG. 25). The use of reference trackers may reduce the computation load require for computer vision, thus relieving computation burden and improving the performance of the AR system.

Post reference tracker attachment to the patient, a patient registration step may include aligning a physical guide with respect to the patient anatomy. As discussed previously, the instant exemplary process may provide for creation of a physical guide, post pre-operative planning, that can be registered to the patient's anatomy specific co-ordinates during surgery. For example, an exemplary registration method for knee arthroplasty may use a unique guide that sits on a combination of anatomical features of the patient's bone(s) that may include, such as, without limitation, the anterior cortex point, lateral and/or medical condyles for femur registration, and the superior-anterior portion of the tibia, lateral and/or lateral tibial condyles for tibia registration. In this exemplary embodiment, a position and orientation tracker comprising at least one of an IMU unit and UWB unit is attached to the physical guide. Post positioning the physical guide on the bone in a unique, known location, readings are taken from the tracker to determine the relative position and/or orientation of the physical guide, which position and/or orientation of the guide is used to calculate the location of the patient bone within the co-ordinates of the applicable tracking system. In the case of using an AR system, computer vision may be used to recognize and track the physical guide in the viewing space. The AR system can also be used in combination of the UWB/IMU tracker (see FIGS. 19, 29, 30).

Alternatively, or in addition, the exemplary embodiment may include a patient registration step that makes use of a tracked stylus or computer vision as part of virtual registration. In exemplary form, a virtual placement guide may be registered to the patient using a tracker comprising at least one of an UWB unit and an IMU unit. The tracker may be implanted as part of a stylus, where the surgeon/user may register anatomical landmarks, and/or maps the patient's bone surface. The tracked data can be specific anatomical landmarks or a point cloud that is representative of the patient's bone, which may be used to register the patient to the pre-operative surgical planning. In the circumstance where an AR system is used, the AR system may be used as a standalone tracking system to perform patient registration via computer vision (see FIGS. 15, 16) or in combination with the tracker mentioned previously (see FIG. 19).

Figure 7:
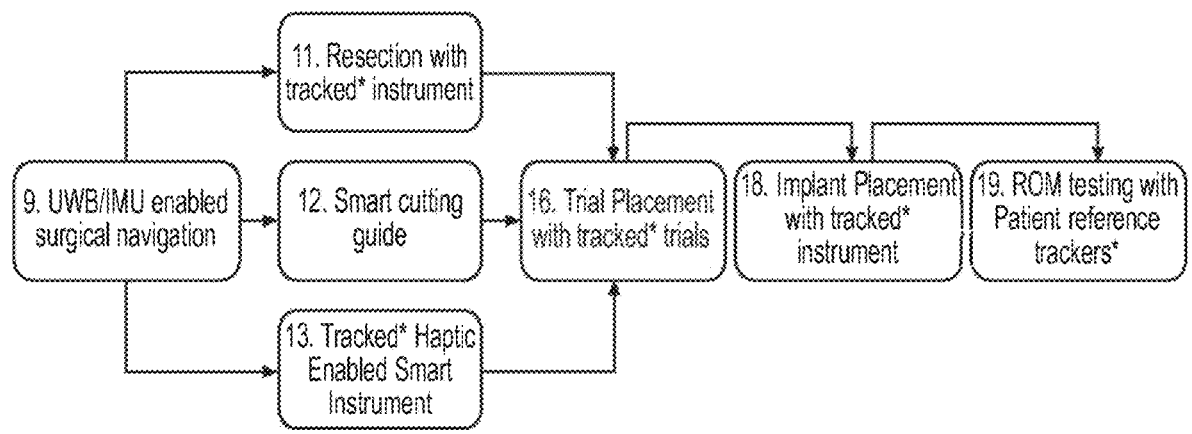
FIG. 7 is a workflow for UWB/IMU enabled surgical navigation system in accordance with the instant disclosure.

Referring to FIGS. 6 and 7, an exemplary workflow for the UWB/IMU enabled surgical navigation embodiment post patient registration is depicted in greater detail. In FIG. 6, reference numeral 8 corresponds to the UWB/IMU enabled surgical navigation embodiment more fully described in FIG. 7. As depicted in FIG. 7, a patient's bone is resected/cut, corresponding to reference numeral 11, with a tracked surgical instrument as part of a surgical procedure, consistent with the pre-operative surgical plan. Feedback information of the tracked instrument may be displayed on a standalone display unit. By way of example, the exemplary process will be described in terms of a workflow for an ankle arthroplasty using UWB/IMU based surgical guidance in section. But it should also be understood, however, that this process may also be used in other surgical procedures including, without limitation, for total knee arthroplasty.

In the context where an actual, physical cutting guide is utilized, the cutting guide may incorporate an UWB and/or IMU tracker (to comprise a smart cutting guide) to provide position and orientation information to the user concerning the cutting guide. When the physical cutting guide is utilized in combination with the position and/or orientation tracker, the information to the user may include guidance information useful as part of a joint resection. In this exemplary embodiment, the physical cutting guide may have a single or a plurality of adjustable cutting slots, each that may be adjusted manually (see FIGS. 33 and 35), or via motorized hardware (see FIGS. 34, 36), to control a set of pre-programmed, or pre-determined locations and orientations of the cut slots based upon surgical planning to produce desired resection of the patient's bone. In an alternate exemplary embodiment, the manually adjustable cutting slot may be blocked or foreclosed via the implementation of robotics or mechatronics if the current resection plane does not match the plane of the pre-operative surgical plan.

In addition to the physical cutting guide incorporating a tracker, it is also within the scope of the disclosure for surgical instruments, such as, without limitation, surgical saws to incorporate feedback mechanisms. In exemplary form, the feedback mechanisms may notify the surgeon/user whether the current/projected resection deviates from the pre-operative surgical plan. By ways of example, the surgical instrument may include a tracker comprising at least one of an UWB unit and an IMU unit that may wirelessly transmit at least one of position and orientation data to the central computer (see FIG. 33). In this fashion, when using the patient reference tracker 6 discussed with respect to FIG. 6, in combination with the surgical tool tracker, the current resection orientation and depth with respect to the patient anatomy and with respect to a pre-operative plane can be determined. The computer may send a feedback signal to the instrument if the resection orientation and depth deviates beyond a predetermined tolerance from the surgical plan, the computer may send information to the surgical tool (i.e., feedback) indicating the current orientation and/or depth is outside the tolerance of the surgical plan, hence the surgeon/user should reposition the surgical tool to arrive within the allowable tolerance. The information/feedback to the surgical instrument may be implemented as reducing or disabling the power to the motorized hardware, or it may trigger a single or a plurality of haptic motors that are embedded in the instrument, thereby providing haptic feedback to the surgeon. Alternatively, or in addition, the instrument may incorporate a visual display providing instructions to the surgeon as to the corrective action necessary to reposition the surgical instrument to effectuate a portion of the surgical procedure consistent with the pre-operative plan. By way of example, the surgical instrument may include a motorized gyro to slightly steer the orientation of the instrument, additionally providing haptic directional feedback to the surgeon to tilt the instrument in a particular direction.

As part of the exemplary embodiment, post preparation of the patient tissue to receive an implant, one or more orthopedic implant trials may be utilized that each include position and orientation tracking capabilities, as part of step 16. As discussed previously, each trial may include one or more of an UWB unit and an IMU unit that wirelessly provides feedback concerning at least one of the position and orientation of the implant trial. In this manner, the central computer may receive information from the implant trial tracker verifying positioning of the implant or providing information that the implant trial is out of position with respect to the patient bone (when using bone tracking via physical trackers or vision trackers). Eventually, an implant trial is utilized that fits the patient and provides kinematics and ligament balance consistent with the pre-operative plan, at which time the surgeon moves on to the implant placement step.

The implant placement step, identified by reference numeral 18 in FIG. 7, includes selection and placement of the orthopedic to be implanted over its useful life. By way of example, each implant may include one or more of an UWB unit and an IMU unit that wirelessly provides feedback concerning at least one of the position and orientation of the implant. In this manner, the central computer may receive information from the implant tracker verifying positioning of the implant or providing information that the implant is out of position with respect to the patient bone (when using bone tracking via physical trackers or vision trackers). Eventually, the implant is correctly positioned and affixed to the patient anatomy.

After the implant is affixed to the patient anatomy, the surgeon may take the implant through a range of motion. Because of the tracker(s) associated with the implant, the central computer records the position and/or orientation information output from the tracker and correlates this to calculate the position of the implant. This implant tracking may be compared to pre-operative kinematics and/or to a pre-operative kinematic plan to assess whether the range of motion of the implant is within the intended bounds.

Figure 8:
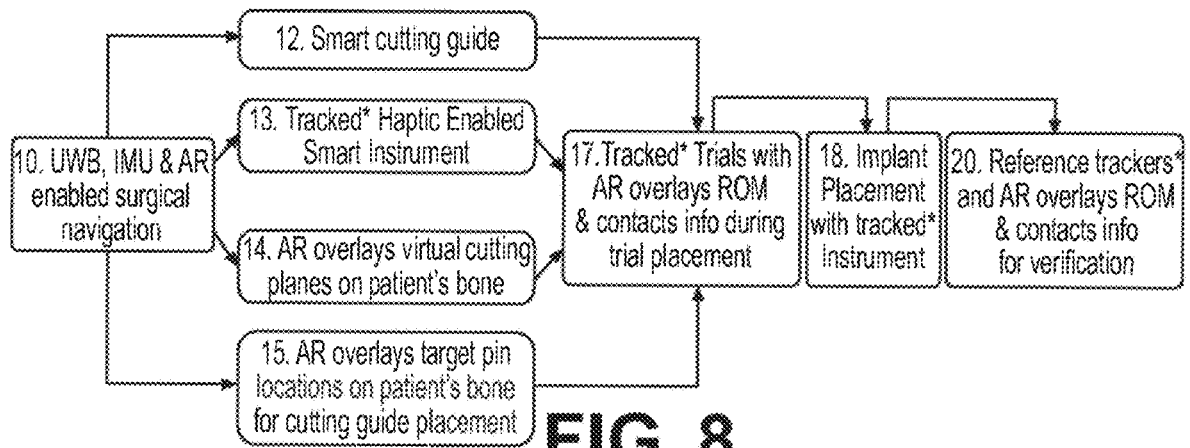
FIG. 8 is a workflow for augmented reality and UWB/IMU enabled surgical navigation system in accordance with the instant disclosure.

Turning to FIGS. 6 and 8, an exemplary workflow for the AR and UWB/IMU enabled surgical navigation embodiment post patient registration is depicted in greater detail. In FIG. 6, reference numeral 10 corresponds to the AR and UWB/IMU enabled surgical navigation embodiment more fully described in FIG. 8. As depicted in FIG. 8, in the context of a physical cutting guide, the cutting guide may incorporate at least one of an UWB unit and an IMU unit to provide position and orientation data for the cutting guide, which can be utilized with the reference tracker on the patient bone to provide guidance during the surgical procedure. The cutting guide may have a single or a plurality of adjustable cutting slots that can be adjusted manually (see FIGS. 34 and 36), or via motorized hardware (see FIGS. 35 and 37) that controls the location and orientation of the cut slots to produce the desired resection. In another alternate exemplary embodiment, the manually adjustable cutting slot may be blocked/closed off if the current resection plane does not match or fall within the predetermined tolerance of the plane called for by the pre-operative surgical plan. The AR system may assist resection by providing a virtual resection plane on the AR visor where the user may manually adjust the cutting slot of the cutting guide as described in FIG. 34.

In step 13 of FIG. 8, exemplary surgical instruments, such as a bone saw, may incorporate a multitude of feedback mechanisms to notify the surgeon that the current resection has deviated from the surgical plan. The exemplary instrument may include a tracker comprising at least one of an UWB unit and an IMU unit that may wirelessly transmit the data to the central computer. Using in combination with the reference tracker 6 of FIG. 6, the current resection orientation and depth can be determined. If the resection orientation and depth deviates from a predetermined tolerance of the pre-operative surgical plan, the computer may send feedback to the instrument. The feedback may be implemented as reducing or disabling the power to the motorized hardware, or it may trigger a single or a plurality of haptic motors to provide haptic feedback to the surgeon. In addition, or in the alternative, the feedback may be displayed on a display associated with the surgical instrument to guide the surgeon in repositioning the instrument to arrive at the proper orientation and/or position consistent with the pre-operative surgical plan. The instrument may also include a motorized gyro to slightly steer the orientation of the instrument, providing directional feedback to the surgeon to tilt the instruments. In this exemplary embodiment, the AR system may assist in combination with the technologies previously described by providing warning, feedback, and/or directional information regarding to the resection plane orientation and resection depth, which are overlaid on the AR visor, or computer screen, or laser projected onto the patient and instrument (see FIG. 27).

As depicted as step 14 in FIG. 8, the AR system may provide virtual resection and/or resurfacing guidance indicative of the location and orientation of the area where joint resection and/or resurfacing may be required. For example, a knee implant may require multiple resection cuts on the patient's distal femoral joint and proximal tibial joint. The AR system may indicate all of the resection planes needed so that the surgeon may perform adjustment prior to resecting any bone. The AR system may procedurally display the resection required so that it guides the surgeons during each resection step (see FIG. 40).

In instances where a physical cutting guide may be utilized, the exemplary AR system may provide virtual pin locations as part of the visual display of the AR visor, or computer screen, or laser projected onto the patient to assist the surgeon in cutting the pin location holes. In this exemplary embodiment, the cutting guide may be generic or patient-specific. In either instance, the AR visor may virtually display the resection that is produced by current pin placement so that the surgeon may perform adjustment prior to resecting the bone. The AR system may also procedurally display pin locations for each cutting guide needed during each procedure (see FIGS. 28, 38, 39).

Post resection of the patient's bone(s), the exemplary process flow moves on to step 17, where the AR system may operate in combination with trial components enabled with at least one of an UWB unit and an IMU unit, and/or utilizing the reference trackers on the patient bone(s) to allow orthopedic implant trial placement. The AR may overlay information regarding to the placement of the trial component, the range of motion of the patient, and the contacting area of the implant during motion (see FIG. 26).

Once the implant trial sequence has been concluded, and the implant range of motion and contacts verified, the AR system may work in combination with one or more surgical instruments and bone reference trackers (enabled by at least one of an UWB unit and an IMU unit) to provide placement information concerning the implant virtually on the AR visor, or computer screen, or laser projected onto the patient. For example, utilizing the location and orientation information from the trackers on the patient's bone and surgical instrument, the AR system may provide visualization of the placement of the implant by overlaying a virtual bone and the virtual acetabular cup on the patient in the context of a total hip arthroplasty (see FIGS. 29-32).

Post implantation of the orthopedic implant, the surgeon may take the implant through a range of motion as identified by reference numeral 20 in FIG. 8. The AR system may operate in combination with the reference trackers on the patient bone and implant to perform a kinematic verification, where the surgeon can manually manipulate the bone and/or joint. The AR may overlay information regarding the placement of the implant, the range of motion of the implant, and the contacting area of the implant during motion (see FIG. 26).

Figure 9:
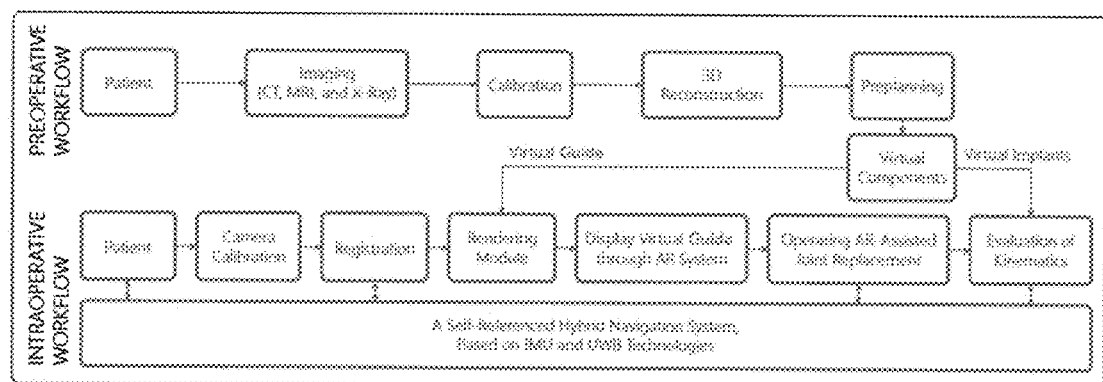
FIG. 9 is a block diagram of one example embodiment for preoperative and intraoperative workflows to create virtual guides for joint arthroplasty using the AR system and a hybrid tracking systems such as IMU and UWB in accordance with the instant disclosure.

Turning to FIG. 9, a block diagram depicts an exemplary embodiment for preoperative and intraoperative workflows in greater detail than that depicted in FIG. 6 to create virtual jigs for joint arthroplasty using an AR system and a hybrid tracking systems such as IMU and UWB. In the preoperative workflow, the patient specific anatomy must be extracted or constructed by using some imaging modalities such as computed tomography (CT), magnetic resonance imaging (MRI), dual plane X-Ray radiographs, single plane fluoroscopy, or a combination thereof. Post completion of calibration process, a reconstructed 3D patient specific anatomy virtual model is created. Using the reconstructed virtual bone model, virtual cutting guides and implants may be created in the preplanning process.

In the intraoperative workflow component, a patient may be tagged with multiple rigid units attached onto the patient's anatomy. The term "unit" in the exemplary embodiments can be understood as one or more sensors to measure the location and orientation of a target that is wirelessly connected to a self-referenced hybrid navigation system based on IMU and UWB technologies. Post positioning one or more rigid units on the patient, a camera calibration may be performed to provide registration between the real world and the virtual world provided by the AR. In other words, the camera registration process may include registration between different coordinates of virtual- and real-world coordinate systems using a target tracker that may be selected from one of the following trackers: a marker detection, feature correspondence, 3D model-based object detection, self-referenced hybrid navigation system, or on any combination thereof. Post registration and post virtual guide creation, the virtual guide is rendered using one or more augmented reality modules to allow depiction of the virtual guide aligned with the real world patient anatomy. In this fashion, the virtual guides may be visually superimposed onto the patient's anatomy through either an overlay image on a head-mounted or hand-held (or body-attached) display or through a projection system, which may consist of lasers or projectors for superimposing the virtual guide. The virtual implants can be used to evaluate intra- and post-operative kinematics where implant components are sized and placed on the virtual bone models in software.

Figure 10:
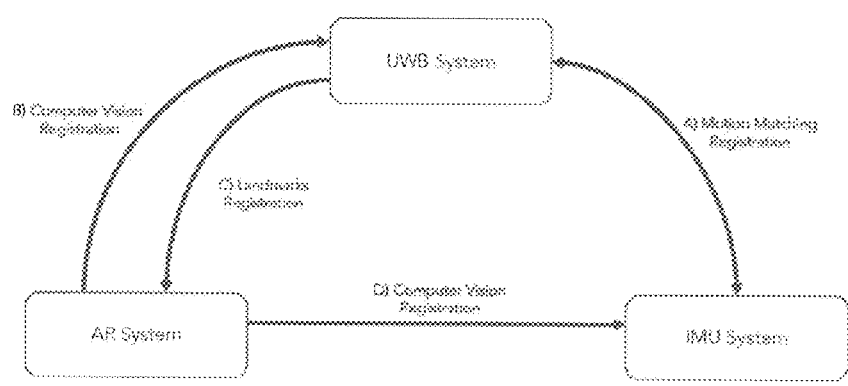
FIG. 10 is a diagram depicting registration relationships among augmented reality, UWB and IMU systems in accordance with the instant disclosure.

Referring to FIG. 10, a more detailed discussion of the techniques utilized to establish registration relationships between the tracking units and the AR system. Registration between the IMU and UWB units may be accomplished via a motion matching registration, where the surgeon/user may rotate the tracker in known orientations, or rotate the unit in any orientation until enough information is collected, or rotate via robotics or mechatronic, and the registration software running on a central computer can determine the transformation so that the UWB and IMU coordinate will match with each other. Registration between the UWB and AR system may be accomplished by either registering the AR coordinate system to the UWB coordinate system, or vice versa.

In a first exemplary method to register the tracking units to the AR system presumes that the AR system is mobile and cameras associated with the AR system may be positioned freely. As part of the registration process, each camera of the AR system may capture a single or multiple registration targets, which may be image, or objects, providing that their locations are previously measure in the UWB coordinate. The registration of the UWB unit and AR system may be completed by matching the coordinates of the registration targets. In an alternate exemplary embodiment, an object such as a stylus that is recognizable by the AR system may incorporate an UWB unit and/or an IMU unit, where the user may maneuver the pointer arbitrarily in front of the camera of the AR system, or the user may use the stylus to collect points from an known object while capturing the activity with the camera of the AR system, or the pointer may be maneuvered via robotics or mechatronics while the activity is captured by the camera of the AR system. The location of the stylus, which may be represented as 3D points, or 3D point cloud, collected through the AR system and UWB units during these activities may be used together to determine the transformation between the two tracking system coordinates. In another alternate exemplary embodiment, a device may have the AR system and an UWB unit and/or IMU unit rigidly attached together. The user may maneuver the device, or walk around with the device, or the device may be maneuvered via robotics or mechatronics so that the location of the device can be established and represented as 3D points, or 3D point cloud, etc. to determine the transformation between the two tracking system coordinates.

In a first exemplary method to register the tracking units to the AR system presumes that the AR system is immobile, where each camera of the AR system is fixed. In this exemplary method, an object such as a stylus that is recognizable by the AR system may incorporate an UWB unit and/or an IMU unit, where the user may maneuver the stylus arbitrarily in front of the camera of the AR system, or the user may use the stylus to collect points from an known object while capturing the activity with the camera of the AR system, or the stylus may be maneuvered via robotics or mechatronics while the activity is captured by the camera of the AR system. The location of the stylus, which may be represented as 3D points, or 3D point cloud, collected through the AR system and UWB and/or IMU units during these activities may be used together to determine the transformation between the two tracking system coordinates. In another alternate exemplary embodiment, the stylus may not be recognizable by the AR system providing a secondary image, or object is recognizable. In that instance, the user may "paint" or collect specific registration points on the image or object. The location of the stylus, which may be represented as 3D points, or 3D point cloud, collected through the AR system and UWB and/or IMU units during these activities may be used together to determine the transformation between the two tracking system coordinates.

Finally, registration between IMU unit and AR system may be accomplished by embedding the IMU unit within an object recognizable by the AR system. The user may maneuver the object arbitrarily in front of the camera of the AR system, or the user may asked to position the object in different orientations while capturing the activity with the camera of the AR system, or the object may be maneuvered via robotics or mechatronics while the activity is captured by the camera of the AR system. The orientation of the object, which may be represented as any orientation representation such as Euler Angles, Directional Cosine Matrix, or quaternion, collected through the AR system and IMU units during these activities may be used together to determine the transformation between the two tracking coordinates.

Turning back to FIG. 6, a more detailed discussion of the collaborative surgical planning step 6 is provided hereafter. Collaborative surgical planning allows one to share and communicate holographic applications at the same time in terms of creating a pre-operative surgical plan with other users who may be in the same room or working remotely where the applications are running on each device for viewing augmented reality contents. Collaborative surgical planning applications may work with multiple devices such as hand-held tablets or mobile phones, head-mounted augmented reality devices, laptops, or desktops. The collaborative framework based on network communication technologies enables support of multiple platforms on different devices, which are connected to internet or a local network. One exemplary embodiment for a collaborative process to perform surgical planning may be built on server and client architecture. A server component as a backend computer may manage tracking connection and disconnection clients, and synchronizing messages among clients. For real-time communications with all the devices connected to the server, an exemplary communication protocol that may be used is the user datagram protocol (UDP) to relay all the messages among the devices. In this exemplary embodiment, a message packet consisting of an array of bytes with specific format may include control information and user data (i.e., identification number, position, orientation, inputs, etc.). As clients, the applications running on each device communicate tasks for surgical planning by relaying informative messages among other users through synced networks to seamlessly render situated visualization in the real-time. The tasks in the context of surgical applications may include position of reference points on the target bones, bone cutting in a typical total joint replacement, implant size and position, implant alignment, etc.

Figure 11:
FIG. 11 is an exemplary photograph for a virtual bone cutting plan showing a orange colored 3D model showing the position of another user relative to the augmented reality system as part of a collaborative surgical planning.
Figure 12:
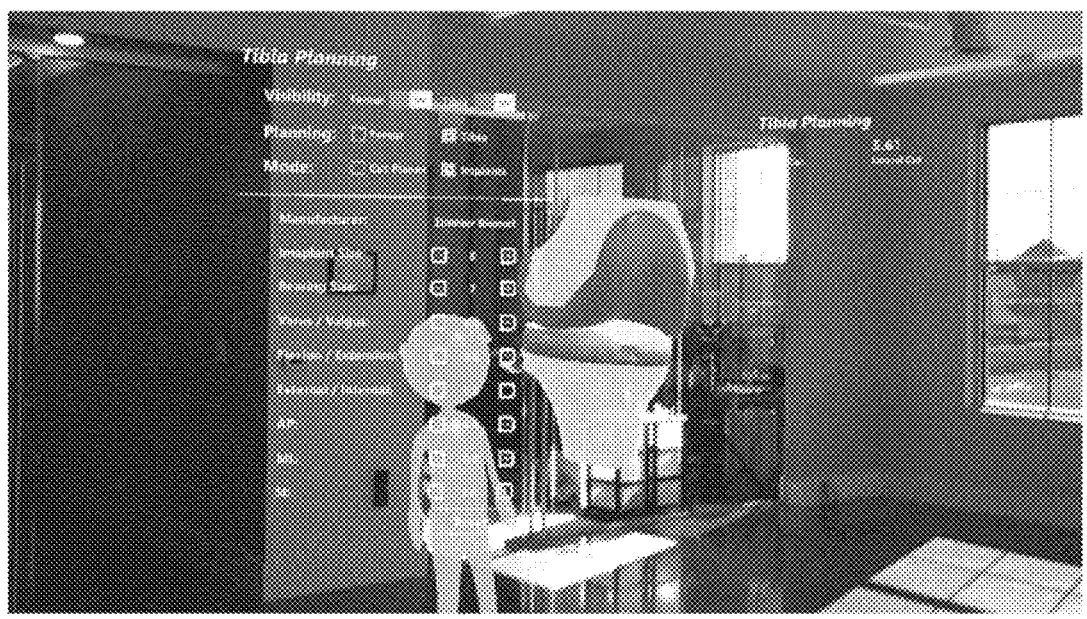
FIG. 12 is another exemplary photograph for a virtual implant placement plan showing a orange colored 3D model showing the position of another user relative to the augmented reality system as part of a collaborative surgical planning.

As shown in FIGS. 11 and 12, the task of bone cutting is designed to specify the desired resection planes associated with the target bone and to fit implants into a unique position and orientation on the bony structure. To improve communication with other users, the exemplary embodiment enables tracking the position of other users and to deploy a 3D avatar model representative of the positioning the users relative to the anatomical models as an anchor. According to an aspect of directly communicating with other users, a group voice chatting function may be supported. To enhance computational performance, graphical models for situated visualization in the considered tasks may be only managed and rendered on each device, and then updated by receiving messages over networks with any changes in the current view.

Figure 13:
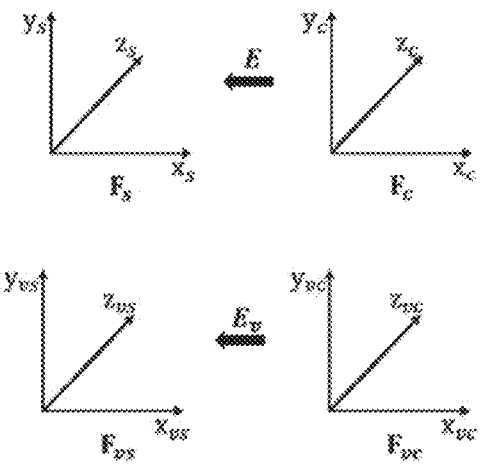
FIG. 13 is a diagram depicting transformations of different coordinate systems in augmented reality.

Referring to FIG. 13, transformations of different coordinate systems in AR is quite important. In AR systems in accordance with the instant disclosure, the real world includes a real world includes the scene frame $F_s$ and camera frame $F_c$ and a virtual world includes virtual scene frame $F_{vs}$ and virtual camera frame $F_{vc}$. Without loss of generality, assume that $F_s$ and $F_{vs}$ are equivalent, that is, $F_s = F_{vs}$. To precisely project virtual objects onto the current world frame, $F_c$ and $F_{vc}$ must be located at the same position and share the same camera parameters (e.g., focal length, viewing angle, skew, etc.). To accurate viewing of virtual guides superimposed onto the real environments as well as virtual models such as medical tools, $F_c$ and $F_{vc}$ are precisely aligned before a compositing step to produce the augmented reality displays. To this end, the unknown parameters of transformation E defining the pose in the world frame $F_s$ regarding $F_c$ require to be estimated. In the process of the camera pose estimation in the world frame (e.g., registration), inaccurate or jittery pose estimations (position and orientation) can cause an overall negative impact on performance (in the case of surgery, on the surgical procedure itself). In the following sections, a comprehensive description of several developed approaches to accurately insert virtual objects such as virtual guides into the real-world environments is provided.

In the context of an AR system utilizing a camera and a projector, an exemplary process for calibrating the camera to the projector is described hereafter. This exemplary process involves approximating a camera model, based on a pin-hole camera model, that may be defined by a 3×4 three-dimensional perspective projection matrix. Given a two-dimensional projection pixel denoted by $m=[u, v]^T$, and a three-dimensional point denoted by $M=[X, Y, Z]^T$, the corresponding points $\tilde{x}$ in the homogeneous coordinates are denoted as $\tilde{m}=[u,v,1]^T$ and $\tilde{M}=[X,Y,Z,1]^T$, respectively. A 3×4 transformation matrix E between the world coordinate system and the camera coordinate system is defined as:

$$E = [R \mid t], R = \begin{bmatrix} r_{xx} & r_{xy} & r_{xz} \\ r_{yx} & r_{yy} & r_{yz} \\ r_{zx} & r_{zy} & r_{zz} \end{bmatrix}, \quad (1)$$

$$t = \begin{bmatrix} t_x \\ t_y \\ t_z \end{bmatrix}$$

where R and t are a rotation matrix and a translation matrix, respectively. E is also called extrinsics that define the position of the camera P. The relationship between the three-dimensional point M and its image projection pixel m is given by:

$$s\tilde{m} = KE\tilde{M}, K = \begin{bmatrix} f_x & \gamma & u_0 \\ 0 & f_y & v_0 \\ 0 & 0 & 1 \end{bmatrix}, \quad (2)$$

where s is an arbitrary scale factor, K is known as a 3×3 camera intrinsic matrix with the focal lengths $f_x$ and $f_y$ in pixel units, the coordinates of the principal point ($u_0$, $v_0$), and a skew parameter $\gamma$. The skew parameter $\gamma$ is set to zero herein, since modern manufacturing techniques for most normal cameras render this negligible. A 3×4 camera projection matrix mixing both intrinsic and extrinsic parameters is given by P̂=KE. Using the concentrated camera projection matrix P, the equation (2) can be redefined as:

$$s\tilde{m} = \hat{P}\tilde{M}. \tag{3}$$

In consideration of computing the depth values, a 4×4 camera projection matrix may be employed by adding one row to the 3×4 camera projection matrix.

As a prefatory step of an intraoperative workflow when using an AR system, where a camera (or multiple cameras) are built into a head-mounted or hand-held (or body-attached) display device should be calibrated. In general, camera calibration is utilized to find camera intrinsics (also called internal parameters). In this routine, calibration targets the camera on a known structure having many individual and identifiable points. By viewing this structure from different angles, the relative location and orientation of the camera for each image as well as the intrinsics of the camera may be computed. To provide multiple views, a diverse set of images at different orientations and distances are taken. Specific to a head-mounted or hand-held AR system, multiple views of a known planar object (e.g., chessboard) are taken along with rotating the display device and moving back and forth (instead of moving the target). Next, the detected points on the known planar object are used to compute the homography matrix related to calculating both the individual translations and rotations for each view as well as the intrinsic parameters where the intrinsics are defined as the same set of parameters for all views. By refining the intrinsic and extrinsic parameters, the camera can be calibrated. The intrinsic parameters calibrated herein may be stored as metadata in a server, computer, smartphone, or tablet. In a special case, if an optical see-through head-mounted display provides the availability to access the location of the camera in the world coordinate and the perspective projection of the camera when a photo or video is taken, all the steps of the camera calibration may be disregarded. In exemplary form, the perspective projection matrix of a projector model based on a pin-hole projector model is defined by the same set of parameters as the pin-hole camera model. For this reason, the perspective projection matrix of the projector model can be found by performing the same procedures of the camera calibration.

In accordance with the instant disclosure, the following discussion provides a process and structures for solving an open-problem of pose estimation, which estimates a pose of a three-dimensional object from a set of two-dimensional point projections. The problem of pose estimation is also known as estimating extrinsic parameters of a camera. The pose of the camera may be recovered by estimating a homography that is an invertible mapping of a set of points on the perspective plane. The application of the pose estimation may provide the ability to simultaneously estimate both three-dimensional geometry and camera pose from the stored object as a reference and an object in the current scene as a target. In addition, the UWB and/or IMU unit embedded as part of the AR system may allow one to initially identify the localization of the surgeon in the operating room in application to a medical procedure. By way of example, the position of the stationary references in the real-world as well as any other geometry of the references is predetermined to align the external tracking coordinate system to an AR coordinate system in the rendering framework.

As discussed in more detail hereafter, various exemplary approaches may be utilized to estimate the pose of the camera including, but not limited to: two-dimensional marker detection, two-dimensional feature correspondence, and three-dimensional model-based object detection. These exemplary approaches may also be used to track the position and orientation of a target object or reference in AR applications where virtual guides or annotations are superimposed on top of the target surface through AR displays.

Figure 14:
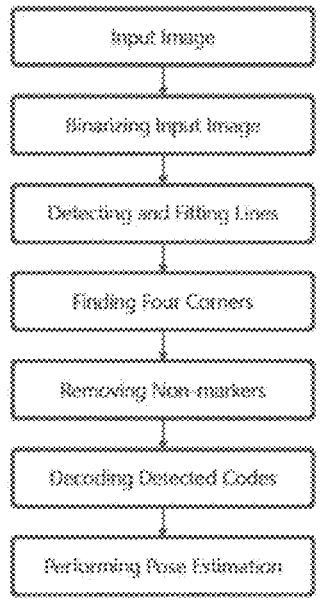
FIG. 14 is a block diagram of an exemplary method for a rectangular shape-based marker detection approach.

As shown in FIG. 14, a block diagram is depicted of an exemplary process for a rectangular shape-based marker detection approach to transform coordinate systems of the real and virtual worlds. Given a color input image, one exemplary process converts the input image to a black-and-white colored image. After applying fundamental image processing algorithms to remove noises, the process detects lines or edges in the binarized image to fit a preferred shape of the marker to each cluster of unordered boundary points. Next, the process finds four candidate corners to fit lines to each side of the marker. As part of this process, some extra filtering takes place to remove undesired corners on obvious non-marker regions. To identify the individual markers, the process decodes the detected codes in each marker. As the final step of the process, estimates of the camera pose are generated to render any virtual models of the corresponding target on top of the target surface along with the real-world view of a user.

Alternatively, one may utilize a circular shape-based marker detection approach to transform coordinate systems of the real and virtual worlds. Depending on the marker detection algorithm, different markers are tagged to each of the references. The markers may be designed as circular shapes with unique textures consisting of the combination of binary color patterns. The textures in the markers are used to identify the markers. At the core of marker detection, fiducials (e.g., edges) on the markers are used to estimate the camera pose through multiple frames in different views. Specifically, an exemplary method for the marker detection may perform some or all the following process steps: (1) binarizing a color input image; (2) removing non-markers; (3) decoding the detected codes in the marker to identify the marker; and (4) estimating the pose of the camera. As part of binarizing a color input image, an adaptive thresholding approach may be employed using the minimum and maximum values within tiles in the grayscale image that are converted from a color input image and then divided into tiles of specific dimensions in pixels.

Figure 15:
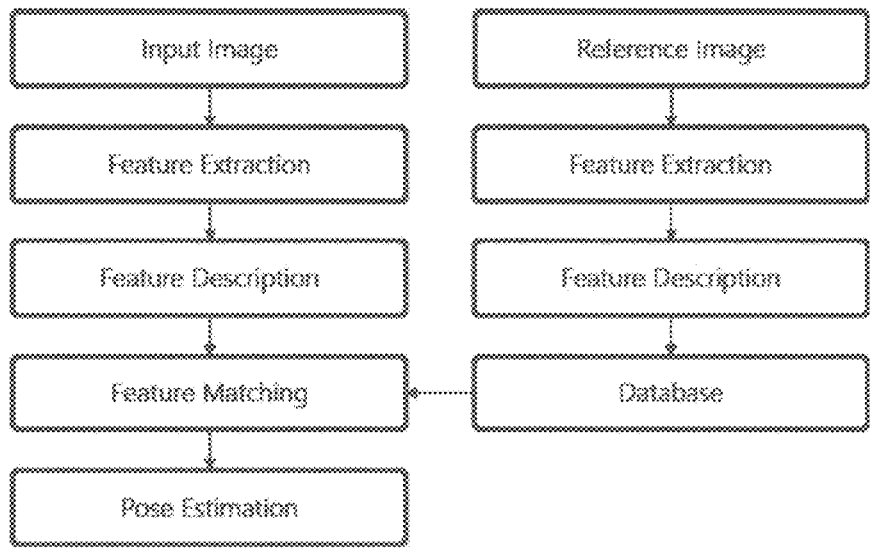
FIG. 15 is a block diagram of an exemplary method for a two-dimensional feature correspondence approach.

Referencing FIG. 15, a block diagram is depicted of an exemplary process for two-dimensional feature correspondence approach to transform coordinate systems of the real and virtual worlds. The correspondences between the features (e.g., corners, curves, lines, edges, or regions) in reference and target images are established to estimate a homography matrix that maps from one image to another. The homography is also known as a perspective transform operating on homogeneous coordinates. In both input images, the exemplary process detects candidate features among all the pixels in a target image. Next, the process describes each the candidate features with its local information around the feature location and then, the process encodes the local information of each detected feature to a vector known as a feature descriptor. Once describing all the features, the process searches in multi-scales for matching feature descriptors and then the process estimates the camera pose by justifying the parameters of the homography matrix. By way of example, once the feature descriptors in the reference image are defined, they may be embedded or stored as a text or table file in a server, computer, smartphone, or tablet in embodiments to improve the total processing time of the feature correspondence approach.

Figure 16:
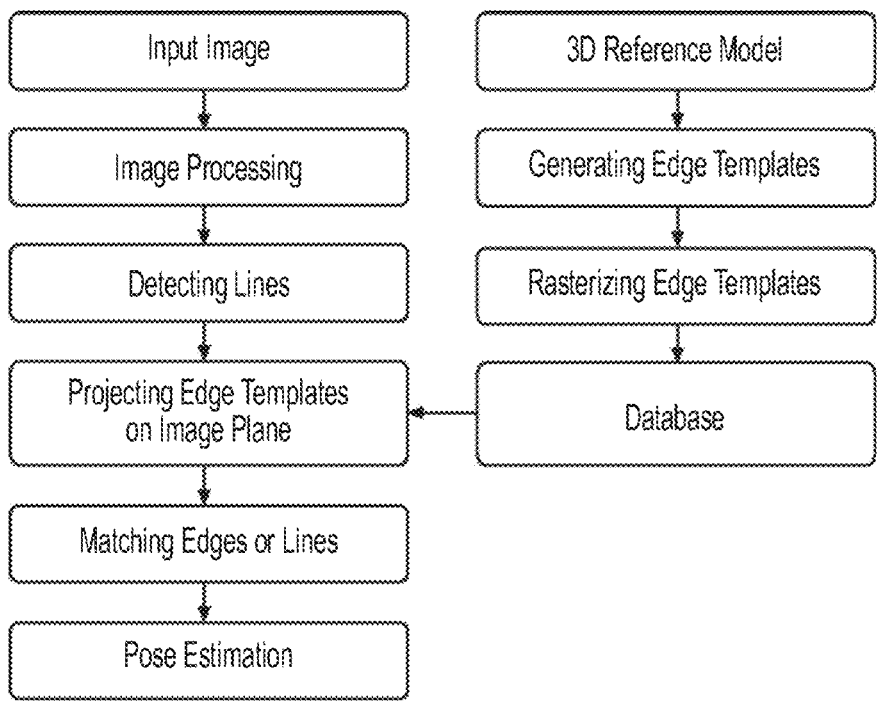
FIG. 16 is a block diagram of an exemplary method for a three-dimensional model-based object detection approach.

Turning to FIG. 16, a block diagram is depicted of an exemplary process for a three-dimensional model-based object detection approach to transform coordinate systems of the real and virtual worlds. The three-dimensional model-based object detection process deals with a set of challenging untextured objects (e.g., metals or outputs of a three-dimensional printer or a rapid prototyping machine). To tackle these challenging problems in untextured objects, this exemplary process may first generate edge templates as a preprocessing from the polygonal mesh model of an untextured target object as appearances of the model change with respect to rotational variations in x, y, and z axes. Next, the process rasterizes each of the edge templates in different views. Given a color input image, the process performs a fundamental image processing algorithm to convert a color input image to a grayscale image. Then, the process detects all the candidate edges or lines on the grayscale image and projects the set of sample rater points in the results of rasterizing the edge templates to the edges or lines on the image plane. Once the projection is complete, the process searches in multi-scales for matching the edge template with minimum distance between the edge template and edges or lines detected in the input image. As a final step, the process estimates the homography to precisely locate the model on the image plane. All the edge templates and set of sample raster points may be embedded or stored as a text or table file in a server, computer, smartphone, or tablet in embodiments.

Figure 17:
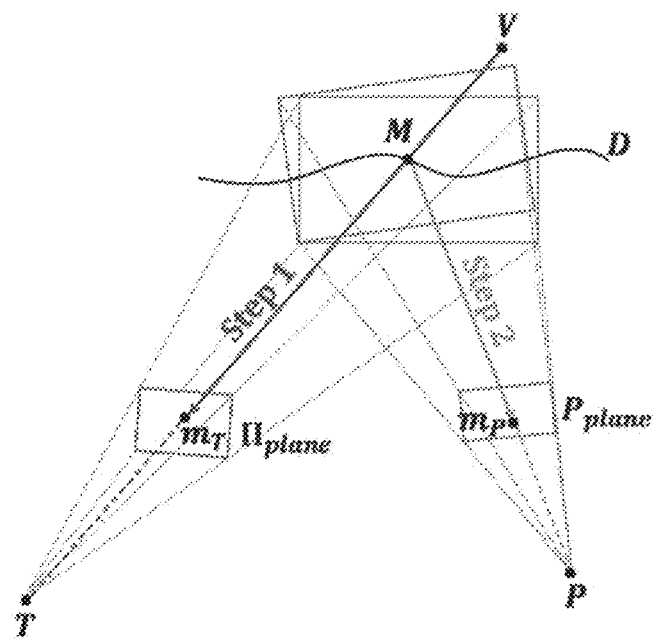
FIG. 17 is a diagram of a rendering framework in a fundamental forward mapping including two rendering steps.

Moving on to FIG. 17, an example of a rendering framework in a fundamental forward mapping process is depicted. The exemplary process includes two rendering steps. In the first step, the ray TV is stated using two parameters on an arbitrary projection plane in the frustum of a perspective view along with the user T. This is related to computing the image of a virtual object V from the user location T on that projection plane. The projection is represented by the projection matrix P_T where m_T on the image plane Π_plane is the projected pixel. It is necessary for an intermediate point M on the display frame D to transfer pixel m_T to pixel m_p. After transferring the pixel m_T to the nearest point on the display frame D along the ray Tm_T, the image of V transferred from Π_plane through the center of projection T is augmented onto the display frame D. In the second step, the image of the augmented display is discovered by transferring the point M to pixel m_P via the camera or projector projection matrix.

The following discussion explains the process and technology for rendering three-dimensional (3D) models as part of an AR display. In order to render 3D models as part of the targets in the virtual-world coordinate of AR displays, one may consider the geometric framework based on a pin-hole camera or projector model. Various configurations of each component of this exemplary process for rendering images of three-dimensional virtual objects may include: (1) a user T may be moving or be static; (2) a projector or camera P to create computer-generated images on a display that may be embedded in an arbitrary position on a head-mounted or hand-held (or body-attached) display device or a surrounding environment; and (3) the display surface D may be planar or non-planar. The geometric framework may define the geometric relationship among a user T, a camera P, a virtual-world frame $F_{vs}$, and a real-world frame $F_s$. The frames $F_{vs}$ and $F_s$ are simplified herein as a display frame D. Such a geometric relationship among the geometric components is in order that for any three-dimensional point V on the virtual object, the mapping from the three-dimensional virtual object space to the two-dimensional camera image space can be represented using an intermediate point on the display frame D where the projection pixel $m_p$ of a virtual point V is intersected by the ray $P_cM$ with a camera image plane $P_{plane}$ where $P_c$ is the center of the camera and M is the intersection of the ray TV with the display frame D.

If TM=kTV, the relationship between a virtual point V and its projection pixel $m_p$ regarding the geometric components such as a user T, a camera projection matrix $\hat{P}$, and a display frame D is defined as:

$$\tilde{m}_p \sim \hat{P}\tilde{M}, \tilde{M}=[TV \oplus D] \qquad (4)$$

where the operator ⊕ denotes the intersection of a ray TV and a display frame D and ~ denotes equality up to scale. If k>0, it ensures that the display and virtual object are on the same side of T. The condition 0<k≤1 indicates that the virtual object is behind the display frame regarding the user. if k>1, the virtual object is in front of the display frame.

According to an aspect of the preference of a fundamental forward or backward mapping, the order of the two following steps may be reversed. In exemplary form, the steps may be valid for any configurations of AR applications. In the first step, the ray TV is represented using two parameters on an arbitrary projection plane in the frustum of a perspective view along with the user T. This is corresponding to computing the image of a virtual object V from the user location T on that projection plane. The projection is represented by the projection matrix $P_T$ and $m_T$ on the image plane $\Pi_{plane}$ indicates the projected pixel. An intermediate point M on the display frame is required to transfer pixel $m_T$ to pixel $m_p$. Once the pixel $m_T$ is transferred to the nearest point on the display frame D along the ray $Tm_T$, the image of V transferred from $\Pi_{plane}$ through the center of projection T is augmented onto the display frame D. In the second step, the image of the augmented display is found by transferring the point M to pixel $m_p$ using the camera projection matrix defining the internal and external parameters of the camera in the equation (3). In three-dimensional computer graphics, the two transformation matrixes such as $T_p$ and $P_p$, may be necessary to define the pixel projection, visibility, and view frustum operations. In this exemplary process, an application-specified coordinate system and both transformation matrixes may be embedded as metadata that enable to locate the images taken in the real-world.

In an exemplary embodiment for rendering a 3D virtual model on an optical see-through display built into a head-mounted AR device, as shown in FIG. 20, may use fiducial points extracted from a target tracker, a marker detection, feature correspondence, 3D model-based object detection, external tracking system, or on any combination thereof. By employing the backward mapping, the pose estimation process for approximating the optimal points $\hat{M}_i$ may perform some or all the following steps: (1) finding the projection pixels $m_p^{i,k}$ on the camera image plane $P_{plane}$ which correspond to the fiducial pixels $f_i$ estimated by the target trackers where i and k are the index of the fiducial pixels and the captured images in different views, respectively; (2) computing the position of the projected point $M_{i,k}$ of each vertex of a three-dimensional model by projecting the projection pixel $m_p^{i,k}$ onto the display frame D via the camera projection model $P_p$ in which the point $M_{i,k}$ is intersected by the ray $T_kV_i$; (3) solving the approximated intersection of multiple rays $T_kV_i$ by using the first step in terms of computing the image of V from the user location T as stated in the fundamental forward mapping and updating the position of $\hat{M}_i$; and, (4) iterating previous steps until one of the following conditions is satisfied: (i) the approximated intersection of the multiple rays is no more updated; (ii) the maximum number of iterations is reached; or, (iii) a convergence tolerance is achieved. In this process, the projection pixels $m_{i,k}$ may be normalized in the transformed image coordinate. During the alignment process, the virtual model formed by $\hat{M}_i$ in the virtual-world coordinate may visually indicate a current location of the target object as well as the alignment quality to a user in real-time.

The following discussion provides an exemplary solution to approximate the intersection of multiple rays. Given point $p=(x,y)$ in two dimensions or $p=(x,y,z)$ in three dimensions, the unit vector u is the vector of cosines of vector v regarding each of the coordinate axes, $$u = \frac{1}{\|v\|}(v \cdot e_1, v \cdot e_2, \ldots, v \cdot e_n), \quad (5)$$

where $e_j$ is the unit vector for coordinate axis j. The unit vector u indicates the orientation of a vector v. For a line, the parametric equation can be given by $$p(t) = tu + p_0, \quad (6)$$

where $p_0$ represents a point passing through the line for $-\infty \leq t \leq \infty$. If the domain of t is limited in $0 \leq t \leq \infty$, rays (i.e., half open lines) would be denoted as a vector that starts at point $p_0$ and points in the direction u. Let $v_1 = p_1 - p_0$ and $v_2 = p_2 - p_0$ where three non-collinear points $p_0$, $p_1$, and $p_2$ can define two distinct vectors $v_1$ and $v_2$. Since the two vectors lie on a plane in space, the normal to the plane can be defined as:

$$n = v_1 \times v_2. \quad (7)$$

where × is the cross product of vectors $v_1$ and $v_2$. For the plane, the set of points p orthogonal to n is given by:

$$n \cdot (p - p_0) = 0, \quad (8)$$

where a point $p_0$ in the plane is offset from the origin. To compute the shortest distance from a point to a line, the squared perpendicular distance approach may be employed. The squared perpendicular distance D can be given by:

$$\begin{aligned} D(p; p_0, u) &= \|(p - p_0) - ((p - p_0)^T u)u\|_2^2 \\ &= \|(p - p_0) - u^T u(p - p_0)\|_2^2 \\ &= \|(I - u^T u)(p - p_0)\|_2^2 \\ &= (p - p_0)^T (I - u^T u)^T (I - u^T u)(p - p_0) \\ &= (p - p_0)^T (I - u^T u)(p - p_0) \end{aligned} \quad (9)$$

where I is the identity matrix and $(I - u^T u)$ is idempotent such that $(I - u^T u)^2 = (I - u^T u)^T (I - u^T u) = (I - u^T u)$. Given multiple R rays, the unique solution in a least-squares sense to the intersection of the set of R may be found to minimize the sum of squared distances:

$$D(p; p_0^R, u^R) = \sum_{l=1}^{R} D(p; p_0^l, u^l) = \sum_{l=1}^{R} (p - p_0^l)^T (I - u^{l^T} u^l)(p - p_0^l). \quad (10)$$

In a quadratic form of p, the objective of the minimal squared distance can be defined:

$$\hat{p} = \underset{p}{\arg\min} D(p; p_0^R, u^R) \quad (11)$$

To find the minimum of the sum of squared distances, the equation (10) is differentiated with respect to p as follows:

$$\frac{\partial D}{\partial p} = \sum_{l=1}^{R} 2(I - u^{l^T} u^l)(p - p_0^l) = 0 \quad (12)$$

$$\Leftrightarrow \sum_{l=1}^{R} (I - u^{l^T} u^l) p = \sum_{l=1}^{R} (I - u^{l^T} u^l) p_0^l$$

Thus, $$\hat{p} = \left(\sum_{l=1}^{R} (I - u^{l^T} u^l)\right)^{\dagger} \sum_{l=1}^{R} (I - u^{l^T} u^l) p_0^l, \quad (13)$$

where † is the Moore-Penrose pseudo-inverse. An exemplary method for estimating the smallest set of multiple R rays that excludes a substantial proportion of outliers may include some or all the following steps: (1) randomly select two rays to find an initial point $p_s$ with the shortest distance between them; (2) compute the distance between $p_s$ and each ray $r_l$ in $r_R$; (3) count the number of rays, $\tau_{current}$, fit with a predefined tolerance ϵ to observe inliers with the allowable distance from $p_s$ and $r_l$; (4) update the closest point $p_{closest} = p_s$ and the maximum number of rays, $\tau_{max} = \tau_{current}$, if $\tau_{max} < \tau_{current}$, (5) repeat steps 1 through 5 until the maximum number of iterations is reached; and, (7) estimate $\hat{p}$ in the equation (13) with all the identified inliers for which the distance between the closest point $p_{closest}$ and a ray $r_l$ is less than E.

The instant disclosure also provides a solution to the absolute orientation problem when aligning two different coordinate systems in the context of using an AR system. The two different coordinate systems refer to the real-world coordinate system and the virtual or augmented world coordinate system. The following exemplary process may be used to solve the absolution orientation problem between the aligned reference points in the virtual-world coordinate system and the corresponding predefined reference points in the real-world coordinate system.

A rigid transformation between two points $p_1$ and $p_2$ in three dimensions that position different coordinate systems can be defined as $p_2 = Rp_1 + p_0$ where R is a 3×3 orthonormal matrix for rotation and $P_0$ is a vector for translation. In consideration of $p_M = (x_M, y_M, z_M)$ and $p_\alpha = (x_\alpha, y_\alpha, z_\alpha)$ that denote the coordinate of the aligned reference point in virtual-world coordinates and the coordinates of the predefined point in real-world coordinates, respectively, the input of the absolute orientation problem can be referred to as a set of conjugate pairs $\{(p_{M,1}, p_{\alpha,1}), \ldots, (p_{M,n}, p_{\alpha,n})\}$. To solve the absolute orientation problem, the rigid transformation matrix between points $p_M$ and $p_\alpha$ can be refined by using R and t in the equation (14) as follows:

$$x_\alpha = r_{xx}x_{\hat{M}} + r_{yy}y_{\hat{M}} + r_{xz}z_{\hat{M}} + t_x$$

$$y_\alpha = r_{yx}x_{\hat{M}} + r_{yy}y_{\hat{M}} + r_{yz}z_{\hat{M}} + t_y$$

$$z_\alpha = r_{zx}x_{\hat{M}} + r_{zy}y_{\hat{M}} + r_{zz}z_{\hat{M}} + t_z \qquad (14)$$

where there are 12 unknown parameters (i.e., the 9 elements of the rotation matrix and the 3 elements of the translation matrix). Since each conjugate pair produces three equations, four conjugate pairs are at least required to find the 12 unknowns. More than four conjugated pairs may be employed to perform the better accuracy of the result in this embodiment. In a simple matrix form, the rigid transformation that converts the coordinates of each point in virtual-world coordinates to real-world coordinates can be defined as:

$$P_{\alpha,i} = R(q)p_{\hat{M},i} + p_{\hat{M}} \qquad (15)$$

where $R(q)$ denotes the rotation matrix with respect to a unit quaternion $q$ and $p_{\hat{M}}$ is the location of the origin of the aligned reference point in the world coordinate system. The unit quaternion $q$ is a vector defined as $q = [q_0, q_1, q_2, q_3]^T$ for $q_0^2 + q_1^2 + q_2^2 + q_3^2 = 1$. Given two sets of points $P_{\hat{M}} = \{p_{\hat{M},1}, p_{\hat{M},2}, \ldots, p_{\hat{M},n}\}$ and $P_\alpha = \{p_{\alpha,1}, p_{\alpha,2}, \ldots, p_{\alpha,n}\}$ in the aligned references in the virtual-world coordinates and the corresponding pre-defined references in the real-world coordinates, respectively, the absolute orientation problem is to align these two sets of points in space as illustrated in FIG. 10. The centroid of the point clouds with respect to $P_{\hat{M}}$ and $P_\alpha$ is first computed as:

$$\bar{p}_\alpha = \frac{1}{n}\sum_{i=1}^{n} p_{\alpha,i}, \quad \bar{p}_{\hat{M}} = \frac{1}{n}\sum_{i=1}^{n} p_{\hat{M},i} \qquad (16)$$

And then, each point is subtracted from the centroid:

$$r_{\alpha,i} = p_{\alpha,i} - \bar{p}_\alpha, \; r_{\hat{M},i} = p_{\hat{M},i} - \bar{p}_{\hat{M}}. \qquad (17)$$

The problem in determining the rotation is related to align the two sets of rays with respect to the centroids in ray coordinates where the rays are derived from the set of conjugate pairs. Approximated is the best alignment in a least-squares sense by computing the rotation $R(q)$ to be maximal to the scalar product of each ray pair:

$$\eta^2 = \sum_{i=1}^{n} r_{\alpha,i} \cdot R(q) r_{\hat{M},i}. \qquad (18)$$

Using the quaternion notation, the equation (18) can be represented as:

$$\sum_{i=1}^{n} r_{\alpha,i} \cdot q r_{\hat{M},i} q^* = \sum_{i=1}^{n} (q r_{\hat{M},i})(q r_{\alpha,i}). \qquad (19)$$

Because the equation (19) can be refined using the notation of a quadratic form:

$$\sum_{i=1}^{n} (q r_{\hat{M},i}) \cdot (r_{\alpha,i} q) = \sum_{i=1}^{n} (N_{\hat{M},i} q)^T \cdot (N_{\alpha,i} q) \qquad (20)$$

$$= \sum_{i=1}^{n} q^T N_{\hat{M},i}^T N_{\alpha,i} q$$

$$= q^T \left(\sum_{i=1}^{n} N_{\hat{M},i}^T N_{\alpha,i}\right) q$$

$$= q^T \left(\sum_{i=1}^{n} N_i\right) q$$

$$= q^T N q$$

where $q$ is a column vector. Using the eigenvector with respect to the most positive eigenvalue, the unit quaternion can be maximized in this quadratic form. Given $r_{\hat{M},i} = (x_{\hat{M},i}, y_{\hat{M},i}, z_{\hat{M},i})$ and $r_{\alpha,i} = (x_{\alpha,i}, y_{\alpha,i}, z_{\alpha,i})$, the matrices $N_{\hat{M},i}$ and $N_{\alpha,i}$ are given by:

$$N_{\hat{M},i} = \begin{bmatrix} 0 & -x_{\hat{M},i} & -y_{\hat{M},i} & -z_{\hat{M},i} \\ x_{\hat{M},i} & 0 & z_{\hat{M},i} & -y_{\hat{M},i} \\ y_{\hat{M},i} & -z_{\hat{M},i} & 0 & x_{\hat{M},i} \\ z_{\hat{M},i} & y_{\hat{M},i} & -x_{\hat{M},i} & 0 \end{bmatrix} \qquad (21)$$

$$N_{\alpha,i} = \begin{bmatrix} 0 & -x_{\alpha,i} & -y_{\alpha,i} & -z_{\alpha,i} \\ x_{\alpha,i} & 0 & z_{\alpha,i} & -y_{\alpha,i} \\ y_{\alpha,i} & -z_{\alpha,i} & 0 & x_{\alpha,i} \\ z_{\alpha,i} & y_{\alpha,i} & -x_{\alpha,i} & 0 \end{bmatrix}. \qquad (22)$$

To simplify the matrix N, the sum over all conjugate pairs of the product of coordinates k and l in the aligned point and in the corresponding predefined point, respectively, may be defined as:

$$\alpha_{kl} = \sum_{i=1}^{n} k_{\hat{M},i} l_{\alpha,i}. \qquad (23)$$

Using $\alpha_{kl}$, the matrix N is given by:

$$N = \begin{bmatrix} \alpha_{xx} + \alpha_{yy} + \alpha_{zz} & \alpha_{yz} - \alpha_{zy} & \alpha_{zx} - \alpha_{xz} & \alpha_{xy} - \alpha_{yx} \\ \alpha_{yz} - \alpha_{zy} & \alpha_{xx} - \alpha_{yy} - \alpha_{zz} & \alpha_{xy} + \alpha_{yx} & \alpha_{zx} + \alpha_{xz} \\ \alpha_{zx} - \alpha_{xz} & \alpha_{xy} + \alpha_{yx} & -\alpha_{xx} + \alpha_{yy} - \alpha_{zz} & \alpha_{yz} + \alpha_{zy} \\ \alpha_{xy} - \alpha_{yx} & \alpha_{zx} + \alpha_{xz} & \alpha_{yz} + \alpha_{zy} & -\alpha_{xx} - \alpha_{yy} + \alpha_{zz} \end{bmatrix}. \qquad (24)$$

These calculations result in the unit quaternion to indicate the rotation that aligns the ray bundles. From the elements of the unit quaternion, a rotation matrix can be found as follows:

$$R(q) = \begin{bmatrix} q_0^2 + q_1^2 - q_2^2 - q_3^2 & 2(q_1 q_3 - q_0 q_3) & 2(q_1 q_3 + q_0 q_2) \\ 2(q_1 q_2 + q_0 q_3) & q_0^2 + q_2^2 - q_1^2 - q_3^2 & 2(q_2 q_3 - q_0 q_1) \\ 2(q_1 q_3 - q_0 q_2) & 2(q_2 q_3 - q_0 q_1) & q_0^2 + q_3^2 - q_1^2 - q_2^2 \end{bmatrix} \quad (25)$$

Once the rotation is determined, the translation part of the transformation in the equation (15) can be given by:

$$p_{\hat{M}} = \bar{p}_\alpha - R(q)\bar{p}_{\hat{M}}. \quad (26)$$

Figure 18:
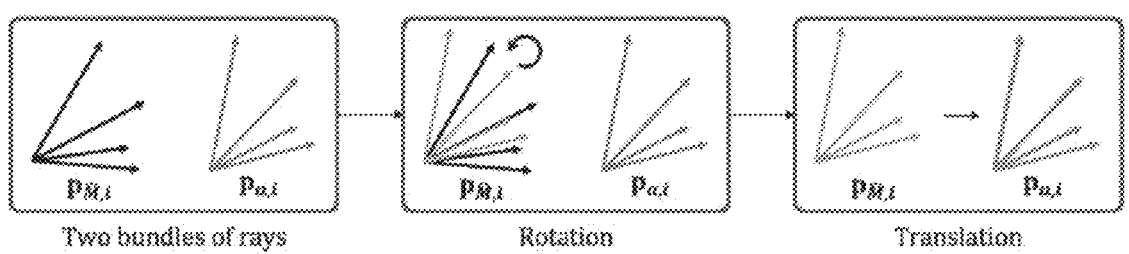
FIG. 18 is a diagram depicting aligning two different coordinate systems using two sets of rays in an absolute orientation problem.

Referring to FIG. 18, an example of aligning two different coordinate systems using two sets of rays in absolute orientation is depicted. For example, given two sets of points P_M^={p_(M^,1), p_(M^,2), ... , p_(M^,n)} and P_a={p_(a,1), p_(a,2), ... , p_(a,n)} in the aligned references in the virtual world coordinates and the corresponding predefined references in the real-world coordinates, respectively, the problem in determining the rotation is related to aligning the two sets of rays with respect to the centroids in ray coordinates where the rays are derived from the set of conjugate pairs {(p_(M^,1), p_(a,1)), ... , (p_(M^,n), p_(a,n))}. Approximated is the best alignment in a least-squares sense by computing the rotation to be maximal to the scalar product of each ray pair. Once the rotation is determined, the translation part of the transformation can be estimated by computing the location of the origin of the aligned reference point in the world coordinate system.

Figure 19:
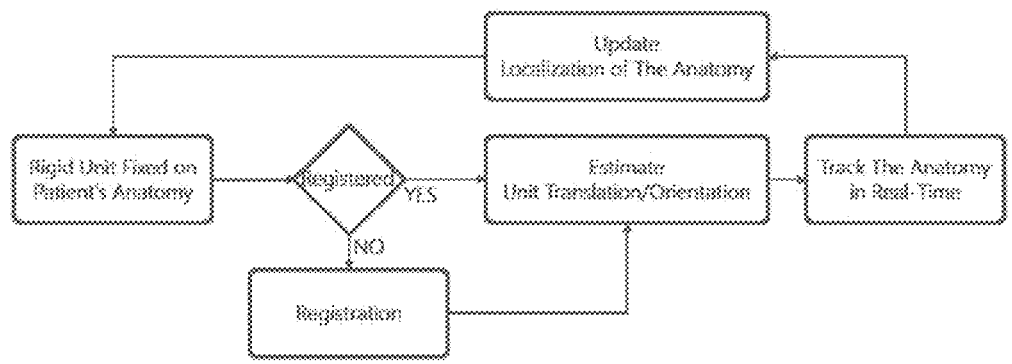
FIG. 19 is a block diagram of an exemplary process to track a bone based on UWB and IMU hybrid tracking system in real-time.

Turning to FIG. 19, a block diagram of one exemplary process to track a bone using an UWB and IMU hybrid tracking system in real-time is depicted. A patient may be tagged with multiple "units" fixed on the patient's anatomy. The embodiment may first register the units from the external tracking system to the virtual-world coordinate system where the coordinates of the units for the external tracking system are predefined. In the virtual-world coordinate system, computer-generated models or images are rendered and superimposed on top of the patient's anatomy via a display device (e.g., a projector, a heads-up display, etc.). Post registration, the external tracking system may continuously estimate and track the position and orientation of the units in real-time and send the estimated coordinates of the target units to a software application of the system, which updates and renders the augmented information along with the coordinates of the target units.

FIG. 20 depicts an exemplary user device of an AR system in accordance with the instant disclosure. By way of example, the user device may comprise a surgical helmet 401 having an integral camera 402 and heads-up display depicted on a visor 403. The exemplary user device also includes an IMU unit 404 mounted to the crown of the helmet and a series of UWB units 405. Though not shown, an on-board battery is included in order to power the camera, UWB units, IMU unit, and heads-up display.

FIG. 21 depicts an alternate exemplary structure to that may be used as part of the exemplary AR system. More specifically, the structure includes a plurality of laser projectors that are associated with a color camera. Each camera and laser projector are also associated with an IMU unit and an UWB unit. Using the information from the IMU and UWB units, the AR system knows the relative positions of the camera and the laser projector and updates the image displayed by the laser projector taking into account the position of the laser projector and IMU and UWB units mounted to the patient anatomy.

FIG. 22 depicts an exemplary structure that incorporates the IMU and UWB units 601 along with a camera 602. In this fashion, the structure of FIG. 22 allows for integration of optical tracking into positioning algorithms. This integration may help refine precision, detect undesirable motion of anchors, and speed up positioning algorithms. In FIG. 22, reference number 603 indicates UWB Antennas Constellations.

Figure 23:
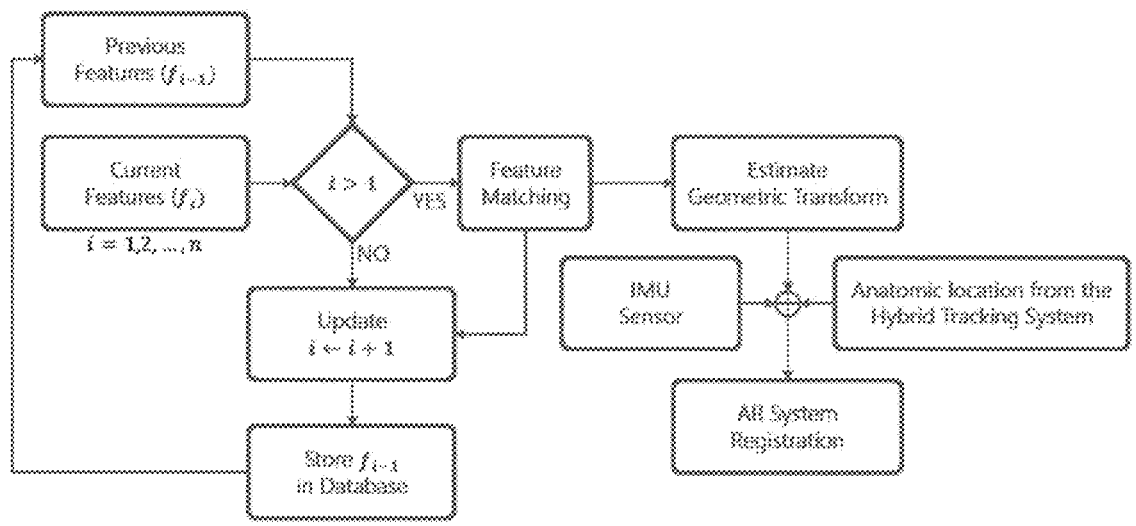
FIG. 23 is a block diagram of an exemplary process to register the head-mounted augmented reality system integrating the feature correspondence approach and the hybrid tracking system.

Referring to FIG. 23, a block diagram is provided of an exemplary process to register the head-mounted AR system integrating the feature correspondence approach and the hybrid tracking system. In this exemplary process, features can be denoted as corners, curves, lines, edges, or regions on a target image. From the feature matching, the correspondences between the set of features in both previous and current images can be established to estimate the homography or geometric transform. If at least four correspondences in the image plane are found, the homography can be estimated through the linear equations. To improve the accuracy of high precision registration, as well as tracking a moving user and the patient's anatomy in real-time processing, IMU units and UWB units are integrated into the head-mounted AR system to view augmented information in the display device.

Figure 24:
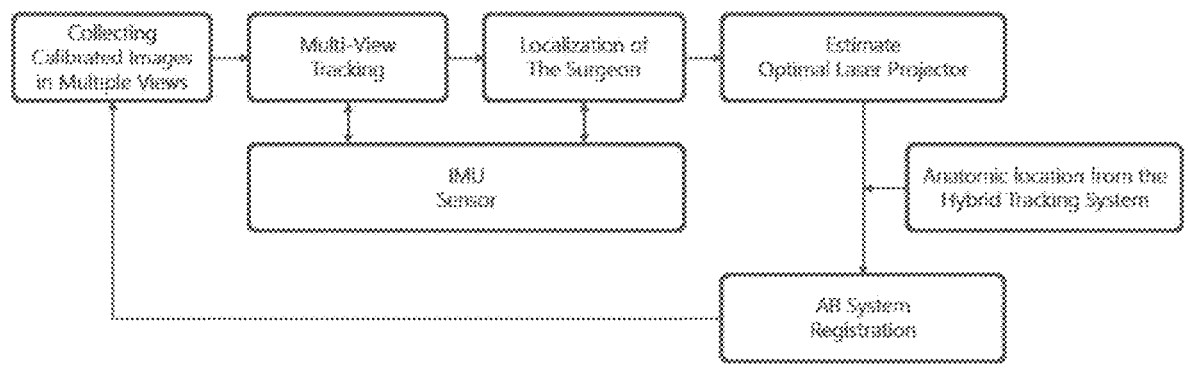
FIG. 24 is a block diagram of an exemplary process to register the laser projector-based AR system.

Referencing FIG. 24, a block diagram is provided of an exemplary process to register a laser projector-based AR system. To calibrate each camera, a known structure having many individual and identifiable points may be used. By viewing this structure from different angles, the relative location and orientation of the camera for each image as well as the intrinsics of the camera can be computed. Post finding camera parameters of the intrinsics, a robust multi-view tracking approach with multiple cameras may be performed to provide robustness against occlusion. Tracking a moving target in an operating room covered by calibrated multiple cameras with overlapping fields of view can be established by finding the correspondence between different cameras. To this end, the exemplary process for tracking a moving target may employ a target tracker including a marker detection, feature correspondence, 3D model-based object detection, hybrid tracking system, or on combination thereof. With the combination of the target tracker and the hybrid tracking system, the location of the patient's anatomy may be provided by the hybrid tracking system using IMU and UWB technologies. The solution to the potential problem in resolution can be found by localizing the surgeon movement and by seeking the optimal laser projector among multiple laser projectors placed around the operating room.

Figure 25:
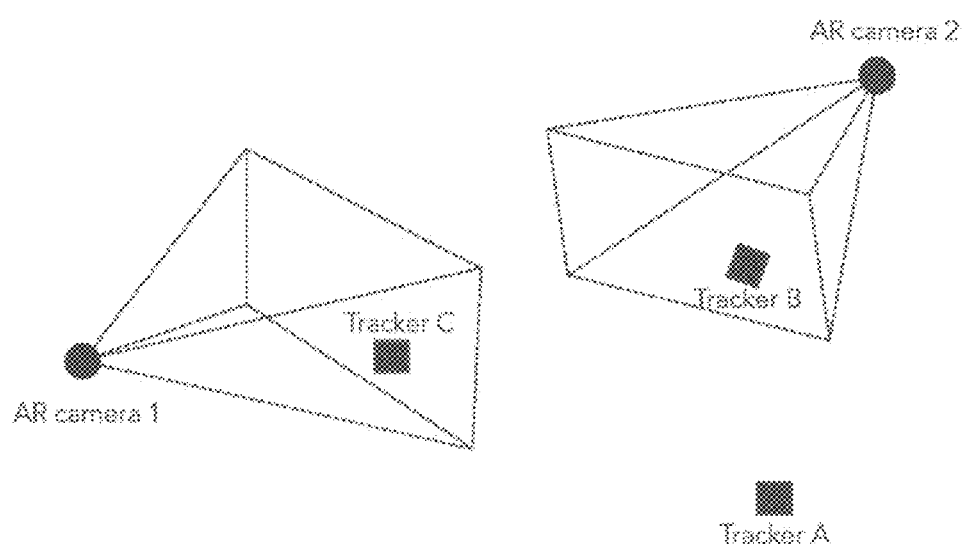
FIG. 25 is a diagram demonstrating an integration of the augmented reality system with the UWB/IMU systems.

Turning to FIG. 25, an exemplary integration of the AR system with the UWB/IMU systems is graphically depicted. The AR cameras may consist of a computer vision tracking system, where the viewing volume is indicated by the dotted lines. The AR cameras may include at least one of an UWB unit and an IMU unit (identified in FIG. 25 as a "Tracker") to allow for knowing the location and orientation of AR camera and likewise having this location and orientation registered to a global coordinate. The AR camera 1, in this illustration, will be able to track Tracker C within its viewing volume. Tracker C can also transmit its positions and orientations to the AR system, where a sensor fusion algorithm may be used along with the AR vision tracking system to improve the tracking accuracy. Tracker B is within the tracking volume of AR camera 2 but not visible to AR camera 1. AR camera 2 may track Tracker B positions and orientations and wirelessly transmit the data to AR camera 1. Alternatively, Tracker B may send its locations and orientations directly to AR camera 1. Tracker A may be tracked even though it is placed outside of both AR cameras' viewing volumes. Tracker A's positions and orientations are tracked by both its own UWB and IMU units, and its position and orientation data may be sent to both of the AR cameras. It is understood that the AR system may have limitations on tracking multiple objects within its viewing volume, so the positioning system may use the UWB/IMU tracker instead. The use of UWB/IMU units/trackers may reduce the computation load required for computer vision of the AR system, thus relieving computation burden and improving the performance of the AR system.

While the AR system may communicate with the trackers locally, as part of a helmet where the AR system is local to the helmet, it is also within the scope of the disclosure to have the AR CPU running the AR software application located remotely from the trackers. In such a case, the AR system needs to communicate to the trackers via a wired or wireless network (or combination of wired and wireless networks). In exemplary form, the AR software application runs on a server communicatively coupled to the trackers through a private network. The wireless trackers should be suitable for governing a protocol between the server and the AR application. An exemplary method for the protocols may provide all the following functions or parts for efficiently handling errors during data transmission via network: (1) data sequencing; (2) data routing; (3) flow control; and, (4) error control. Once the tracker is configured to connect to the server running the AR application that creates three-dimensional models of virtual objects on the display, the server may continuously feed position and orientation data from the trackers to the AR application. By way of example, the trackers may continuously and simultaneously track multiple external surgical tools associated with one or more surgical procedures, as well as a user, and patient anatomy. Using the estimated coordinates of the tracked target and the transformation in equation (15), the AR application renders the three-dimensional virtual model to be superimposed into the corresponding real-world image viewable by a user.

As mentioned previously, the trackers may track the motion of a user (e.g., surgeon) of the AR system. In exemplary form, the trackers may include one or more of the following: IMU sensors, UWB sensors, depth measuring sensors (e.g., a range camera, binocular stereo camera, or time-of-flight camera), imaging sensors, relative measuring sensors (e.g., a three-axis gyroscope, accelerometer, and magnetometer), or any combination thereof. As discussed previously, the ability to accurately track the motion of the user wearing an AR vision system is crucial to ensure that the virtual images displayed correctly align to the real-world images the user sees. By way of example, the exemplary AR system may be incorporated as part of a helmet having an optical see-through display or may be incorporated as part of a mobile device screen within the field of view (FOV) of a user. Highly accurate registration of the AR system may be accomplished by appropriately tracking the user's relative movement preferably with six degrees of freedom (DOF): (1) three variables (x, y, and z) for position, and (2) three angles (yaw, pitch, and roll) for orientation.

As discussed previously, the AR system is operative to display virtual images on top of real-world images. As one might imagine, the utility of the virtual images is premised upon registering the virtual images to the real-world images. By way of example, the virtual images may comprise one or more images of a patient's bone(s). Accordingly, the following discussion involves registration of the virtual patient bone models to real patient bones.

Figure 4:
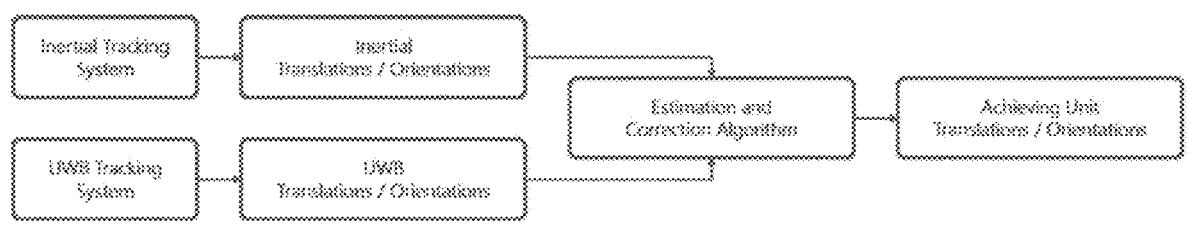
FIG. 4 is a block diagram for the processing and fusion algorithm of the UWB and IMU systems.

Each object to be tracked may be integrated with an external tracking system (tracker) based on IMU and UWB technologies (See FIGS. 2-4 and the foregoing discussion concerning these figures), which is rigidly fixed to the object. To register the virtual bone models to the real patient bones, the following approaches may be performed: (1) the mixture of IMU and UWB technologies can be used to "paint" (select a plurality of points on the surface of the real bone) and register the selected points to the virtual bone models that are reconstructed from the medical images; (2) a patient specific registration device can be used to perform the registration where the orientation of the device relative to the patient anatomy is known; and, (3) the specific reference landmarks can be selected which correspond to landmarks on the virtual bone models.

Once the virtual bone models are registered by using the external tracking system to the real patient bone, the head-mounted AR system in FIG. 20 can be registered by combining the anatomic location estimated by the hybrid tracking system with its sensors such as IMU, UWB, depth, and imaging sensors. To precisely register the AR system into the real-world view, a target tracker (e.g., a marker detection, feature correspondence, 3D model-based object detection, or on combination thereof) with a single camera and IMU sensor may be used to determine the position and orientation of a surgeon in the operating room as well as to identify the target. Target tracker-based registration described herein may be replaced with the hybrid tracking system integrated or built into the head-mounted or hand-held (or body-attached) system directly.

In another exemplary embodiment of the AR system without a head-mounted or hand-held display device, which may consist of multiple cameras, laser projectors, and IMU and UWB technologies as shown in FIG. 21, a simultaneous multi-view tracking approach may be performed to handle poor illumination, static or moving ambient light sources, or occlusions under unconstrained indoor environments. There may be two reasons for facilitating multiple cameras: (a) one camera is limited to provide adequate coverage of the target environment due to limited field of view; and, (b) multiple cameras can provide robustness against occlusion. The multi-view tracking approach described herein may be applied in position and orientation estimation and identification of a target object to superimpose virtual guides/ images on top of real patient bones in the operating room along with the real-world view of the user. The issue of consistently and accurately tracking a moving target in an operating room covered by calibrated multiple cameras with overlapping fields of view can be addressed by establishing correspondence between trackers of the same object in different cameras. The correspondence can be to recover preferential information of the target object. To find the correspondences between different cameras, one may employ a target tracker described herein including marker detection, feature correspondence, 3D model-based object detection, external tracking system, or a combination thereof. Accordingly, the potential problem in occlusion can be solved by localizing the surgeon movement in real-time and by seeking the optimal laser projector among multiple laser projectors, which are placed around the operating room.

After the considered AR systems are registered, the rendering module combines the input image taken from the camera sensor in the AR system and the virtual guide using the estimated pose and then, renders the augmented image on the display. Next, all resections relevant to the surgical procedure are visually assisted by overlaying the proposed cutting location and orientation on the anatomy. Additionally, the surgical instrument used for the cutting can be tracked and the true orientation and location of the cut is updated in the AR overlay in real-time.

During the surgery, the ability to track the patient's anatomic location and the surgeon movement from many different sensors in the hybrid tracking system and the AR system can be fed back into localization of the virtual guide to precisely overlay the virtual scene to the viewpoint of the surgeon. In addition, to account for the potential registration errors caused by occlusion and tracking failures in the AR system, the trackers (e.g., the IMU and/or UWB units) mounted on the patient bone may be used to track the patient's anatomic location and a central unit as global reference in the hybrid tracking system. The software of the tracking application running on a CPU of the AR system may wirelessly communicate with trackers/units via private network updates so that the trackers provide data identifying the location of the user/surgeon in real-time.

After completing the necessary cuts as part of an exemplary surgical procedure, for example, one may use the AR system to assess intra-operative kinematics in the following aspects: (1) range of motions; (2) laxity (implant translations) at extension and flexion; (3) ligament distances; and, (4) any other clinically relevant kinematic information. The evaluation of intra-operative kinematics via the AR system can be simulated as follows: (1) by registering the cutting instruments to the hybrid tracking system prior to the surgery once and then, by tracking the instruments to estimate the location and orientation of the cuts during surgery; (2) by using an object recognition approach in conjunction with the trackers/units mounted on the patient's anatomy in order to precisely superimpose the virtual implants into the resected bone after estimating the geometric transform of the embedded patient's implants during the surgery; and, (3) by assuming cuts performed as planned. For the evaluation of post-operative kinematics, one may employ IMU and UWB technologies to track body motion and analyze muscle activation. The AR system techniques combined with the hybrid tracking system can also allow visualization of post-operative kinematics at the point of care.

Figure 26:
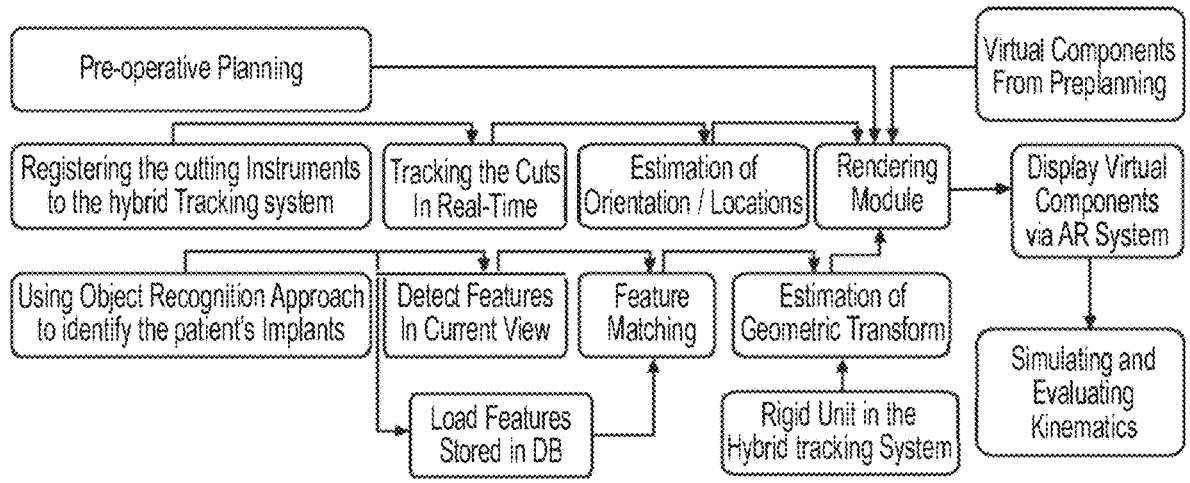
FIG. 26 is a block diagram of an exemplary process to simulate and evaluate intra-operative kinematics.

Shifting to FIG. 26, a block diagram is depicted of an exemplary process to simulate and evaluate intra-operative kinematics. This example process presumes that the cuts as planned for joint replacement are properly performed in an operating room. Multiple units designed for the hybrid tracking system may be rigidly fixed on any location of the patient's anatomy. To track locations and orientations of surgical tools such as cutting instruments in real-time processing, multiple sensors that wirelessly communicate to the hybrid tracking system are mounted onto the target tools. The foregoing exemplary process for detecting and localizing untextured objects using a 3D model may be used to track and identify the patient's implants that are commonly made of metals. In this process, features should be denoted as lines or edges. All the edge templates and set of sample rater points to be loaded in the step of feature matching may be embedded or stored as a text or table file in a server, computer, smartphone, or tablet. Post estimating the poses of all the targets including cutting instruments, patient's implants, and patient's anatomy, rendering of virtual models of the corresponding targets as well as the cuts combined with virtual components configured from preplanning may perform to view augmented information on the display device in the augmented reality system is undertaken. The foregoing process may simulate and evaluate intra- and post-operative kinematics via the augmented reality modules.

Figure 27:
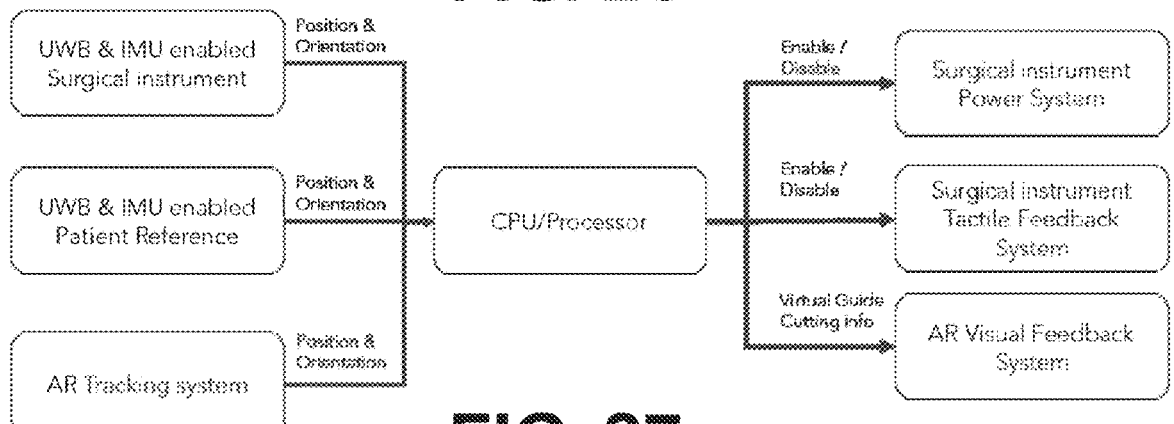
FIG. 27 is a block diagram of an exemplary process to provide feedback to the surgical tool.

Referencing FIG. 27, a block diagram is depicted of an exemplary process to provide feedback to the surgical tool as part of surgical navigation in accordance with the instant disclosure. By way of example, a CPU/Processor collects positions and orientations data from an UWB & IMU enabled surgical instrument. The integration of IMU, UWB and AR systems is accomplished using software application program interfaces that are designed to translate the messages from each system into a format readable by the processor. Processing results may be communicated back to each system in the framework using the same software tools to translate the processor information into readable format for each system. The position of the patient may be tracked via UWB & IMU units/trackers that are rigidly attached to the patient's bone or AR's vision system. The feedback to the surgical tool may be implemented as allowing or forbidding the battery to be connected to the electronics of the surgical tool. Alternatively, or in addition, the feedback may be implemented as enabling a tactile feedback (e.g. haptic motor creating a tumbling feel, as discussed previously). The feedback may also be implemented as warning messages displayed on a visual element in the AR helmet or surgical instrument.

Figure 28:
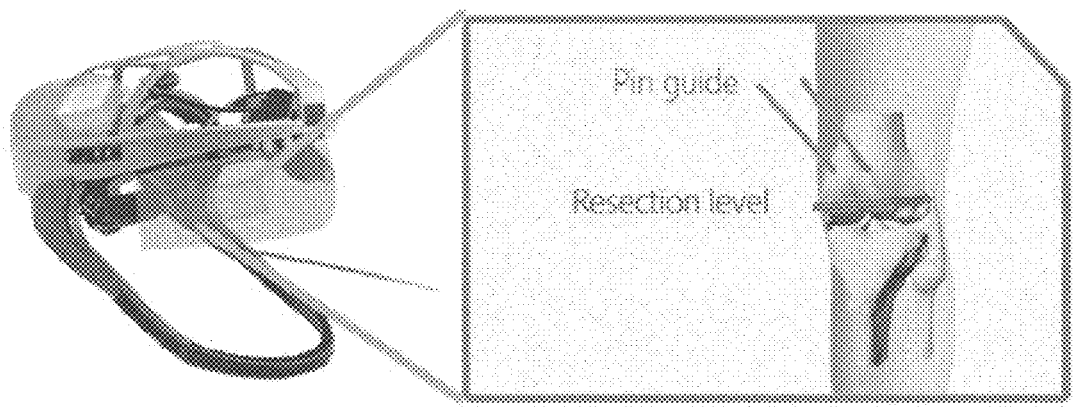
FIG. 28 is an illustration of the augmented reality system placing virtual bone and virtual components (e.g. pin guide locations) over a real world image of the exterior of a lower leg.

Moving on to FIG. 28, an exemplary illustration of a user wearable device of the AR system is depicted. The user wearable device includes a graphical projector operative to placing virtual bone images and virtual components (e.g. pin guide locations) onto the real world anatomy of a patient. The user wearable device can also display the projected resection level and the virtual placement of the implant onto the real-world anatomy of the patient.

Figure 29:
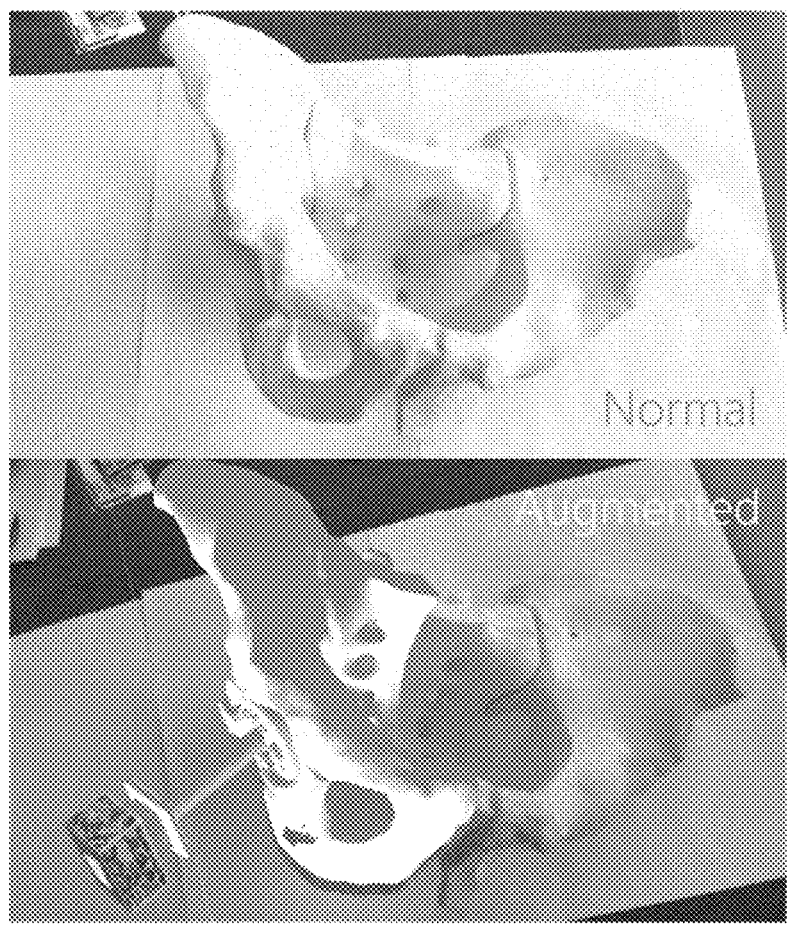
FIG. 29 is a pair of pictures showing a normal real world view, as well as an augmented reality view using a custom reference device to register the augmented system with the patient space.

FIG. 29 depicts a real-world view of a tangible patient bone model of a pelvis (denoted as "Normal") and a second view showing the AR system of the instant disclosure projecting a virtual image upon the bone model. As can be seen, the AR system aligns the images to the tangible bone model and includes an image of a virtual reamer shown reaming the acetabular cup consistent with a pre-operative surgical plan.

Figure 30:
FIG. 30 is a picture depicting transfer of anatomical tracking from custom registration device to rigidly fixed marker for augmented reality surgical navigation.

FIG. 30 is a photograph depicting the transfer of anatomical tracking from a custom registration device to rigidly fixed marker for AR surgical navigation.

Figure 31:
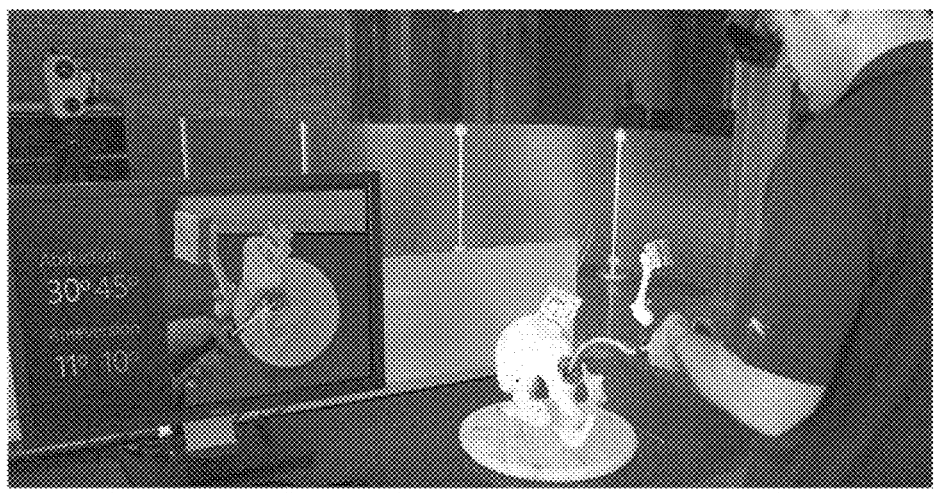
FIG. 31 is a picture depicting tracking of surgical instrument relative to anatomy using augmented reality for hip cup positioning.

Referring to FIG. 31, a photograph depicts tracking of a surgical instrument relative to anatomy using AR for hip cup positioning. In this exemplary photograph, visual feedback is provided on the computer screen monitor adjacent a tangible pelvis model, as well as directly to a user via an AR heads-up display as part of an AR helmet.

Figure 32:
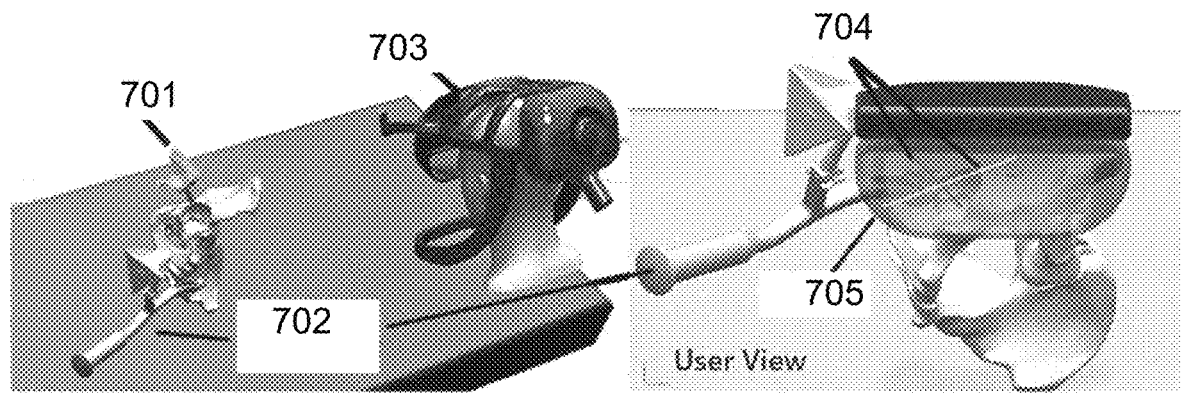
FIG. 32 is a representation of what user will see through an augmented view of the hip navigation and correct orientation.

Referencing FIG. 32, a dual image representation depicting on the left-hand side the relative position of a user of the AR system in accordance with the instant disclose in the context of a total hip replacement surgical procedure. In the right-hand representation, is what the user would see via the heads-up display on the visor of the AR helmet depicted in the left-hand side representation. In this exemplary depiction, a surgeon is performing a total hip arthroplasty using the UWB and IMU units along with the AR system. The UWB/IMU stylus 701 is a tool that allows the surgeon to register the patient's bone to the rest of the applicable tracking system. As discussed previously, the surgeon may paint the bone surface or pick specific anatomical landmarks with the stylus. The UWB/IMU surgical instrument 702 represents the surgical instrument that is enabled by the UWB/IMU units, where the position and orientation are known to the surgical navigation and guidance software. The AR helmet 703 can assist the localization and improve accuracy of the tracking system, and it can also relay information to the surgeon by overlaying virtual objects 704 on to real-world images via the AR helmet visor 705.

Figure 33:
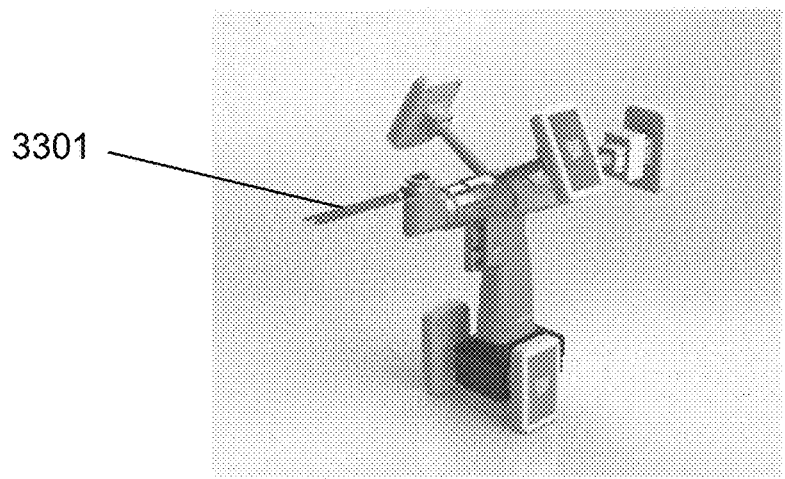
FIG. 33 is an exemplary oscillating saw instrumented with UWB tracking and IMU tracking capabilities.

FIG. 33 depicts a surgical oscillating saw 3301 instrumented with UWB tracking and IMU tracking units.

Figure 34:
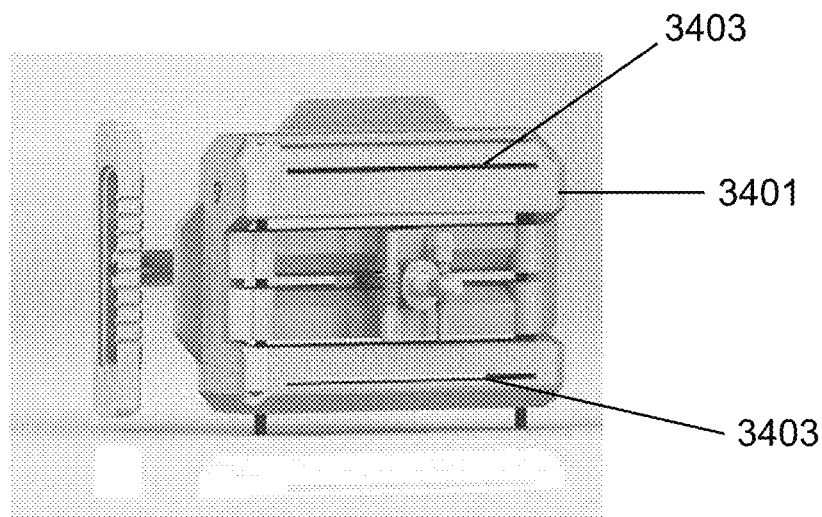
FIG. 34 is a mechanically adjustable 4-in-1 cutting block that can be utilized for multiple sizes and implant families.

FIG. 34 depicts a mechanically adjustable 4-in-1 cutting block 3401 (physical embodiment) that can be utilized for multiple sizes and implant families in accordance with the instant disclosure. The mechanical aspects of this cutting guide may be combined with the programmable and tracked aspects of the cutting block in FIG. 35. By way of example, the cutting slots 3403 in this cutting block may remain closed until such time that the slot 3403 is in the correct position as determined by a pre-operative plan via the data output from UWB tracking and IMU tracking units mounted to the cutting guide. Alternatively, the slots 3403 may be manually opened and closed.

Figure 35:
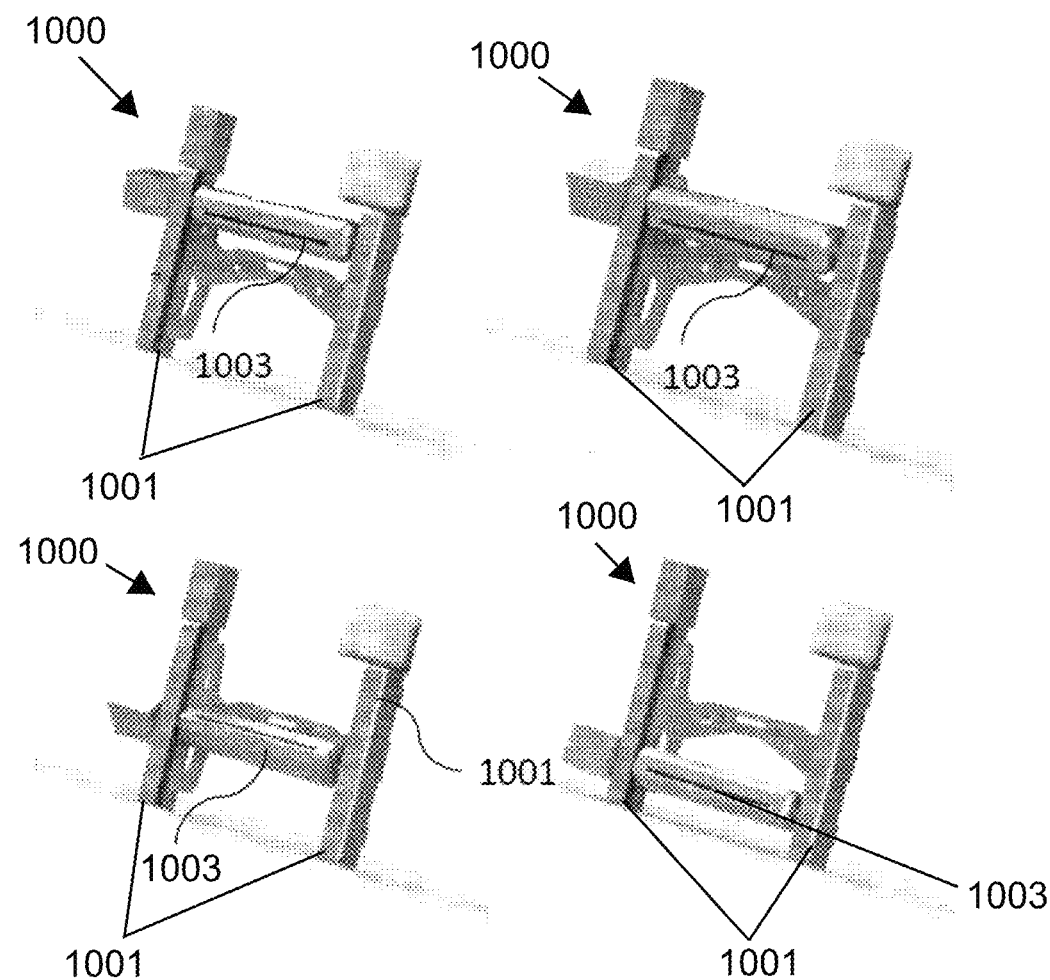
FIG. 35 is an adjustable "smart" cutting block for performing femoral resections in total knee replacement.

Turning to FIG. 35, an adjustable "smart" cutting block for performing femoral resections in total knee replacement is depicted. The cutting block is designed so that the four (or more) positions of the cutting block are dictated by a motorized system to translate along the two rails 1001, as well as rotate to match orientation of posterior, anterior and chamfer cuts. The instrument is wirelessly programmable through UWB, BLE, BlueTooth, or other communication protocols so that the size of the implant is stored on the device and the positions of the cutting slots 1003 are dictated by the cutting box of the implant size. Initial placement of the device can be performed using custom instrumentation or through the use of so-called virtual guides. In an alternate exemplary embodiment, the motors for moving the cutting slot can be moved off of the hardware and performed via attachment, by an outside motor or by a standard surgical driver. While the exemplary cutting block is illustrated to show at least four cutting positions, the actual positions of the cutting slot may be patient specific and consist of any number cuts. The programmable aspect of the "smart" block allows for the customization of the stopping positions, so that each stopping position is dictated by a defined cutting plane.

Figure 36:
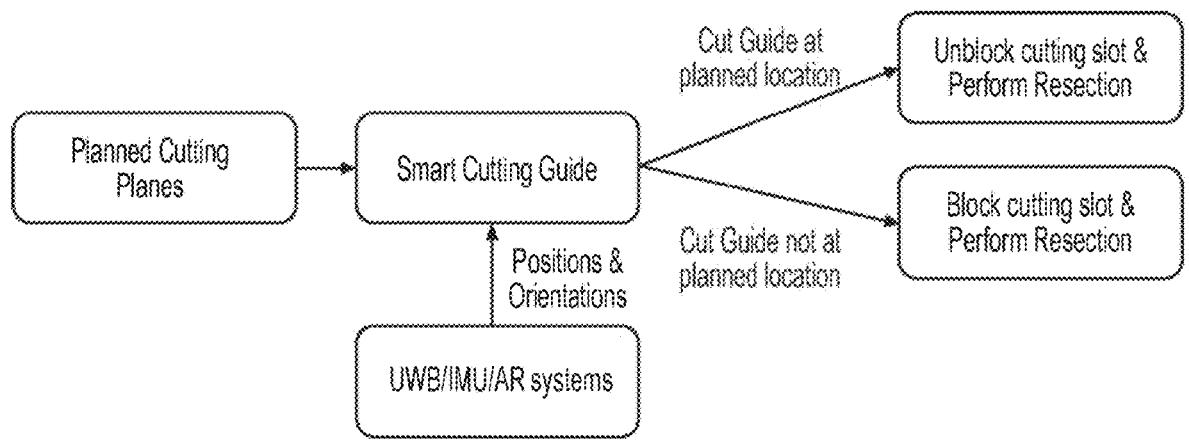
FIG. 36 is a flowchart showing an exemplary creation and usage process for a smart cutting guide, where the smart cutting guide may be actively tracked by UWB/IMU/AR systems, and the cutting guide may be pre-programmed or wirelessly receive planned cutting planes locations.

Referring to FIG. 36, an exemplary flowchart depicts a process for utilizing the smart cutting guide 1000 of FIG. 35, where the smart cutting guide 1000 may be actively tracked by UWB/IMU/AR systems. In exemplary form, the cutting guide may be pre-programmed or wirelessly receive planned cutting planes locations generated as part of pre-operative plan using virtual models of the patient's actual anatomy. The cutting guide, which may be actively tracked by UWB/IMU/AR systems, and in this way automatically opens and closes the cutting slot 1003 so that a cutting blade can pass through the slot 1003 only if the guide 1000 in the correct position and orientation for a bone cut.

Figure 37:
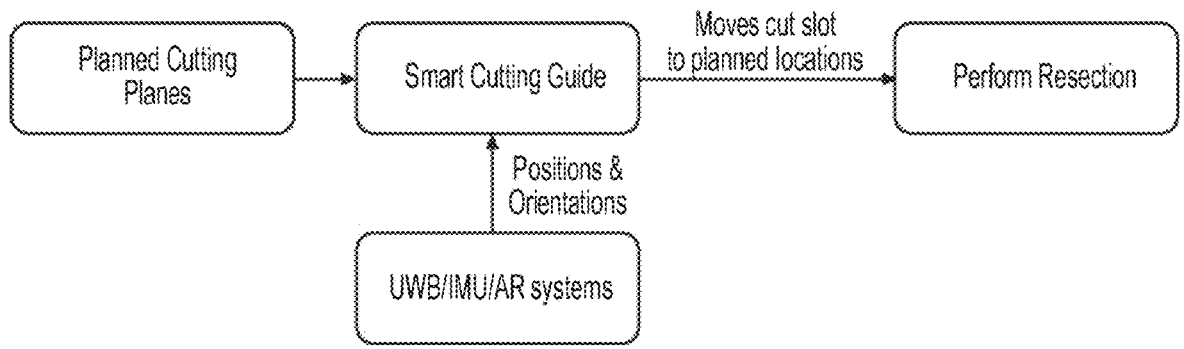
FIG. 37 is a flowchart showing an further exemplary creation and usage process or a smart cutting guide, where the smart cutting guide may be actively tracked by UWB/IMU/AR systems, and the cutting guide may be pre-programmed or wirelessly receive planned cutting planes locations.

FIG. 37 depicts an alternate exemplary flowchart for a process of utilizing the smart cutting guide 1000 of FIG. 35, where the smart cutting guide may be actively tracked by UWB/IMU/AR systems. In exemplary form, the cutting guide may be pre-programmed or wirelessly receive planned cutting planes locations generated as part of pre-operative plan using virtual models of the patient's actual anatomy. The cutting guide, which may be actively tracked by UWB/IMU/AR systems, is operative to automatically reposition the cutting block 1002 and to open and close the cutting slot 1003. By way of example, the pre-operative bone resection plane includes a series of sequential bone cuts. The exemplary smart cutting guide 1000 of FIG. 35 is programmed to reposition the cutting block 1002 to each progressive bone cut and only open the cutting slot 1003 when the block 1002 is in the correct position and orientation for each particular bone cut.

Figure 38:
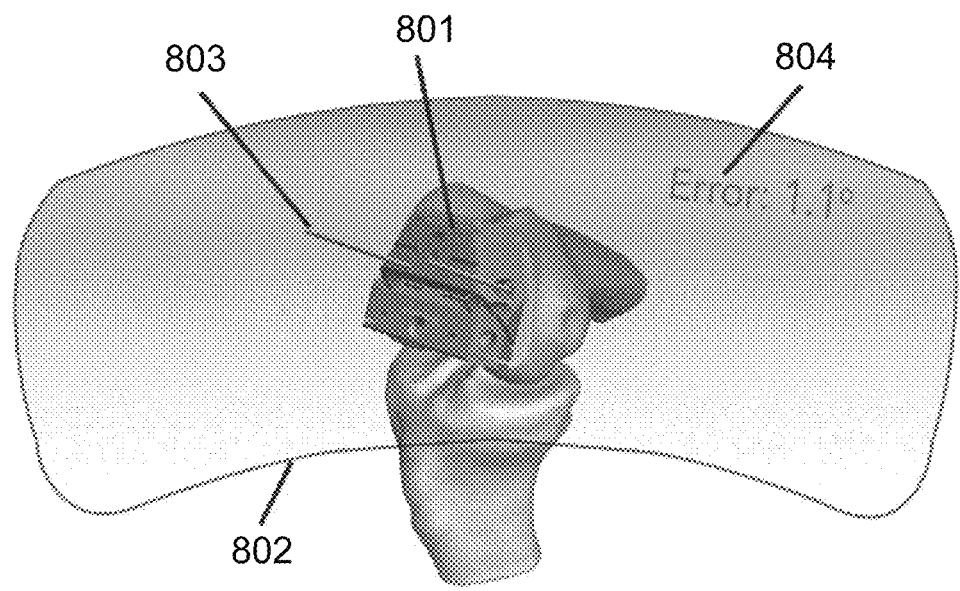
FIG. 38 is a visual depiction of the view through an exemplary augmented reality helmet for visual aids for positioning the distal cutting guide (blue lines) per a pre-operative plan.

Referencing FIG. 38, a visual depiction of the AR heads-up display for positioning a real-world cutting guide 801 with respect to a real-world image of a bone pursuant to a pre-operative plan is shown. By aligning the cutting block with the augmented visual aids, a patient specific procedure can be followed without the need for additional instrumentation. In this exemplary embodiment, the heads-up display on the visor 802 of the AR helmet provides feedback concerning the deviation in position of the real-world cutting guide 801 with respect to the real-world patient bone. In FIG. 38, reference 803 indicates Virtual pins locations, and reference number 804 indicates Virtual display on placement error.

Figure 39:
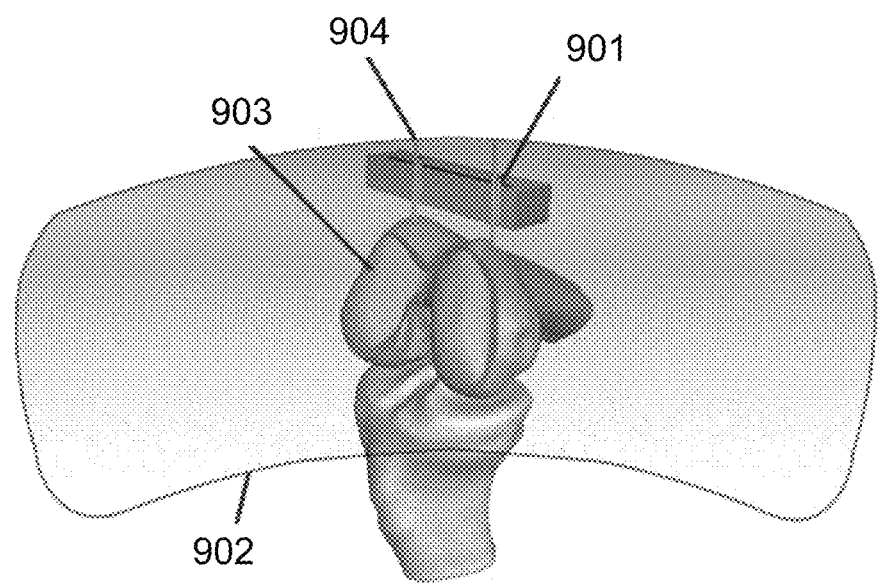
FIG. 39 is a visual depiction of the view through an exemplary augmented reality helmet for positioning of the distal cutting block.

Turning now to FIG. 39, a visual depiction of a guide positioning a real-world cutting block/guide using virtual pins 901 visible via the AR heads-up display. In exemplary form, the virtual pins 901 define the appropriate position relative to the tracked position. The information of the planned position and the tracked position are rendered in the AR display and updated accordingly. In this case the cutting block may be passive (no electronics) or may contain communication and tracking systems, so that the position of the cutting block is known or unknown to the AR system. The cutting block may also contain mechanical stops that prevent cutting through the slot until such time that the guide is placed in the correct position as determined by a pre-operative plan or intraoperative preference. In FIG. 39, reference number 902 indicates AR VISOR, reference number 903 indicates Virtual display on projected resection, and reference number 904 indicates Virtual pins (planned).

Figure 40:
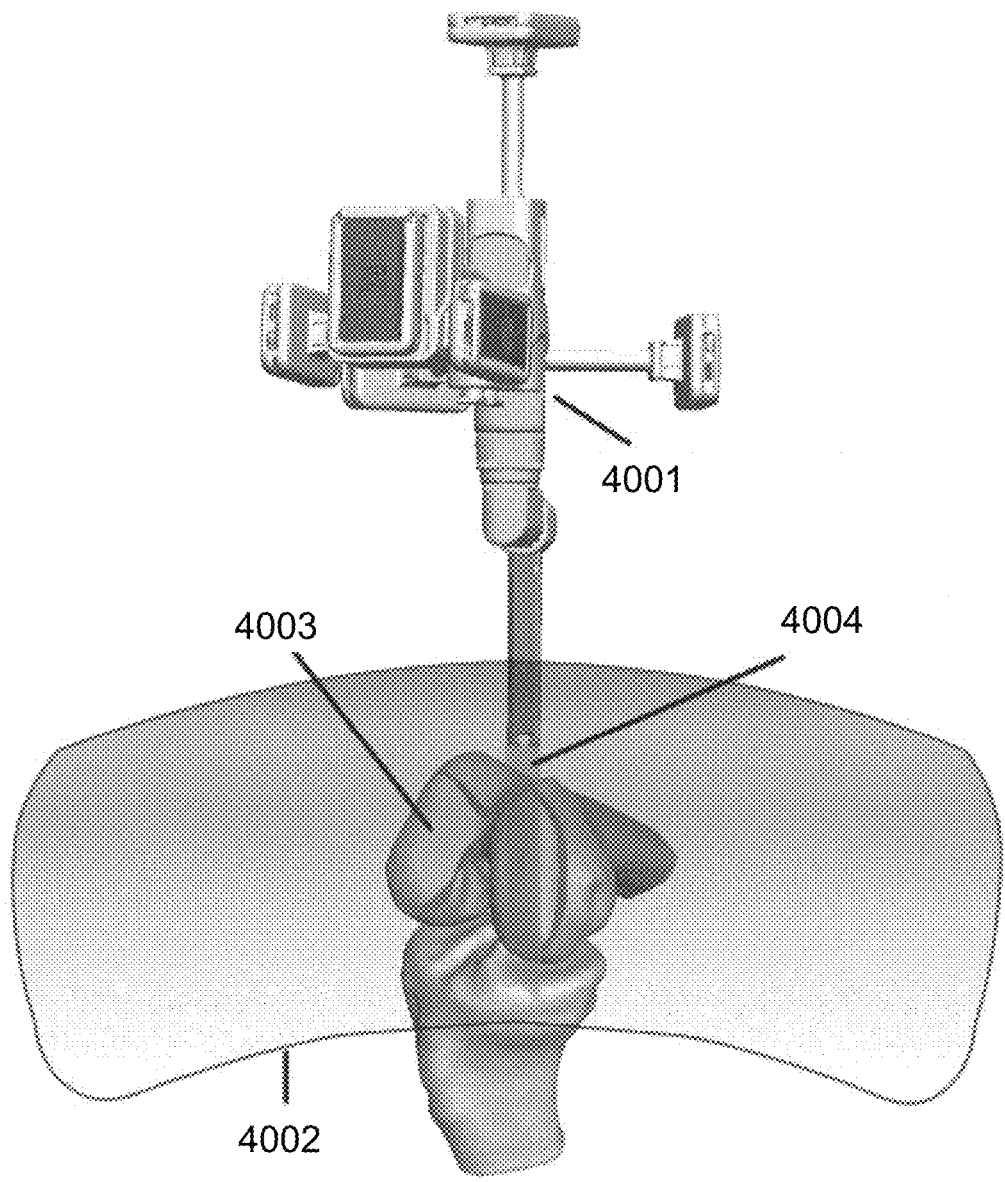
FIG. 40 is a visual depiction of the view through an exemplary augmented reality helmet viewing an oscillating saw equipped with UWB and IMU sensors for tracking in an augmented system.

Moving on to FIG. 40, an exemplary oscillating saw is equipped with UWB and IMU units 4001 for tracking in an AR system. FIG. 40 also depicts the view of a user via the heads-up display associated with a visor 4002 of the AR helmet donned by the user. In exemplary form, the heads-up display shows the AR components of the user's field of view, while the visor 4002 is transparent to allow the user to visualize the real-world elements such as the patient bone and the tangible saw. The path of the saw and the planned cut can be augmented as part of a heads-up display associated with the visor of the AR helmet to provide precise information on cutting parameters. The position and orientation of the cutting blade and its path is updated in real-time relative to the patient so that line of sight is never an issue. In FIG. 40, reference number 4003 indicates Virtual Resection Section, and reference number 4004 indicates Virtual Resection Path.

Figure 41:
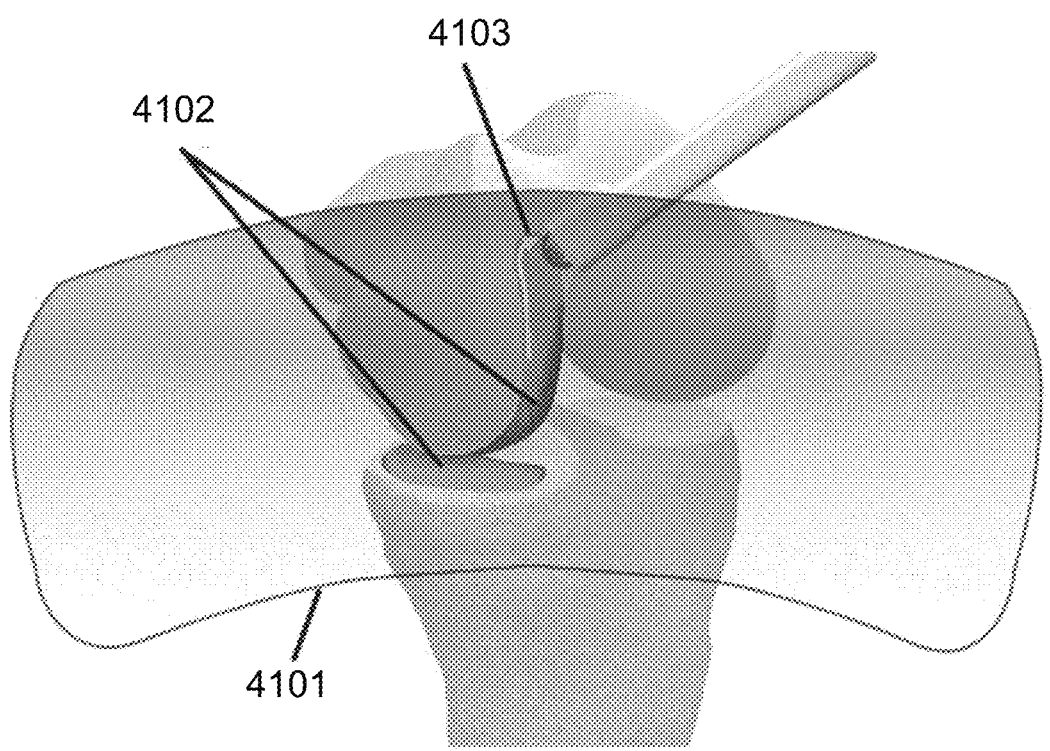
FIG. 41 is a visual depiction of the view through an exemplary augmented reality helmet viewing a smart instruments for knee resurfacing.

Referring to FIG. 41, an exemplary visual representation is displayed of an AR system helmet visor (or AR VISOR 4101) during a knee resurfacing procedure. In exemplary form, the visor's heads-up display depicts the planned resurfacing locations over the top of the real-world image of the patient's bone which is non-augmented. The resurfacing locations are actively displayed to the user on a visor screen or through a holographic display that are visually distinguishable from the real-world image of the patient's bone. As part of a standard surgical technique for bone resurfacing, a motorized burr or router is used to remove cartilage and bone to create a surface ready for orthopedic implant bonding/attachment. In exemplary form, the motorized burr or router surgical instrument may be a connected instrument and contain or be configured with IMU/UWB unit tracking devices that communicate in real-time the orientation and position of the instrument to a CPU or central navigation computer. The CPU or central navigation computer also receives tracking data regarding the anatomy through reference IMU/UWB devices rigidly fixed to the bones or through some aspect of visual tracking or a combination of these methods. This information is sufficient to determine where the surgical instrument is located relative to the patient. As the burr moves within the region that has been highlighted for removal via the AR display, the operator may burr as normal. By way of example, if the location of the burr is detected as being outside of the defined regions, a switch may prevent the motor from activating. This prevents accidental over resection or incorrect implant placement. In this way, a truly wireless, non-line of sight feedback system for smart instruments is applied to resurfacing procedures. The IMU/UWB system provides real-time feedback of the orientation of the burr and depth of burring. In FIG. 41, reference number 4102 indicates Virtual Display on Resurfacing Area, and reference 4103 indicates Virtual Display on Burr Direction.

Ultrasound and UWB for Surgical Navigation

Figure 42:
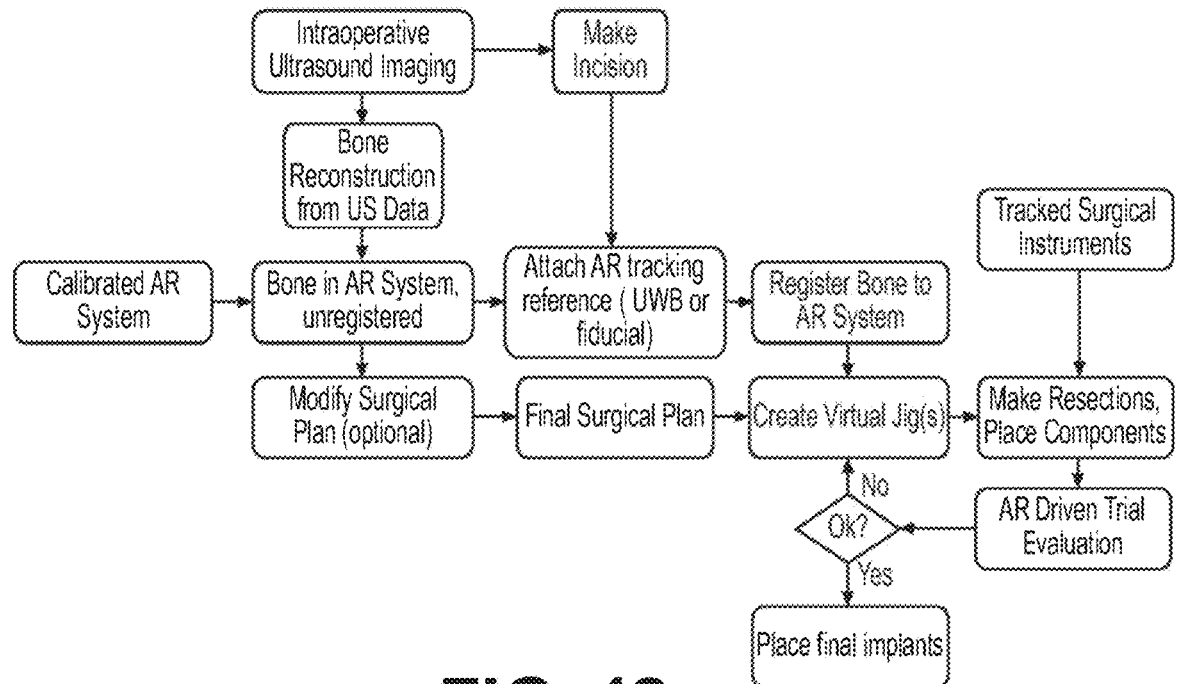
FIG. 42 is a flow diagram representative of a method for ultrasound based surgical navigation, with UWB tracking and virtual guides.

Referring to FIG. 42, in accordance with the instant disclosure, the following is an exemplary method for ultrasound based surgical navigation using UWB tracking and virtual guides. In this exemplary embodiment, there need not be a preoperative imaging step. Instead, a B-Mode ultrasound system having a tracked ultrasound probe is used in the operating room, but prior to the incision, to gather data related to bone surface geometry. This pre-incision information may take the form of B-Mode, RF, or IQ ultrasound data (or any combination of the foregoing) and is converted from ultrasound to 3D point clouds using signal processing techniques known to those skilled in the art. Once all ultrasound data is collected, the patient bone models are reconstructed from the ultrasound data and imported into the augmented reality processing system, which has been previously calibrated. From the bone models and, optionally, the ligament and soft tissue information obtained by the ultrasound system, a default surgical plan is created, which may be optionally modified by the surgical team. The surgical plan contains resection depths and orientation as well as implant sizing. In parallel, the patient anatomies are registered to the AR system using one of many options, including point cloud registration from a tracked probe or visual object recognition through the AR system cameras. Before registration, a reference fiducial marker or tracked probe is rigidly fixed to the real-world anatomy for tracking throughout the surgical procedure. From the registered anatomy and the surgical plan, a virtual cutting guide is created. The AR system displays the virtual cutting guide to the surgeon by rendering a combination of the anatomy and cutting guide on top of the real world images. When performing the resection prescribed by the cutting guide, tracked surgical instruments may be used so that final resection location and orientation can be verified by the system. After resection, the AR system may be used to visualize the orthopedic trial implant evaluation and calculate implant kinematic performance, which, if deemed unsatisfactory, can be used to update the virtual cutting guide for further refinements. If placement and performance are deemed satisfactory, then the surgery can proceed to final implantation.

Figure 43:
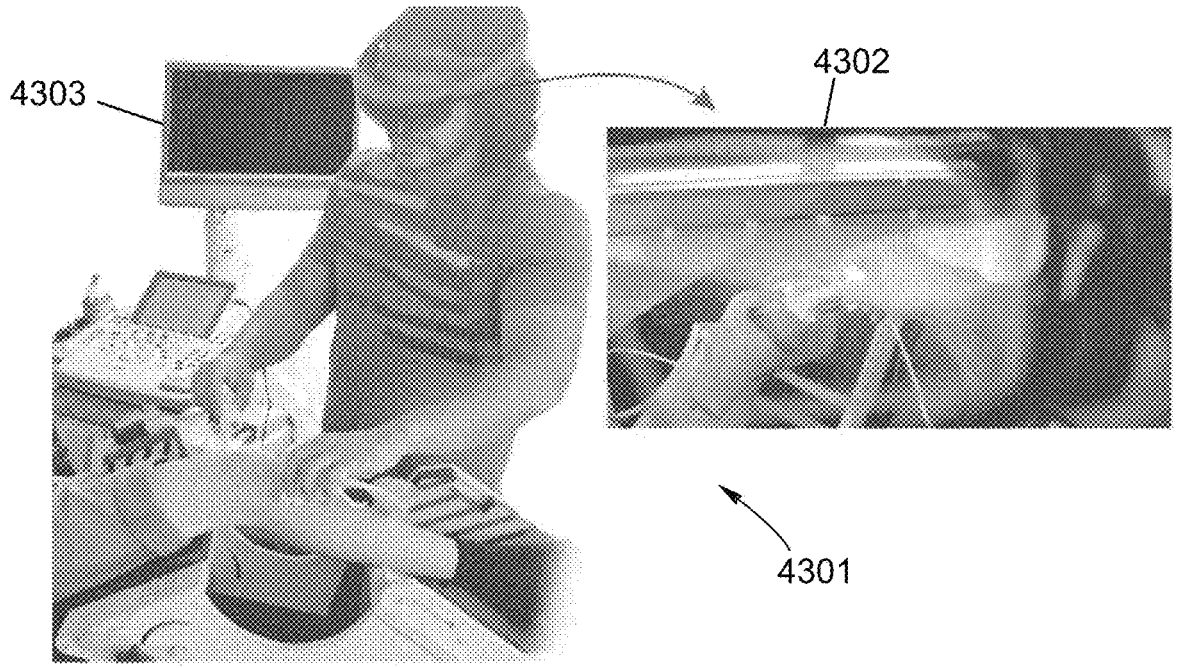
FIG. 43 is a depiction of a user of the augmented reality system being able to visualize appropriate needle path and anatomical structures through the augmented display.

Turning to FIG. 43 showing AR assisted Injection Guidance 4301, the foregoing AR system may be utilized to as part of a surgical, needle injection procedure using UWB tracking and virtual guides. In this exemplary embodiment, pre-operative imaging is carried out to generate a model of the patient's anatomy (e.g., a knee joint). Alternatively, the user may utilize an ultrasound probe to generate ultrasound data representative of the patient's anatomy and generate a point cloud from which a virtual model of the patient anatomy can be generated, as is known by those skilled in the art. Either way, the user/operator is wearing an AR helmet (or AR Guidance 4302) that includes a heads-up display generating virtual images of the patient's bones and the needle, each of which is tracked in 3D using IMU and/or UWB units. More specifically, the operator is holding in his left hand a bone tracking device affixed to the outside of the patient's lower leg, while concurrently holding in his right hand the needle that will be delivered into the interior of the patient's knee joint. As the operator looks through the visor of the AR helmet, virtual representations of the patient's bones of the knee joint and the needle are overlaid the real-world images of the patient's leg in a registered and aligned manner. Given that the patient's leg and needle are concurrently tracked, any change in position and orientation will be updated in real time concurrently via the real-world view and the virtual image of the patient's bone and needle. In this manner, post needle insertion, the operator has direct, virtual line of sight to know precisely how far the needle is injected into the joint and where it is located. In this manner, the operator is able to visualize appropriate needle path and anatomical structures through the augmented display. The anatomical structures may be created through reconstruction of ultrasound data and rendered on the glasses in the appropriate position after registering the helmet to the ultrasound tracking system 4303.

Figure 44:
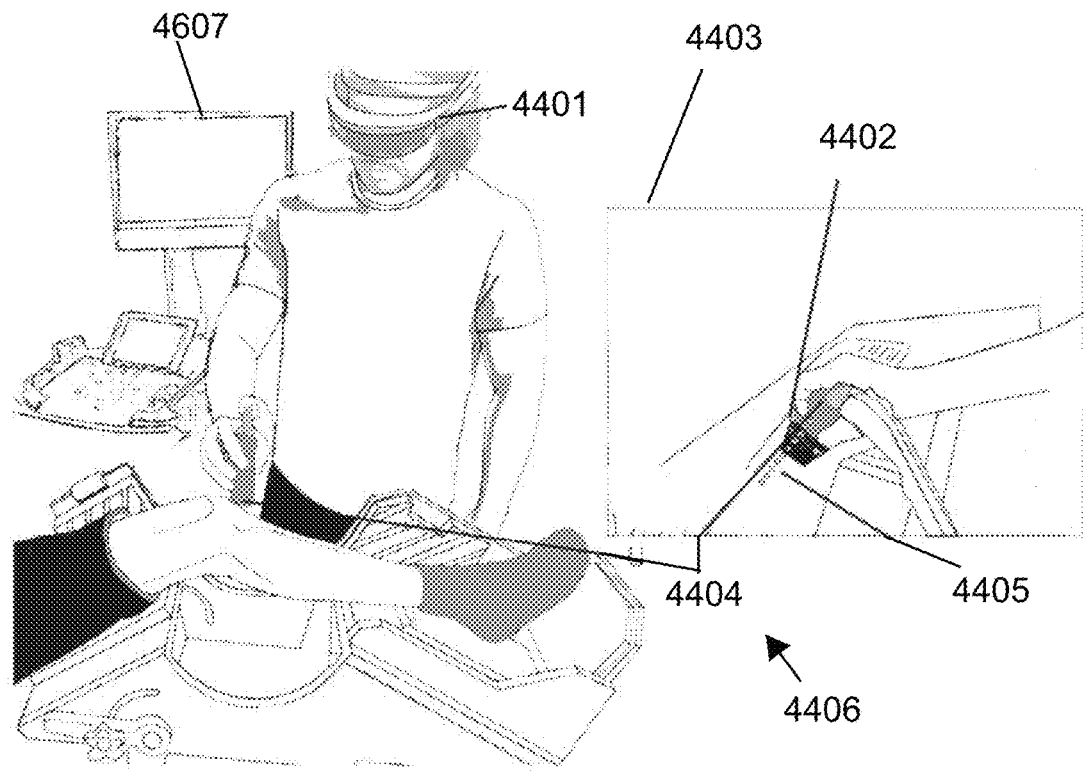
FIG. 44 is a depiction of a user of the augmented reality system being able to view the B-Mode image of the ultrasound being augmented on the patient anatomy to aid in anatomical referencing and remove the need for the operator to watch a computer monitor.

As depicted in FIG. 44, the foregoing AR system may be utilized to overlay the B-Mode image of an ultrasound image onto the patient anatomy to aid in anatomical referencing and remove the need for the operator to watch a computer monitor. In FIG. 44, reference number 4401 indicates AR goggles, reference number 4402 indicates Virtual US Overlay, reference number 4403 indicates User View, reference number 4404 indicates Ultrasound Probe, reference 4405 indicates Virtual Overlay on Scanning Path, reference number 4406 indicates AR Assisted 3D imaging, and reference number 4607 indicates Ultrasound Unit.

Figure 45:
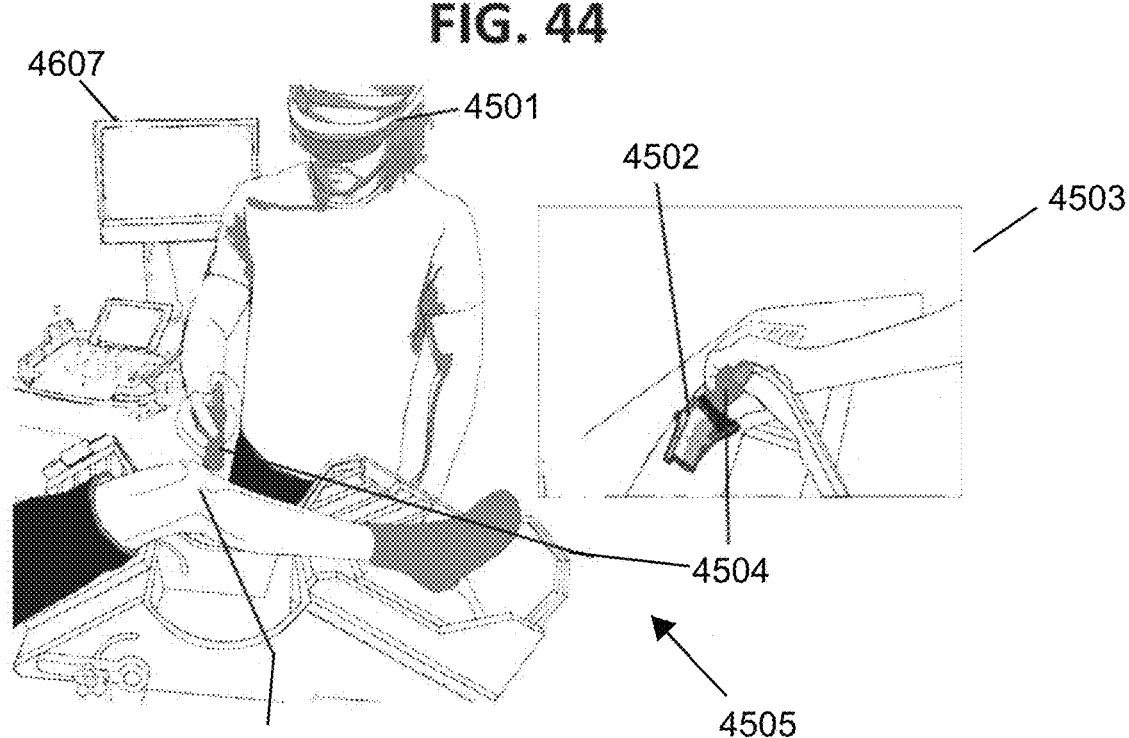
FIG. 45 is a depiction of a user of the augmented reality system being able to view anatomical structures constructed from ultrasound data and displayed on the augmented scene along with the B-Mode images.

Referencing FIG. 45, the foregoing AR system may be utilized to generate virtual anatomical structures constructed from ultrasound data and updated based upon further ultrasound scanning. This can be particularly useful in aiding an operator using ultrasound imaging to find/locate difficult anatomical landmarks or visualizing features located near the reconstructed anatomical structures. In FIG. 45, reference number 4501 indicates AR Goggles, reference number 4502 indicates Virtual Bone Overlay, reference number 4503 indicates User View, reference number 4504 indicates Ultrasound Probe, reference 4505 indicates AR Assisted Joint Diagnosis, reference number 4506 indicates Patient's knee, and reference number 4607 indicates Ultrasound Unit.

Figure 46:
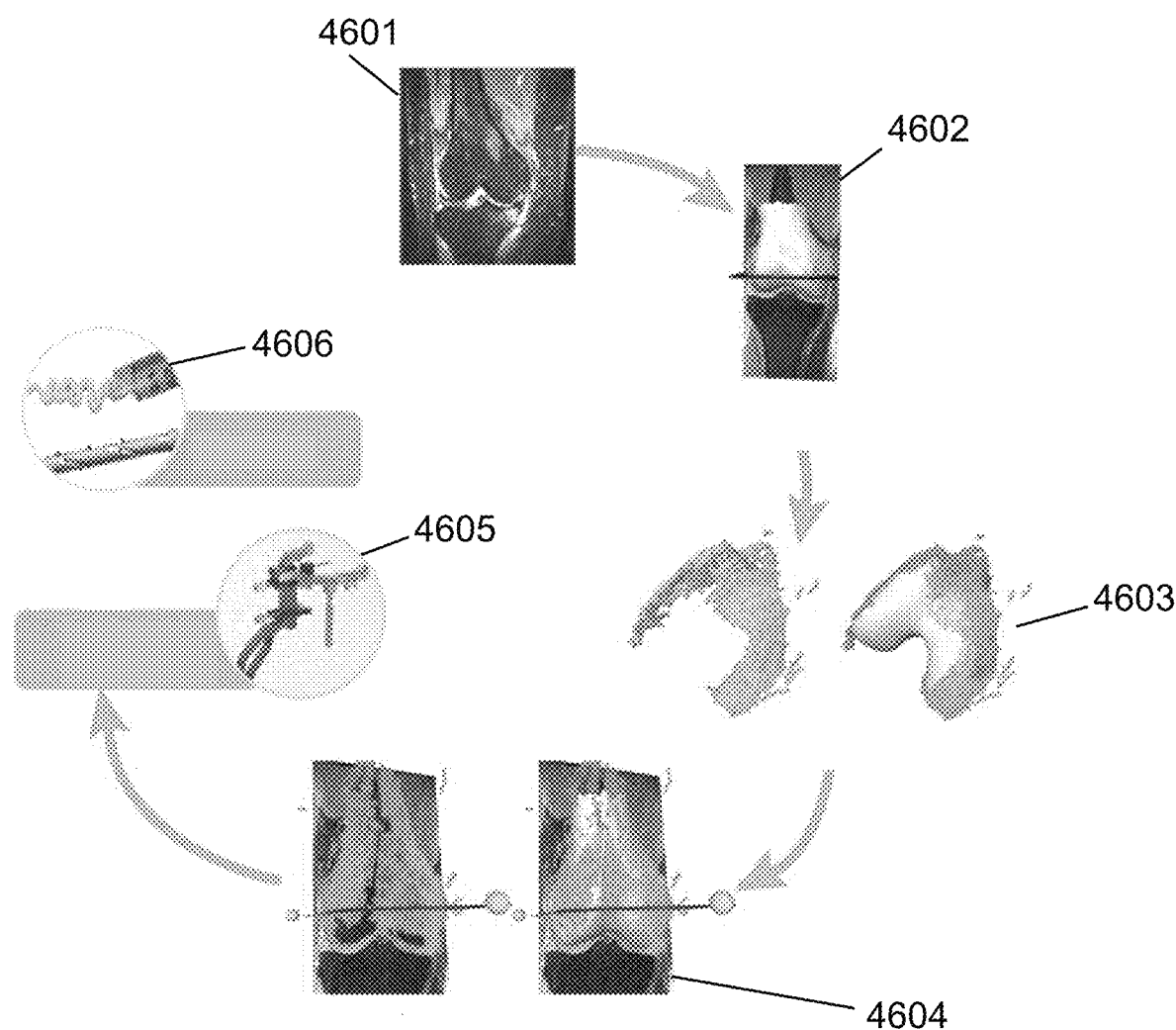
FIG. 46 is a flow diagram depicting one direct application of augmented reality and ultrasound is to create a framework for navigating subchondroplasty procedures.
Figure 47:
FIG. 47 is a screen shot from a surgical planning software showing reconstructed patient bones.
Figure 48:
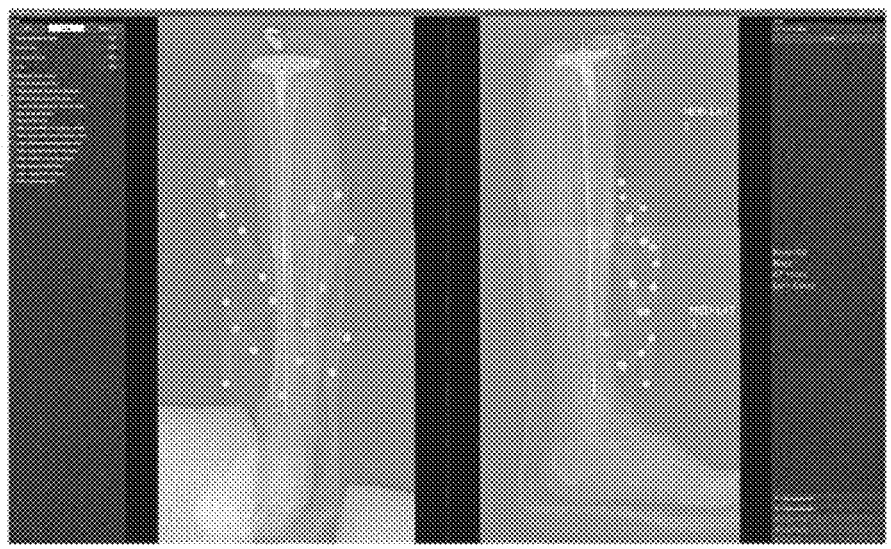
FIG. 48 is a screen shot from a surgical planning software showing mechanical axes projected onto the X-ray images.
Figure 49:
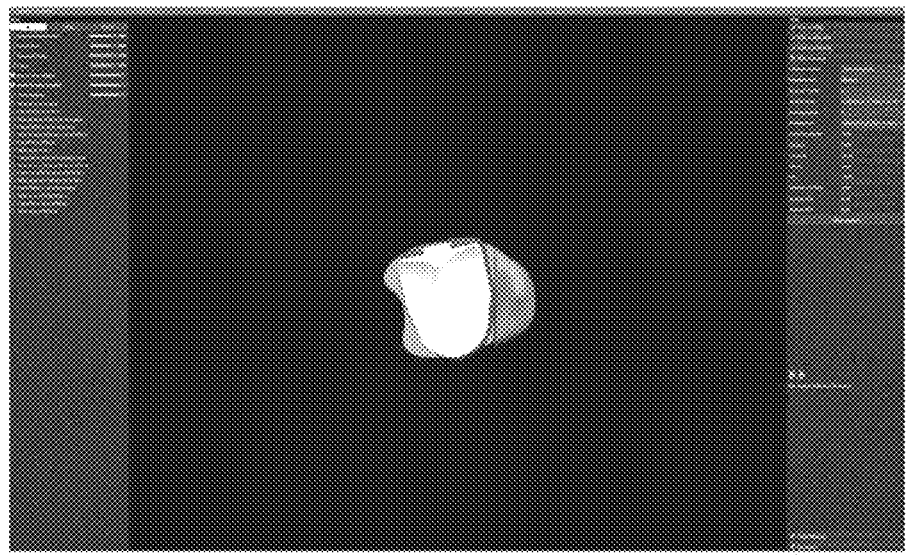
FIG. 49 is a screen shot from a surgical planning software showing tibial implant placement.
Figure 50:
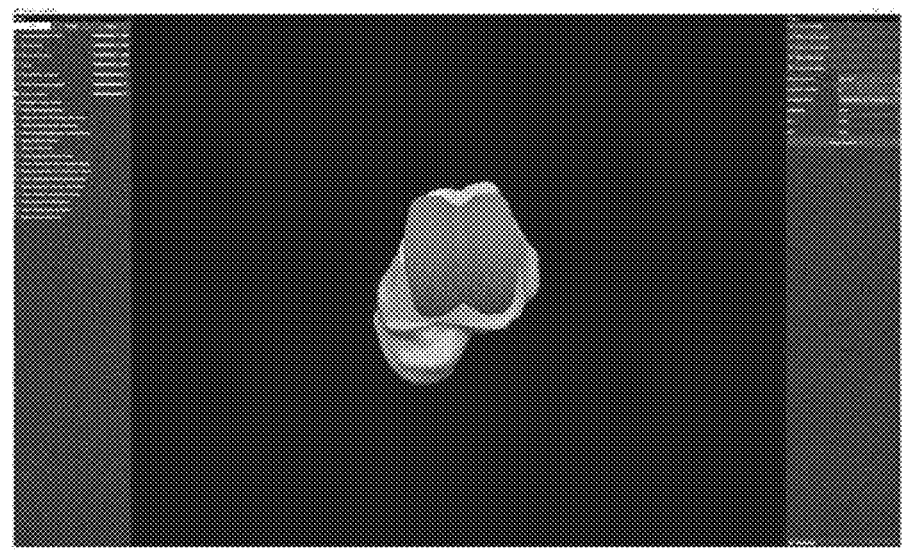
FIG. 50 is a screen shot from a surgical planning software showing talus implant placement.

As shown in FIG. 46, one direct application of AR and ultrasound is to create a framework for navigating subchondroplasty procedures. A pre-operative MRI may be used to create an accurate anatomical model as well as identifying the location of the subchondral defect to be treated. In the operating room, ultrasound may be used to register the MRI data to the patient through identification of the bone boundaries. This information may also be used to register the augmented system to the patient and ultrasound data for navigating the procedure. Finally, the needle path and fixation location of the subchondroplasty instruments are rendered over the patient through the AR display (such as a helmet heads-up display on a visor) and updated in real-time via tracking through UWB units, IMU units, or electromagnetic sensors to aid the surgeon in injecting the subchondroplasty materials. In FIG. 46, reference number 4601 indicates MRI Scan, reference number 4602 indicates Bone Reconstruction with MRI, reference number 4603 indicates Bone Scan with Ultrasound, reference number 4604 indicates MRI US registration, reference number 4605 indicates Navigation Instruments, and reference number 4606 indicates Implants.

UWB and IMU for Non-Line of Sight Surgical Navigation of Total Ankle Arthroplasty The surgical procedure for total ankle arthroplasty requires many complex instruments and techniques. This procedure can be simplified using wireless tracking and customized registration. The following exemplary system includes software and hardware components for performing wireless tracking of surgical instruments and implant components via ultra-wide band communication relative to a known pre-operative surgical plan and patient anatomy.

An initial step as part of this exemplary procedure is pre-operative patient imaging. This can consist of 3D imaging techniques such as MRI or CT, or a plurality of 2D images, such as X-ray, ultrasound or fluoroscopy. The resultant images may be used for creation of virtual patient specific anatomical models. For the ankle, it is commonly required that the fibula, tibia and talus are reconstructed for complete surgical planning. In some cases, it is sufficient to appropriately scale a fibula, calcaneous, and other osseous structures that may provide visual references, but are not required for specific planning parameters.

Surgical planning is the process of generating a pre-operative virtual surgical plan, which may include component sizing, orientation, and positioning from the patient specific virtual surface models. The surgical plan is passed from the planning application to the intraoperative navigation platform, as well as to an optional platform for creating a custom patent anatomical mapper (PAM) for registering the virtual plan to the patient intraoperatively (see FIGS. 47-50).

An exemplary navigation system that may be used as part of this exemplary surgical procedure may require a minimum of two tracking devices. Each tracking device may include a plurality of UWB antennas (such as 4 or more) and inertial measurement units, which may contain accelerometers, gyroscopes and magnetometers. Thus, full position and orientation of the tracking device can be known relative to the second tracking device via fusion of IMU and UWB data.

As part of the exemplary navigation system, a UWB tracking unit may connect multiple antennas to a single transceiver, which enables the ability to range and track multiple UWB antennas (targets) utilizing the same UWB transceiver unit. In an exemplary configuration, the antennas within the UWB tracking unit can serve as either the master or peripheral roles, where the master unit serves as the timing reference for the peripherals units in the system. By way of further example, the antennas within the UWB tracking unit may be arranged in any configuration with the condition that there are more than three antennas and one of the antennas does not reside on the same plane with the other three. For example, a tetrahedron configuration will satisfy this condition. In this configuration, the four antennas may connect to a single UWB transceiver, where each antenna will serve as a reference point for positioning. With a single timing circuitry, and a single transceiver to feed the UWB pulses into multiple antennas, this configuration enables clock synchronization among all reference points in the unit. This configuration can tremendously improve the flexibility of the installation of the master unit, as well as easing the calibration procedure. In short range localization applications, a single master system is sufficient to provide adequate positioning data for localization. In large area localization applications, multiple master systems can be used. The timing circuitry of the master units is synchronized during operation with either wired or wireless methods.

The tetrahedral design allows for determination of the position and orientation of each UWB unit. The addition of one or more IMUs can be used to more accurately determine orientation. Both sensor system outputs are fused, so that errors from the UWB and the IMU(s) are reduced through fusion and filtering techniques (see FIG. 4). One exemplary method to reduce errors includes using a recursive Bayesian estimation filter to compliment the orientation estimation between the UWB and IMU units/system. The IMU system may be inaccurate and subject to magnetic artifact, where the UWB system can be used to provide correction. In addition, the multi-antenna design of the UWB system can be used to monitor and improve translation estimations among the antennas.

In another configuration, the UWB tracking system may use a single or multiple external reference units that may be mounted or placed in different locations within an operating environment (e.g., an operating room) to improve positioning accuracy. The reference unit may use a single or multiple antennas in different configurations. The reference unit may communicate with each other via wire or wireless connections. The reference unit may behave as the master unit to other UWB tracking units, and they may also be configured to performing positioning to any other reference units or UWB tracking unit based on time difference of arrival, time of flight, angle of arrival techniques. The placement of the reference units may be arbitrary or optimized using the estimation based on position dilution of precision (PDOP) (see FIG. 2). The PDOP calculation may also be configured to optimize reference unit placement in 2D or 3D.

In another configuration, the UWB and/or IMU tracking systems may be rigidly fixed to a mobile platform 500, which may be in the form of a surgical robotic system, to improve performance without relying on placing external reference units around the operating room (see FIG. 5). In this exemplary embodiment, the system may be registered to a single bone anatomy by first rigidly fixating a reference UWB-IMU tracker to the bone. The second tracker may be tracked relative to the reference tracker. The registration of the patient anatomy to this local coordinate system can be performed in multiple ways.

One method is to create a patient anatomical mapper (PAM), having at least one surface matching the "negative" of the patient anatomy and a method of being rigidly attached to the second tracker, so that when placed to match the patient anatomy, the position and orientation of the tracker on the PAM is known and the position and orientation of the PAM on the anatomy is known. When placed in the matched location and orientation, the system registers the patient anatomy in the local coordinate system.

A second method is to palpate or digitize the anatomical surface with the tracking device. The advantage of this method is the lack of a PAM. This requires one reference tracker rigidly fixed to patient anatomy. The second tracker is used to sample surface points of the anatomy. Sufficient numbers of surface points are required to obtain a point cloud. This point cloud represents a digitization of the true anatomical surface, and is registered to the previously created virtual surface model. One such point cloud-to-model registration method is called Iterative Closest Point.

Figure 51:
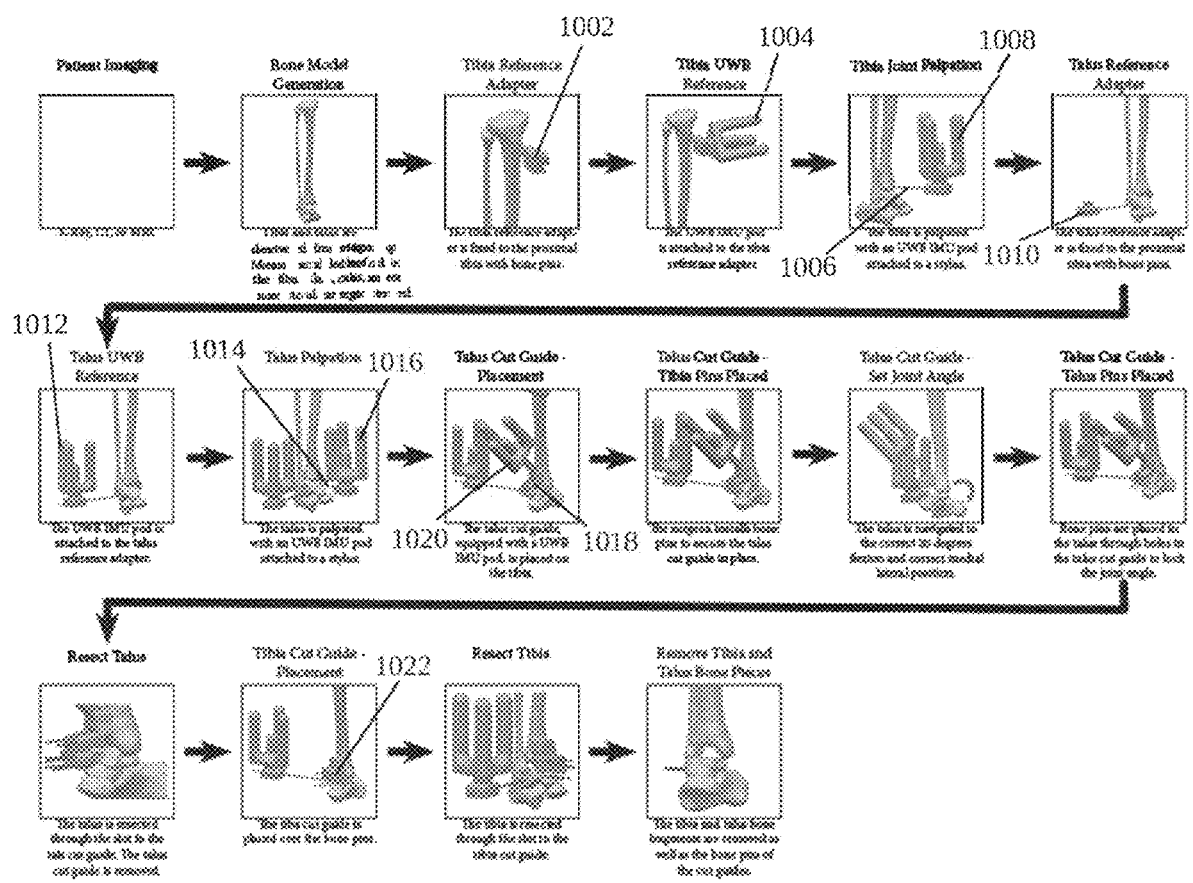
FIG. 51 is a flowchart for UWB/IMU surgical navigation of total ankle arthroplasty.

FIG. 51 provides a process flow diagram for an exemplary total ankle arthroplasty procedure. Initially, the patient ankle is imaged using any number of imaging modalities including, but not limited to CT, MRI, X-ray, ultrasound, and fluoroscopy. Post ankle imaging, virtual models of the bones of the ankle joint are created by deriving the tibia and talus from the ankle images, while mean scaled models of the fibula, calcaneous, and navicular are registered. Next, a tibia reference adapter 1002 is fixed to the proximal portion of the tibia using bone pins. The reference adapter has mounted to it an UWB and IMU pod/unit 1004. Thereafter, the tibia joint is palpated using a stylus 1006 having mounted thereto an IMU and UWB pod 1008. A talus reference adapter 1010 is then fixed to the proximal tibia using bone pins, followed by mounting an IMU and UWB pod 1012 to the talus reference adapter. Thereafter, the talus is palpated using a stylus 1014 having mounted thereto an IMU and UWB pod 1016. Post palpation, a talus cutting guide 1018 equipped with UWB and IMU units 1020 is positioned on the tibia. Next, a surgeon may install bone pins to secure the talus cutting guide in position. Thereafter, the talus is navigated to the correct flexion angle (e.g., 20 degrees) and the correct medial-lateral position. Bone pins are then mounted to the talus through holes in the talus cutting guide to lock the angle of the ankle joint. Thereafter, the talus is resected through a slot in the talus cutting guide 1018, after which the talus cutting guide 1018 can be removed. Using the same bone pins previously attached to the tibia, a tibia cutting guide 1022 is mounted to the tibia and the tibia is resected using a slot in the cutting guide. Ultimately, the tibia and talus bone fragments are removed as are the pins previously mounted to the tibia and talus. It should be noted that registration may be performed on the tibia and talus separately. Tracked during the procedure are the cutting blocks required to perform resections of the talus and tibia that match the pre-operative surgical plan.

Figure 52:
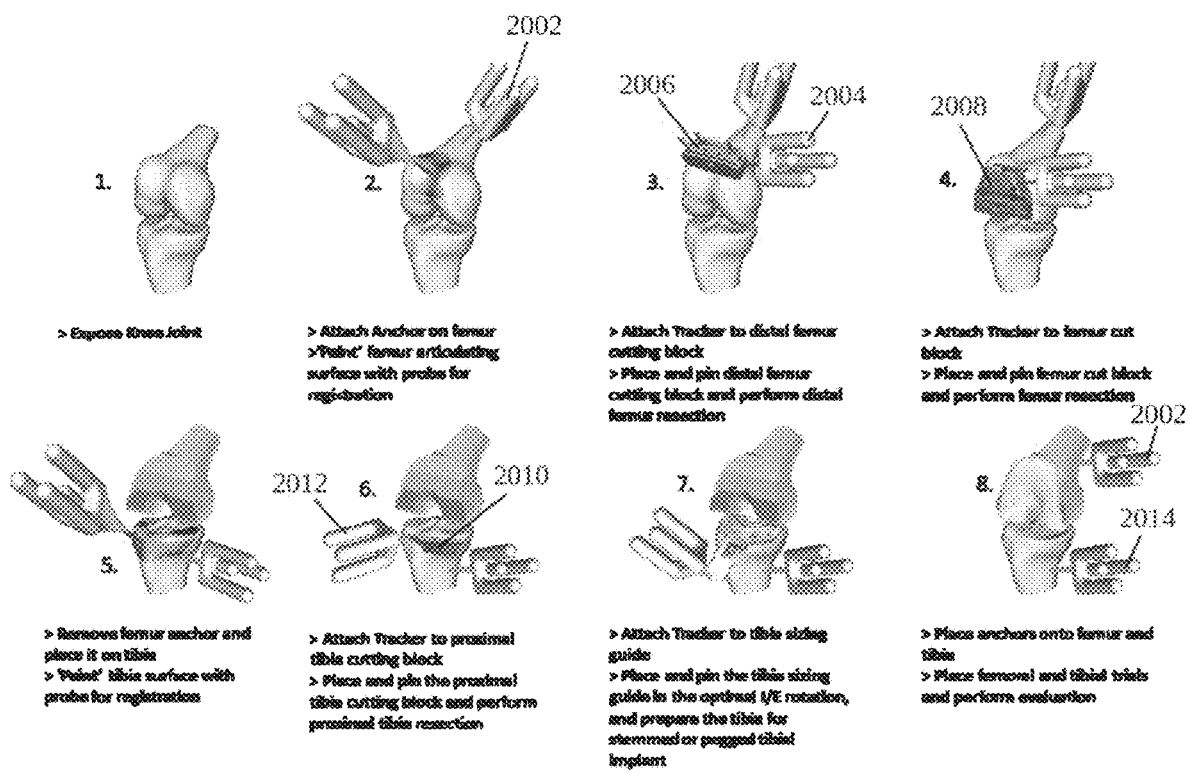
FIG. 52 is a flow diagram for using UWB and IMU tracking systems in total knee replacement.

UWB and IMU for Non-Line of Sight Surgical Navigation of Total Knee Arthroplasty Referring to FIG. 52, the foregoing exemplary navigation system may also be utilized to perform navigated total knee replacement/arthroplasty.

As part of this process, patient imaging is taken preoperatively. This can consist of 3D imaging techniques such as MRI or CT, or a plurality of 2D images, such as X-ray, ultrasound or fluoroscopy. These images are used for creation of virtual patient specific anatomical models. For the knee, it may be required that, at minimum, the knee portion of the joint be created (distal femur and proximal tibia).

Post image acquisition, surgical planning may be performed. Surgical planning is the process of generating a virtual surgical plan, which may include component sizing, orientation and positioning, from the patient specific virtual surface models. The surgical plan is passed from the planning application to the intraoperative navigation platform, as well as to an optional platform for creating a custom patent anatomical mapper (PAM) for registering the virtual plan to the patient intraoperatively.

The exemplary navigation system may require at a minimum two tracking devices. Each tracking device may contain a plurality of UWB antennas (at least 4) and inertial measurement units, which may contain accelerometers, gyroscopes and magnetometers. Thus, full position and orientation of the tracking device can be known relative to the second tracking device via fusion of IMU and UWB ranging data.

In this exemplary process and apparatus, a UWB tracking unit may connect multiple antennas to a single transceiver, which enables the ability to range and track multiple UWB antennas (targets) utilizing the same UWB transceiver unit. In an example configuration, the antennas within the UWB tracking unit can serve as either the master or peripheral roles, where the master unit serves as the timing reference for the peripherals units in the system. The antennas within the UWB tracking unit can be arranged in any configuration with the condition that there are more than three antennas and one of the antennas does not reside on the same plane with the other three. For example, a tetrahedron configuration will satisfy this condition. In this configuration, the four antennas may connect to a single UWB transceiver, where each antenna will serve as a reference point for positioning. With a single timing circuitry, and a single transceiver to feed the UWB pulses into multiple antennas, this configuration enables clock synchronization among all reference points in the unit. This configuration can tremendously improve the flexibility of the installation of the master unit; as well as easing the calibration procedure. In short range localization application, a single master system is sufficient to provide adequate positioning data for localization. In large area localization applications, multiple master systems can be used. The timing circuitry of the master units are synchronized during operation with either wired or wireless methods.

By connecting multiple antennas to a single transceiver, it enables the ability to create multiple anchors or tags within the same UWB unit. The UWB antenna array in both central and peripheral units can be arranged in any configuration with the condition that one of the antennas does not reside on the same plane with the other three. For example, a tetrahedron configuration will satisfy this condition. The UWB antenna array in the central unit serves as the anchors for the system. For example, a tetrahedron configuration will have four antennas connected to a single UWB transceiver. This creates four anchors in the central unit. With a single clock, and a single transceiver to feed the UWB pulses into multiple antennas, this configuration enables clock synchronization among all anchors in the unit. This configuration can tremendously improve the flexibility of the installation of the anchors; as well as easing the calibration procedure of the unit. In short range localization application, a single central system is sufficient to provide adequate anchors for localization. In large area localization application, multiple central systems can be used. The clocks of the central units are synchronized during operation with either wired or wireless methods.

In alternate exemplary configuration, the UWB tracking system may use a single or multiple external reference units that may be mounted or placed in different locations within the operating room to improve positioning accuracy. The reference unit may use a single or multiple antennas in different configurations. The reference unit may communicate with each other via wire or wireless connections. The reference unit may behave as the master unit to other UWB tracking units, and they may also be configured to performing positioning to any other reference units or UWB tracking unit based on time difference of arrival, time of flight, angle of arrival techniques. The placement of the reference units may be arbitrary or optimized using the estimation based on position dilution of precision (PDOP). (FIG. 2) The PDOP calculation may also be configured to optimize reference unit placement in 2D or 3D.

In a further alternate exemplary configuration, the UWB and/or IMU tracking systems may be rigidly fixed to a mobile platform, which may be in the form of a surgical robotic system, to improve performance without relying on placing external reference units around the operating room. (FIG. 5) In the proposed invention, the system is registered to a single bone anatomy by first rigidly fixating a reference UWB-IMU tracker to the bone. The second tracker is tracked relative to the reference tracker. The registration of the patient anatomy to this local coordinate system can be performed in multiple ways.

The system is registered to a single bone anatomy by first rigidly fixating a reference UWB-IMU tracker to the bone. The second tracker is tracked relative to the reference tracker. The registration of the patient anatomy to this local coordinate system can be performed in multiple ways.

One method is to create a patient anatomical mapper (PAM), having at least one surface matching the "negative" of the patient anatomy and a method of being rigidly attached to the second tracker, so that when placed to match the patient anatomy, the position and orientation of the tracker on the PAM is known and the position and orientation of the PAM on the anatomy is known. When placed in the matched location and orientation, the system registers the patient anatomy in the local coordinate system.

A second method is to palpate or digitize the anatomical surface with the tracking device. The advantage of this method is the lack of a PAM. This requires one reference tracker rigidly fixed to patient anatomy. The second tracker is used to sample surface points of the anatomy. Sufficient numbers of surface points are required to obtain a point cloud. This point cloud represents a digitization of the true anatomical surface, and is registered to the previously created virtual surface model. One such point cloud-to-model registration method is called Iterative Closest Point.

Referring specifically to FIG. 52, an exemplary procedure for utilizing UWB and IMU trackers is depicted. Step 1 begins with knee joint exposure via a surgical process. Step 2 includes rigid fixation of a reference tracker/unit 2002 on the femur and registering the femur to the tracking system. Image registration is performed by digitizing the surface of the exposed joint. In an alternate exemplary embodiment, the registration can be performed with a custom device shaped to match in a unique location and orientation on the femur (bone), which is known pre-operatively. The tracker is attached to the custom registration device in a known location and orientation so that, when placed on the patient anatomy, the position and orientation of the tracker is known relative to the patient anatomy. Step 3 involves attaching the tracker 2004 to the existing surgical device 2006 used for making the distal knee cut. The system tracks the position and orientation of the instrument relative to the patient femur, providing feedback to the surgeon on expected resection depth and orientation. When the position of the cutting block 2006 matches the surgical plan, the block is pinned to the patient anatomy. Alternatively, the tracker can be tied directly to the cutting instrument or to a bone pin. Step 4 is performed after the distal cut, and is similar to step 3 with the difference being that the surgical instrument being tracked relative to the anatomy is the cutting block 2008 for performing posterior, anterior and chamfer resections. After the femoral resections are performed, step 5 involves registration of the tibia, which is performed in a similar manner as disclosed in step 2. Step 6 involves tracking the position and orientation of the tibia cutting instrument 2010 (using a tracker 2012) and pinning this in the desired location, after which the resection is made. Step 7 uses the tracking system for determining the rotation and sizing of a tibia implant after resection. This may involve setting the rotation relative to landmarks on the tibia or kinematic landmarks that may be coupled to the femur anatomy. After appropriately placed, trial implants can be used with the trackers 2002, 2014 rigidly fixed to the implants or patient anatomy, as in step 8, to test for ideal procedural outcomes, such as kinematics or laxity. It should be noted that registration is performed on the femur and tibia separately. Tracked during the procedure are the cutting blocks 2006, 2008, 2010 required to perform resections of the femur and tibia that match the pre-operative surgical plan. Alternatives to the procedure described include, without limitation: (i) after registration, sizing information can be determined or verified by selecting appropriate sizing landmarks with the tracked probe; and, (ii) custom surgical instruments made specifically for the tracking probes could be used in place of conventional instrumentation.

Dynamic Patient Specific Implants: Morphology Meets Kinematics

Figure 53:
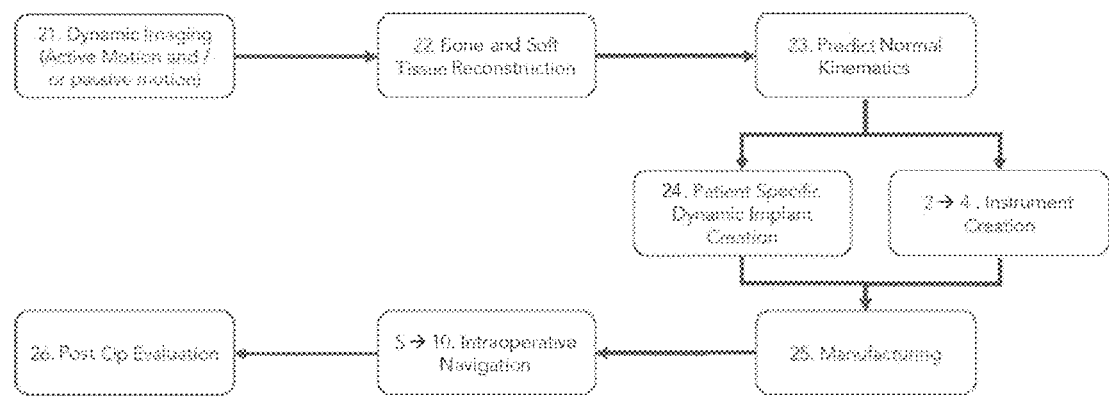
FIG. 53 is a flow diagram of an exemplary process of utilizing dynamic data across the episode of surgical care to create patient-specific implants and instruments, place the implant and monitor performance post-operatively.

Referring to FIG. 53, an exemplary process for utilizing dynamic data across the episode of surgical care to create patient-specific implants and instruments, as well as place the implant and monitor performance post-operatively. The process includes a kinematic assessment that may be carried out using fluoroscopic or other dynamic imaging modality (as opposed to traditional, static imaging), which is uploaded to a processing CPU to reconstruct motion and anatomical structures from the imaging data. The kinematics and anatomical structures are used as inputs to a prediction model for determining optimal reconstructive shape and normal kinematics. The output shape parameters are used to construct the dynamically created patient specific implants and associated instruments. The implants and instruments are manufactured and coupled with the surgical plan and smart instrumentation in the operating room to achieve precise placement. Finally, to monitor performance, post-operative data, such as kinematics and range of motion, along with patient reported outcomes, is collected through any number of sensors, including IMU, UWB or combinations thereof. This data can then be utilized in a feedback loop with the predictive engine to optimize future patient implant parameters. In this manner, data from the entire episode of care can be utilized to drive implant and instrument design.

Figure 54:
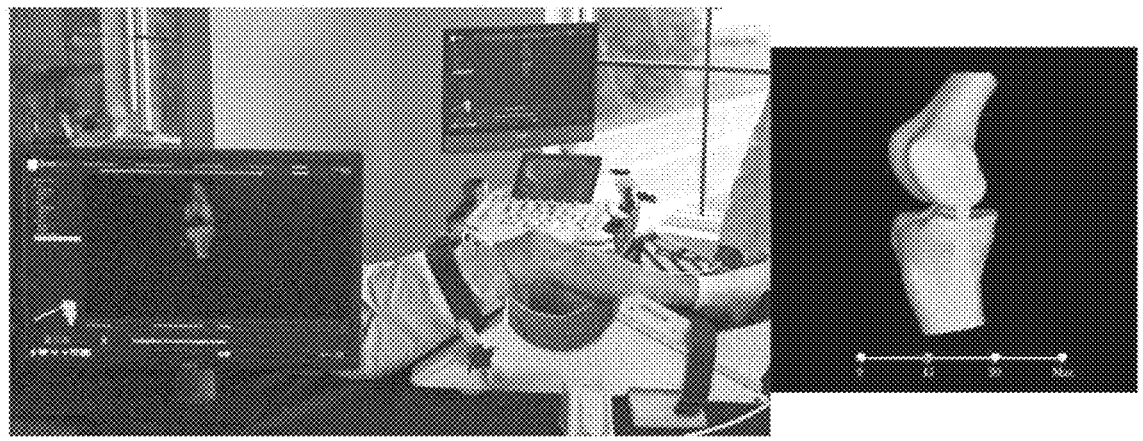
FIG. 54 includes photographs depicting examples of dynamic joint reconstruction.

A prefatory step, step 21, in the dynamic implant creation process depicted in FIG. 53 is dynamic patient imaging. Dynamic patient imaging can be achieved through use of static 3D imaging techniques such as MRI or CT followed by active and passive kinematic activity collected through a motion capturing system (e.g., Optical, EM, UWB and/or IMU). Imaging can also be performed using ultrasound dynamic patient imaging and joint reconstruction as depicted in FIG. 54. As shown in FIG. 54, 3D bone information can be captured from ultrasound images (RF Data, B-Mode images or IQ data) or other imaging modalities. Coupling the imaging device with tracking sensors on the patient provides the ability to reconstruct more of the anatomy as well as capture dynamic information needed for creating the patient specific kinematics and soft tissue envelopes used for the described implant design method.

Another method for dynamic imaging is using fluoroscopic imaging. Patient joint models are then reconstructed from this video sequence. In order to reconstruct patient joint models, an overlay of patient specific shape information onto single-plane digital fluoroscopy (top left of FIG. 55). The contact regions during the activity are tracked to extract joint curvature and soft tissue information. An example of 3D point and curvature information extracted from fluoroscopy is seen in the top right image of FIG. 55.

Figure 55:
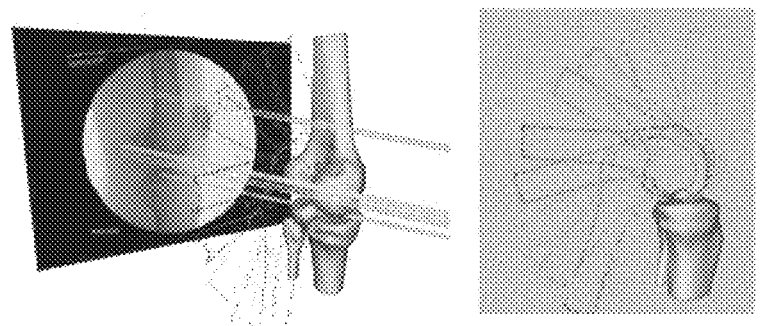
FIG. 55 comprise images depicting overlay of patient specific shape information onto single-plane digital fluoroscopy.
Figure 55:
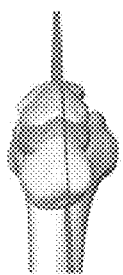

The points represent the 3D surface geometry of the femur and are coupled to the tibia curvature at articulating regions. Within the articulating regions, one may extract normal curvatures by comparison with a database of shapes and kinematics and use the closest output from the database to optimize the manufactured component to match the normal profile. The bottom image of FIG. 55 illustrates how the patellofemoral kinematics (also extracted from fluoroscopy or ultrasound data) can drive custom patellofemoral groove curvature from the articulating surface of the patella and groove orientation for optimal patellofemoral tracking.

Figure 56:
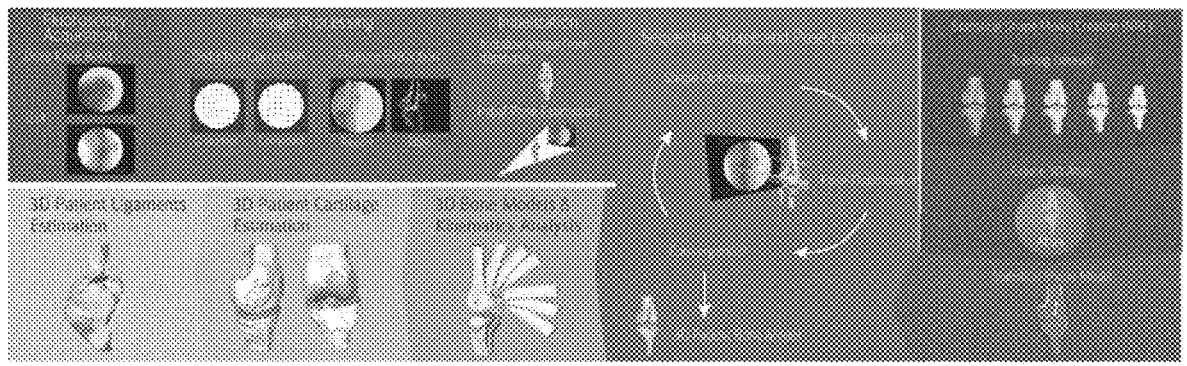
FIG. 56 is a flow diagram depicting an exemplary process of creating anatomical information from dynamic image data.

Post dynamic imaging, a bone and soft tissue reconstruction step 22 is performed. By way of example, the bone and soft tissue reconstruction step may utilize fluoroscopy and be composed of four parts, as shown in FIG. 56, which include, without limitation: (i) image processing, which extracts features from fluoroscopic images; (ii) initialization, which estimates the 3D model's initial pose using a hybrid classifier integrating k-nearest neighbors (KNN) and support vector machine (SVM); (iii) optimization, which determines the 3D model's optimal pose and shape by maximizing the similarity measure between the 2D X-ray fluoroscopy and the reconstructed 3D surface mesh model. The similarity measure is designed as a novel energy function including edge score, region score, homogeneity score, and multibody registration score; and, (iv) 3D Shape Analysis, which represents the training dataset of 3D surface mesh models with nonlinear statistical shape model named kernel principal component analysis (KPCA).

As depicted in FIG. 56, creation of anatomical information from dynamic fluoroscopic image data begins with fluoroscopic image acquisition. As part of this image acquisition, the subject/patient may be observed at any number of positions that include a deep knee bend and opposing gait endpoints. Post image acquisition, an image processing substep is carried out.

Using a calibration target, one can estimate distortion and remove it from subsequent images as part of the image processing substep. An exemplary first step in this procedure is to estimate any 2D image's geometric distortion. By taking an X-ray of a known rectangular grid of metal beads, one can estimate a 2D spatial transform for each small square sub-image that is bounded by four beads. Using standard techniques in geometric distortion removal, a local bilinear model may be used to model the spatial mapping, as well as the gray level interpolation. Once the 2D distortion has been removed, the effective source-to-image plane distance (focal length) can be computed by a two-plane calibration grid with a known displacement between the planes.

Figure 57:
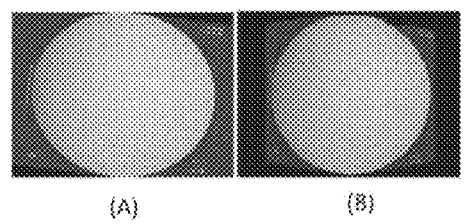
FIG. 57 comprises fluoroscopic images of geometric calibration grid, before distortion removal and after distortion removal edge.
Figure 58:
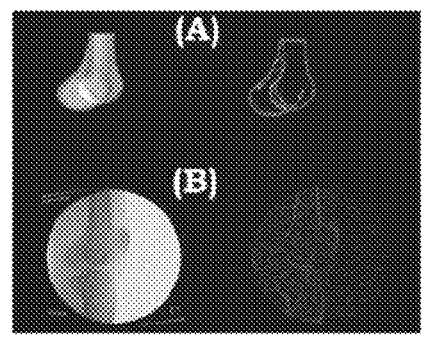
FIG. 58 is a depiction of a process flow for generating 3D models from fluoroscopy image features.

FIG. 57 illustrates a fluoroscopic image of a geometric calibration grid before and after geometric distortion removal. As part of this substep, one may compute the bilinear transform for each set of four grid points that transforms the image positions of the beads in the left image to regularly spaced grid locations in the right. Clearly, the calibration procedure removes the pin-cushion distortion so that the grid points lie along straight lines.

Figure 59:
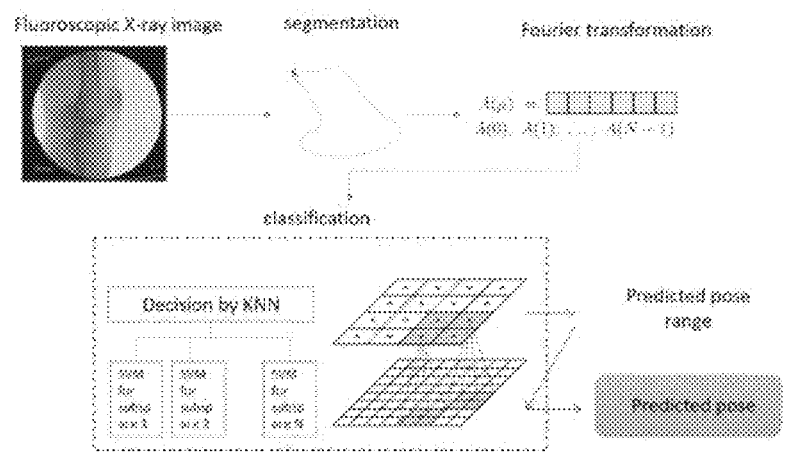
FIG. 59 is a diagram depicting initialization with a hybrid classifier.

Post image processing, an initialization substep may be performed to determine the initial pose of the mean model. The initialization is based on a hybrid classifier combining k-nearest neighbor and support vector machine, as shown in FIG. 59.

As depicted in FIG. 56, two primary methods of reconstruction are developed for building 3D patient anatomy from fluoroscopy images. A first method, Method 1, comprises a sequential shape and pose estimation, whereas a second method, Method 2, comprises reconstruction using And-Or-Tree (AoT). A more detailed discussion of each of these models follows.

Figure 60:
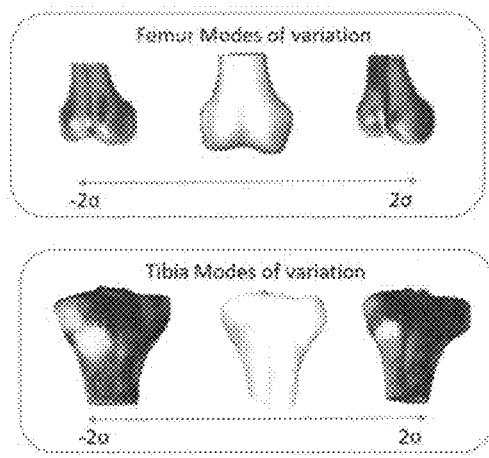
FIG. 60 is a diagram depicting KPCA model variation applied to a knee joint.
Figure 61:
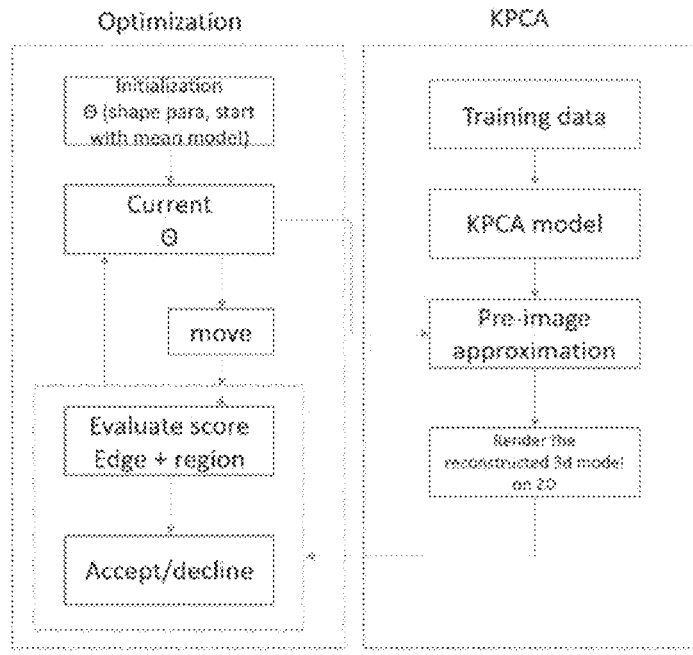
FIG. 61 is a diagram depicting a process for pose and shape parameter optimization.

A sequential shape and pose estimation 3D reconstruction is based on a nonlinear statistical shape model, namely kernel principal component analysis (KPCA). By projecting the training data onto high-dimensional kernel space, we can represent the shape of the 3D model by a vector of shape parameters, as shown in FIG. 60. As part of this first method, an optimization process is carried out where the optimization determines the 3D model's shape and pose parameters from a sequence of monoplane fluoroscopic X-ray images, as shown in FIG. 61. Optimization is based on a novel energy function, which combines the edge, region, homogeneity, and multi-body registration score to measure the similarity between the 3D model and the 2D X-ray image, as shown in Table 1. The hybrid energy function requires neither time-consuming DRR generation nor error-prone 2D segmentation.

Figure 62:
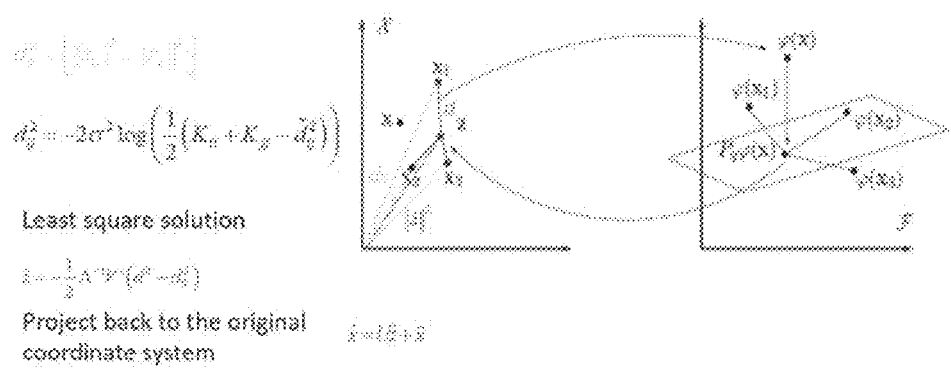
FIG. 62 is a diagram depicting the relationship between input-space distance and feature-space distances.
Figure 63:
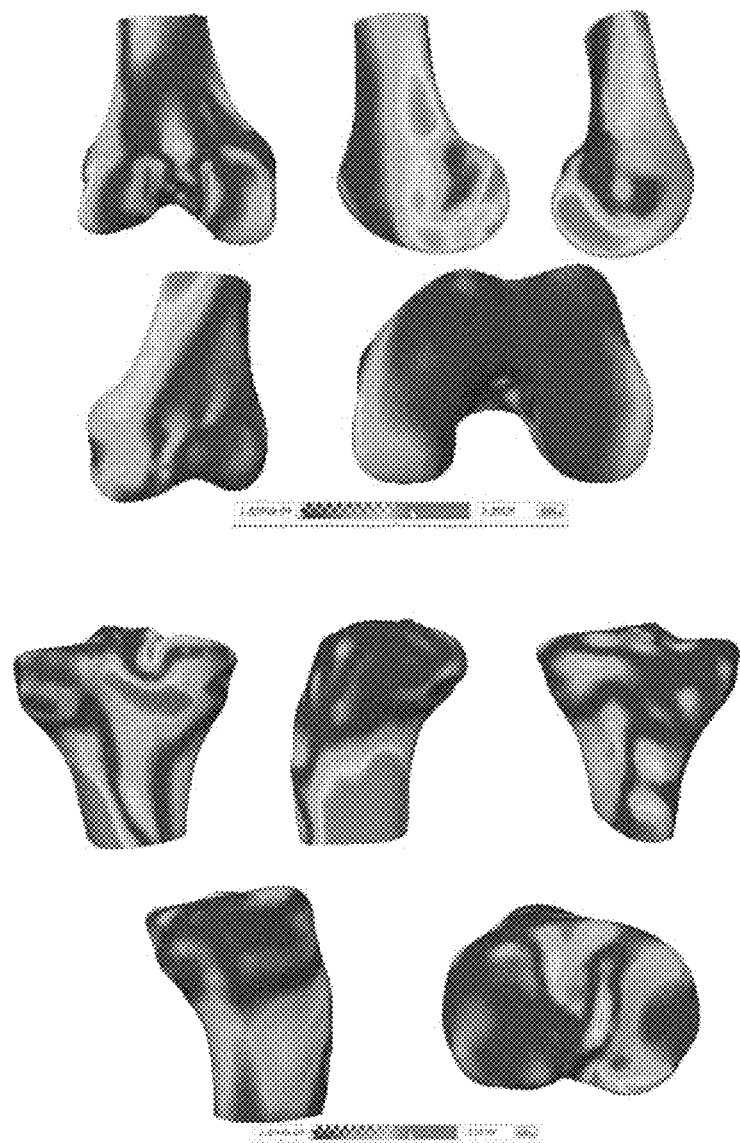
FIG. 63 is a series of images showing reconstruction results of femur and tibia patient anatomy from fluoroscopy compared to CT.
Figure 64:
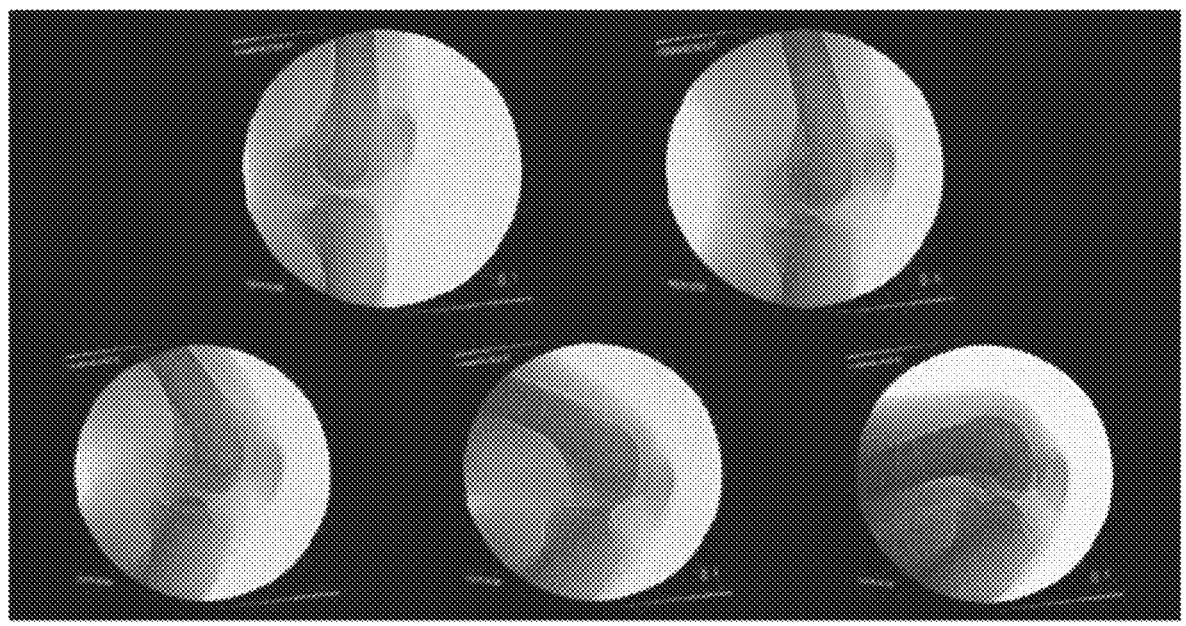
FIG. 64 comprises a series of fluoroscopic images with edge overlay.

Thereafter, the 3D model is reconstructed by a pre-image approximation, because the map between the input and feature space points is not necessarily known. It is preferred to reconstruct the pre-image of the corresponding test point based on the distance constrain in the input space. This is achieved by establishing the relationship between input-space distance and feature-space distances, as shown in FIG. 62.

Figure 65:
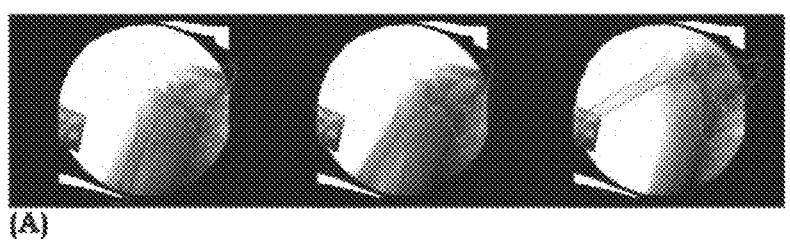
FIG. 65 comprises exemplary images of shoulder and hip reconstruction from X-ray fluoroscopy.
Figure 65:
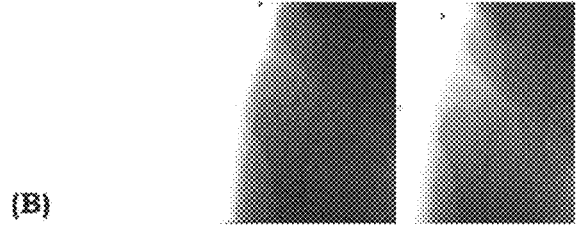

Alternatively, as depicted in FIG. 65, the reconstruction may be performed with the AOT technique. Initially, the geometry space is decomposed by extracting volumes of interest (VOI) as volumes where part templates may exist. Each VOI is further divided into a set of overlapping sub-volumes, which are used as bounding volumes for the placement of part templates. The examples of the sub-volumes are shown on the node on the left side of FIG. 65. The "And-or tree" can be generated recursively by partitioning volumes and representing partitions by And-or node pairs. The "or node" connects to all the "and nodes" that slice the volume represented by this "or node" into two sub-volumes. The "or node" also connects to two sets of leaf nodes, where on each node a surface is placed by either inscribing the volume or on the surface perpendicular to the depth direction. Each "and node" connects two or nodes, with each representing one of the two smaller sub-volumes occupying the current sub-volume. This tree starts from a root "OR node" representing the volume of interest (VoI), and keeps growing until the sub-volumes are divided to a size limit. Using surface as bounding boxes, appearance of part templates can be further defined. Possible appearance for each part template is also represented by an "and-or tree," where "and" represents composition and "or" represents deformation. Layers of "and nodes" de-compose the part templates into curve segments. These curves are projected onto image plane. The 3D object template can be converted to a 2D object template composed of active curves, which should resemble object appearance in the image plane. The deformed active curves are then projected back into the object space as the reconstructed 3D model.

Figure 66:
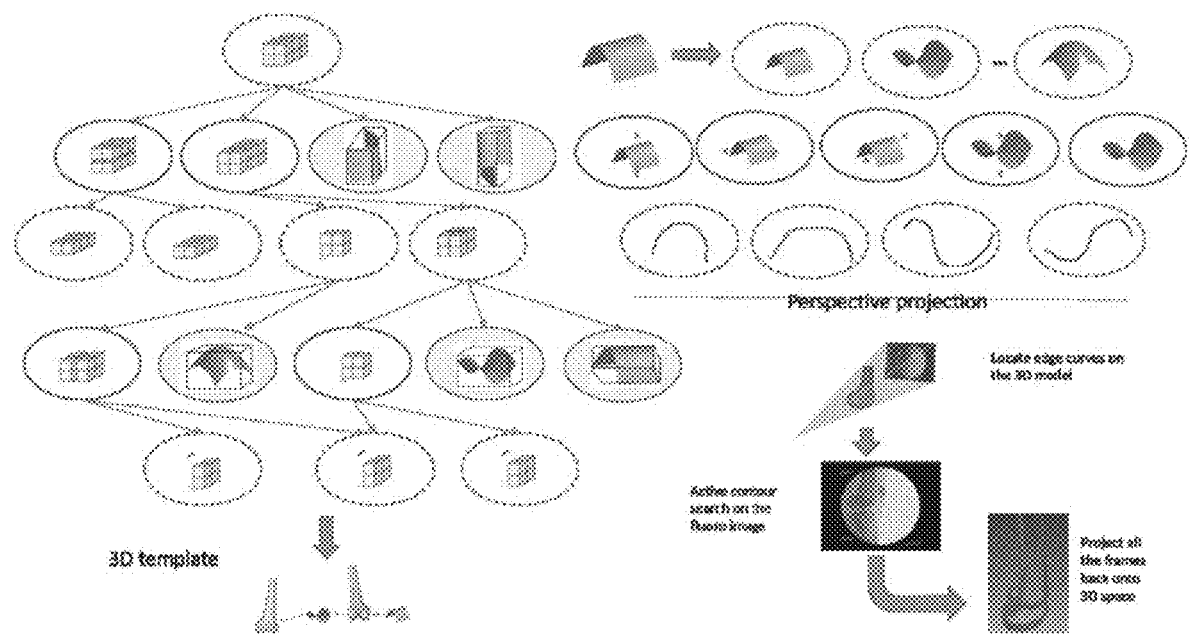
FIG. 66 is a diagram depicting how the geometry space is first decomposed by extracting volumes of interest (VOI) as volumes where part templates may exist.

As shown in FIG. 66, the volume of interest (VoI) is determined by detection. The shape of a generic model is learned from different known poses by optimizing information gain. Then, templates are projected onto 2D image planes as active contours, which deform in image planes. The leaves of the appearance "And-or tree" are projected onto 2D image planes as active contours. At part level, templates can perform in-plane translation, rotation, which is called 3D deformation. Projected active curves are also allowed to deform in 2D. Both 2D and 3D deformation are guided by maximizing the information gain. By projecting the deformed active curves back to the object plane, the 3D model is reconstructed.

Figure 67:
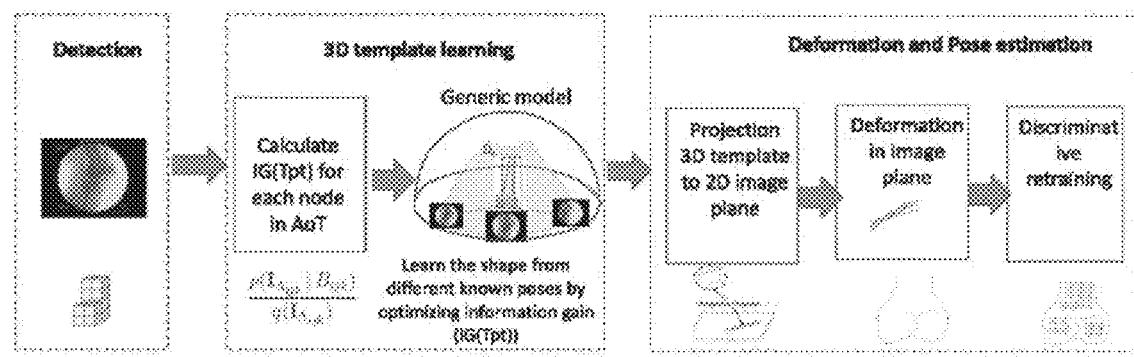
FIG. 67 is a diagram depicting how the volume of interest (VoI) is determined by detection.
Figure 68:
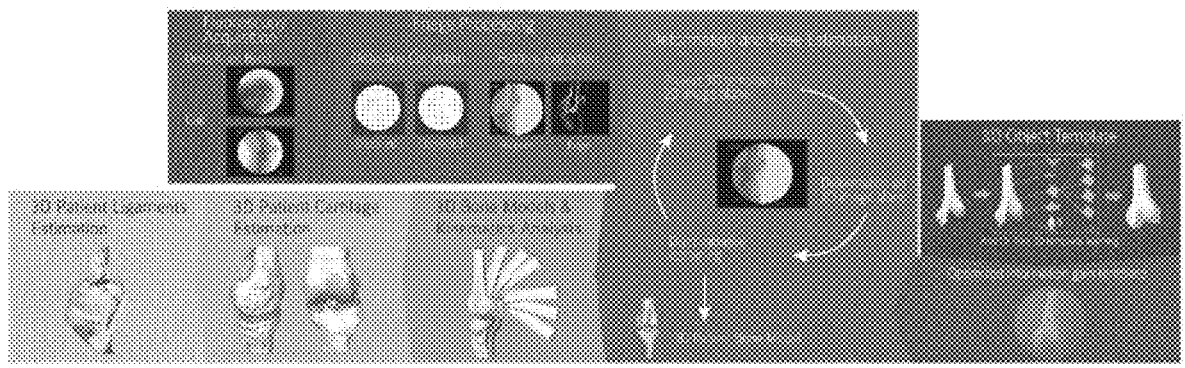
FIG. 68 is a diagram depicting one alternative to using statistical shape deformation is to identify features on the image directly and use the so-called And-Or Tree for shape identification and deformation.
Figure 69:
FIG. 69 is a series of computer generated illustrations decomposing femoral anatomy into primitive shapes.
Figure 69:
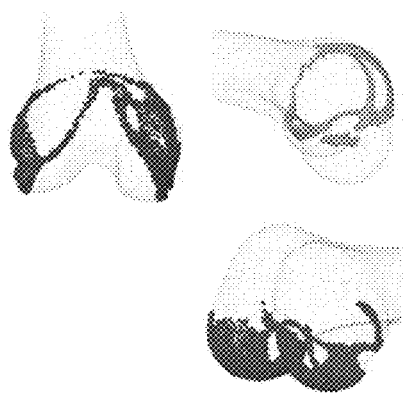

As depicted in FIGS. 67-69, one alternative to using statistical shape deformation is to identify features on the image directly and use the so-called "And-Or Tree" for shape identification and deformation (see Hu, Wenze, and Song-Chun Zhu. "Learning 3d object templates by quantizing geometry and appearance spaces." IEEE transactions on pattern analysis and machine intelligence 37.6 (2015): 1190-1205, the disclosure of which is incorporated herein by reference. In the foregoing publication, the shape parameters for the bone anatomies are dictated by the structure of the AoT and the identification of those structures in the fluoroscopy frames.

It is worth mentioning that for the knee, it is required that, at minimum, the knee portion of the joint be created (distal femur and proximal tibia). However, the same approach could be applied to any joint.

Referring back to FIG. 53, the bone and soft tissue reconstruction substep 22 includes predicting soft tissues and normal anatomy using the dynamic images obtained in substep 21. As part of standard implant design, or patient specific implants and instruments, one relies on static CT or MRI to extract morphology of the joint. However, morphology is usually altered by disease or deformity. In the case of osteoarthritis of the knee, the cartilage may be lost and osteophytes present change the morphology of the knee. Using static CT and MRI may not describe the joint's ligament condition accurately. For example, collapse of the medial compartments in the knee in addition to the presence of osteophytes growth change the Medial Collateral Ligament (MCL) and Lateral Collateral Ligament (LCL) dynamic behavior. Given these large changes on soft tissue and bone, extraction of bone contours becomes difficult, inaccurate, and sometimes impossible. In this situation, statistical atlases of specific population may be used to predict the original deformed bone shape in addition to accurately predict ligament locations and then dynamically extract design parameters and curvature for this specific patient. Rather than rely on static images to generate patient specific implants and instruments, the instant exemplary embodiment uses static images in addition to kinematic data (dynamic data) to generate implants and instruments that are optimized both for replicating patient anatomy and kinematics. Prior art patient specific implants and instruments are, at best, optimized only for replicating patient anatomy, but ignore kinematics or fail to use kinematics as an element of the ultimate shape of the orthopedic implant.

Figure 70:
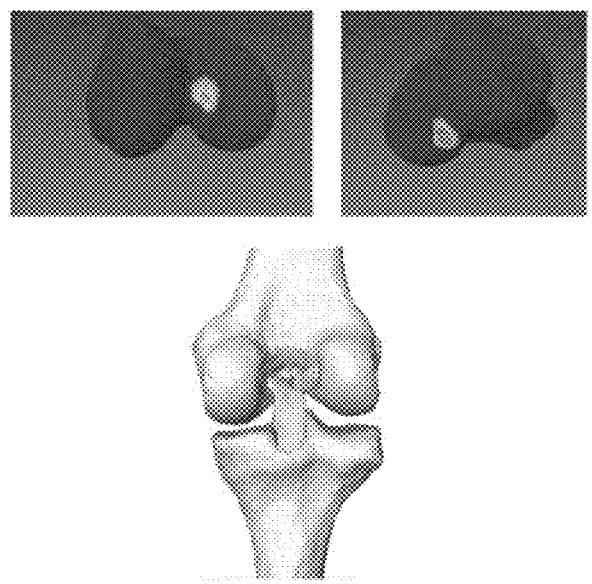
FIG. 70 is a bone model showing ligament locations having been extracted from imaging data.

Turning to FIG. 70, as part of reconstructing the soft tissue associated with the virtual bone model, ligament locations are extracted from imaging data. In particular, the surface models of the bone and ligaments are reconstructed from MRI. The bone models are added to a statistical atlas and each vertex is flagged as either belonging to the attachment site or not based on distance to the ligament surface model. Performing this step for multiple subjects allows for creation of a probability map for each ligament attachment site (shown in a top row for femoral attachment sites of ACL and PCL in FIG. 70). In the map, each bone atlas vertex is assigned a probability of belonging to the attachment site.

Figure 71:
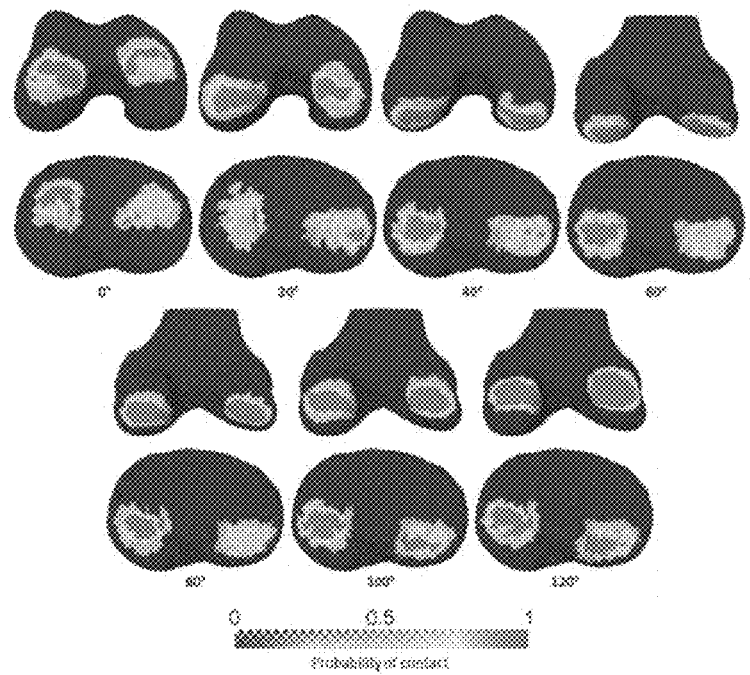
FIG. 71 is a diagram depicting contact maps of the tibia and femur for a deep knee bend.

Referencing FIG. 71, as further part of the bone and soft tissue reconstruction substep 22, contact maps for the femur and tibia are created during deep knee bend. For a single subject, both femur and tibia are assigned vertex correspondence to the respective bone atlases. The pose of the femur relative to the tibia is updated at each flexion angle. At each pose, the vertices of the femur and tibia belonging to the contact regions are determined based on proximity to the articulating bone. Performing this analysis across multiple subjects allows for creation of a probability map on each bone, at each flexion angle, of contact regions.

Figure 72:
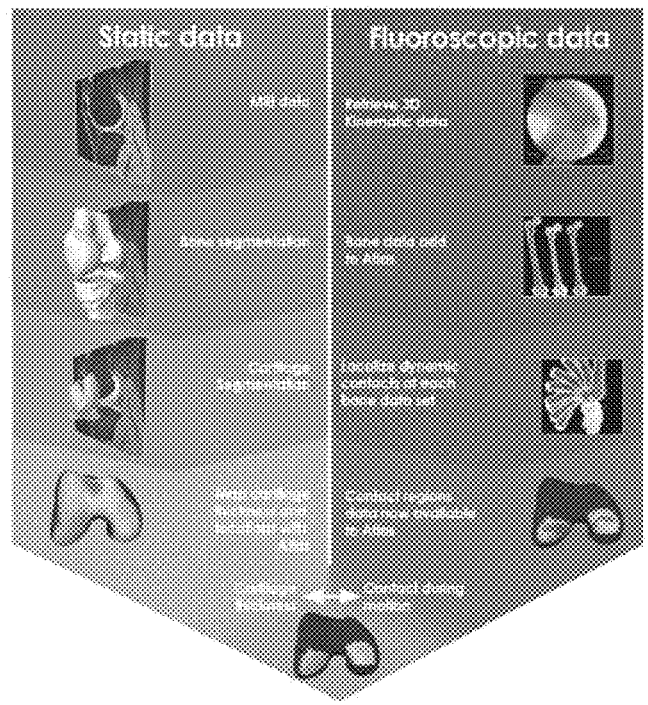
FIG. 72 is a diagram depicting how static data and fluoroscopic data are utilized to couple kinematics and morphology.

FIG. 72 depicts inputs and outputs associated with an exemplary method for determining cartilage thickness within contact regions during a deep knee bend (such as recorded during the dynamic imaging substep 21 in FIG. 53). This method is used to map the contact regions, determine true patient specific thickness, and tie this information back into the previously created normal statistical atlas. In this fashion, kinematics is coupled to morphology.

Figure 73:
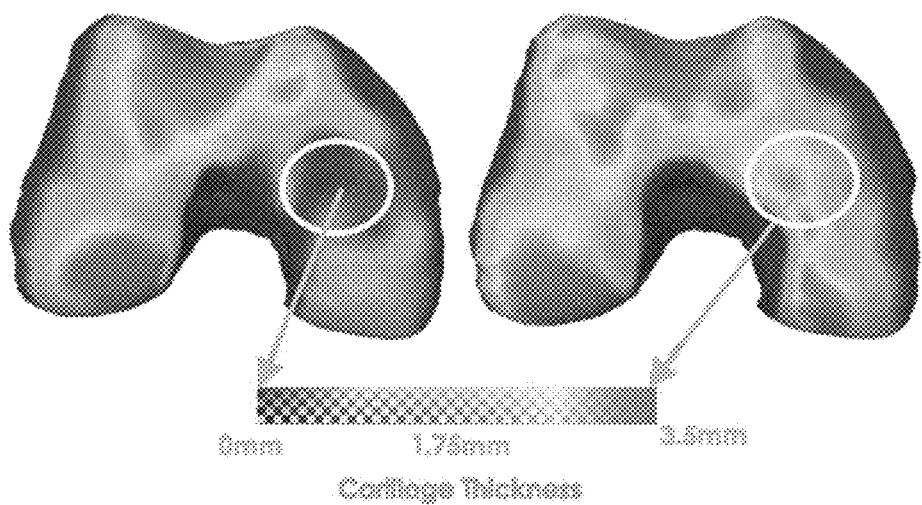
FIG. 73 is a map of two distal femurs showing relative cartilage thicknesses as part of dynamic image taking.

FIG. 73 depicts a patient specific cartilage map (obtained from kinematic analysis, substep 21 in FIG. 53) showing severe cartilage loss in the medial compartment. Creating a patient specific implant with only this information would lead to poor implant functionality. Instead, the instant embodiment uses statistical methods to estimate of the morphology before a deformity is created, thereby allowing for true patient specific (prior to pathology) curvature extraction. And this estimated morphology leads to greater implant functionality.

Figure 74:
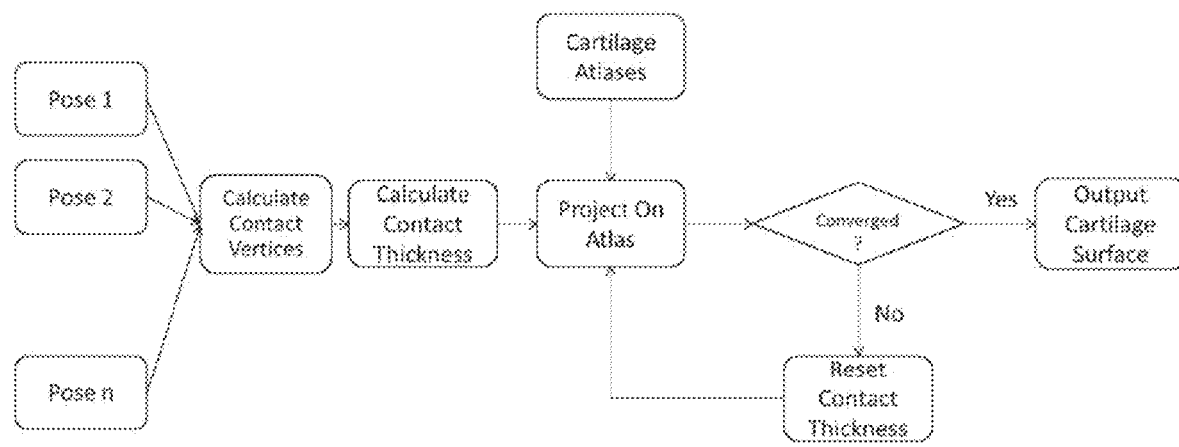
FIG. 74 is a flow diagram for estimating cartilage thickness from dynamic data.

Referencing FIG. 74, a flow diagram is depicted for estimating cartilage thickness from dynamic data in accordance with the instant disclosure. Given multiple poses of articulating surfaces—the knee, for example—the contact at each pose is determined. Contact is primarily determined using a small percentage of the closest points between each model. For each contact point, the distance between the point and the articulating model is determined. The cartilage thickness can then be estimated as X % from model 1, Y % of model 2 so that the sum of the two thickness values equals the total distance between the surfaces. Calculating the thickness at each contact vertex at each pose provides a set of "known" thicknesses that are to be kept constant during the estimation procedure. This set can be considered convex set 1 in the projection on convex sets (POCS) algorithm. Convex set 2 is the cartilage atlases, which previously calculated from a priori datasets—these cartilage atlases can include normal anatomy, specific pathological cohorts (varus, valgus in case of knee) or a combination thereof. As per the POCS algorithm, convex set 1 is projected onto convex set 2, the result of which is projected back on convex set 1—this is repeated until the result converges. In the described algorithm, the projection on the atlas updates all vertices belonging to the cartilage. If the result has not converged, the vertices belonging to the cartilage are set to convex set 1 (the "known" thicknesses) and projected back onto the atlas until convergence is reached. When converged, the surface of the cartilage on each articulating bone model is exported. This routine allows accurate estimation of cartilage by making use of dynamic data to capture full contact information.

Figure 75:
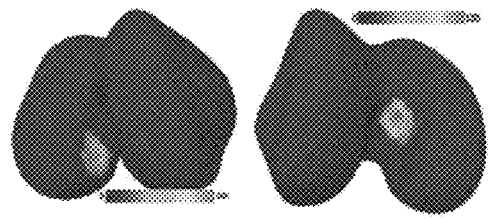
FIG. 75 is a ligament loci probability map for a distal femur and a proximal tibia.
Figure 75:
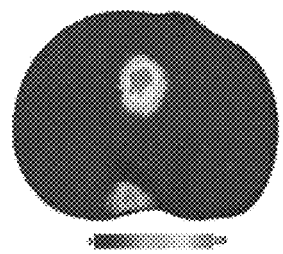

Referring back to FIG. 53, upon reconstruction of bone shape, location of the ligaments are predicted using ligament shape atlas, shape atlas has the ability to capture the loci of soft tissue across population, along with the probability of each point being a ligament loci as shown in FIG. 74. The calculated ligament insertion points are then used to calculate the ligament length envelope during kinematic activities as shown in FIG. 75.

The basis for cartilage estimation is a statistical model that contains a mean cartilage template and uses information from the segmented femur and tibia models to locally deform the mean cartilage template. The mean cartilage template is the mean cartilage thickness calculated from a database of manually segmented cartilage models. Each thickness value has an index associated with it, corresponding to a point on the bone atlas, which is used to localize that value. When adding the mean template to a new bone model, each point on the bone is warped outward along the normal direction a distance corresponding to the mean thickness from the template at that location. The mean cartilage template is adjusted only when the femoral and tibial cartilage overlap. In this case the cartilage thickness is reduced globally by a small factor and at areas of overlap by a larger factor. This process iterates until there are no areas of overlap.

Figure 76:
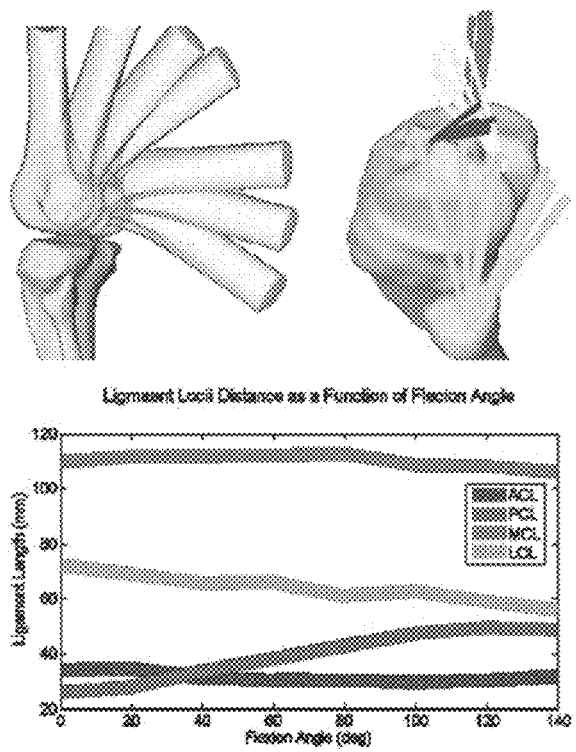
FIG. 76 is a pair of models and a chart utilized to predict the location of ligament loci and changes in ligament length envelope.
Figure 77:
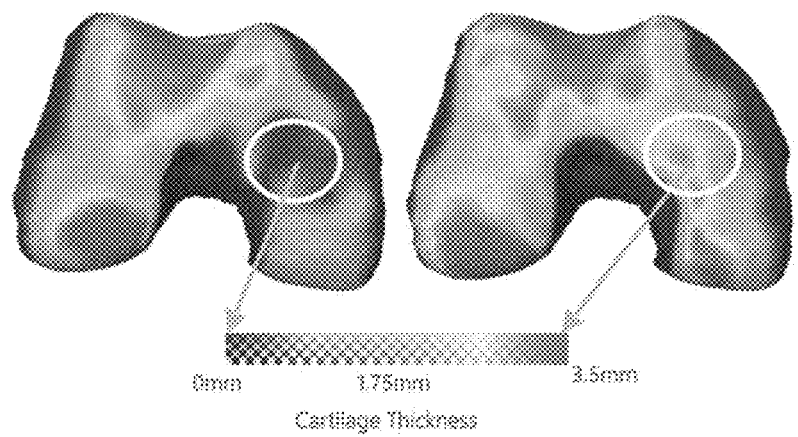
FIG. 77 is a pair of distal femur models mapping the amount of predicted cartilage loss.
Figure 78:
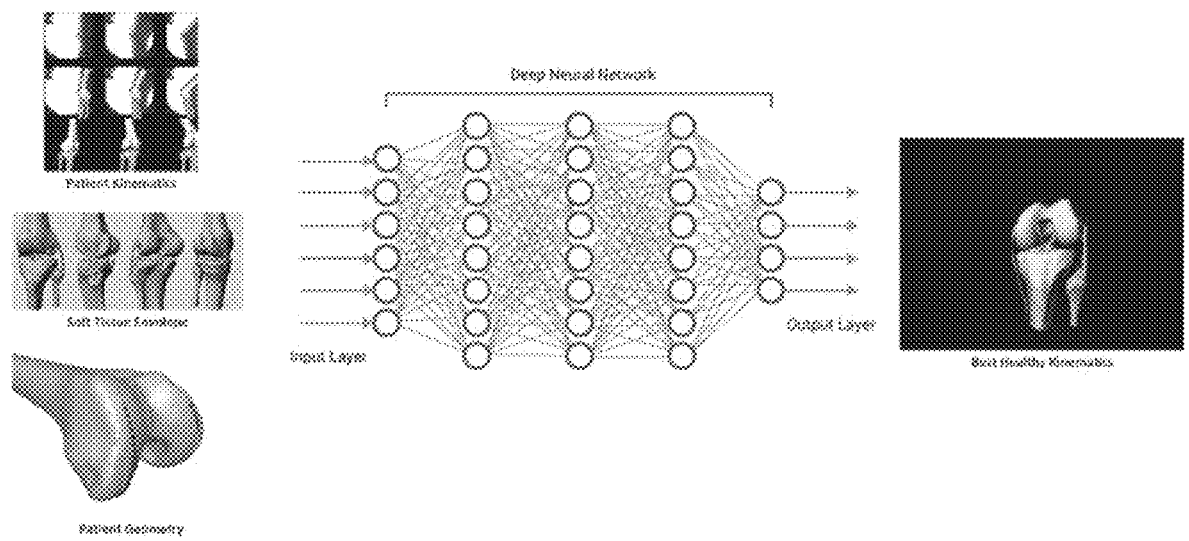
FIG. 78 is a process flow diagram for creating and using kinematic training networks for identifying kinematic patterns.
Figure 79:
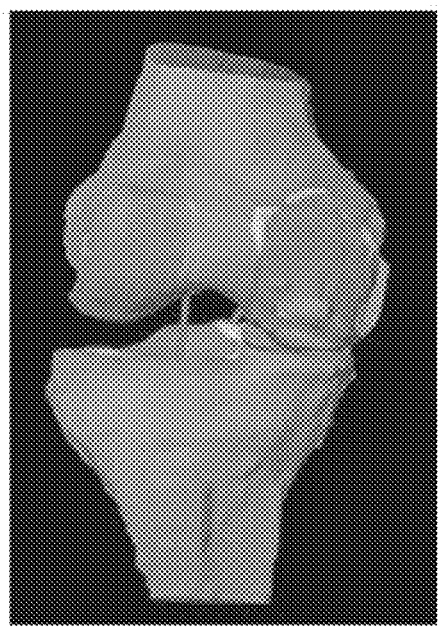
FIG. 79 is a knee joint bone model showing a collapse of a medial side.

Using estimated cartilage maps along with measured joint deformity, the location of cartilage loss is determined and amount of cartilage loss can be estimated by projecting the patient cartilage on the normal cartilage model, as shown in FIG. 76. By correcting for the amount of cartilage loss, the joint can be put back into its normal alignment. This change in joint alignment directly affects ligament length and laxity. For example, loss of cartilage on the medial side will lead to laxity in the medial collateral ligament and increased tension in lateral collateral ligament as shown in FIG. 78. Restoring normal joint alignment change in ligament length can be calculated (see FIG. 79). Using soft tissue and morphology information the closest kinematic model from the normal kinematic database is selected.

By way of example, determining normal healthy kinematics may be through the use of deep neural network, where the network may be trained by motions performed by healthy joints. The deep neural network may take pathological motion input and determines the optimal healthy kinematics (see FIG. 73).

Figure 80:
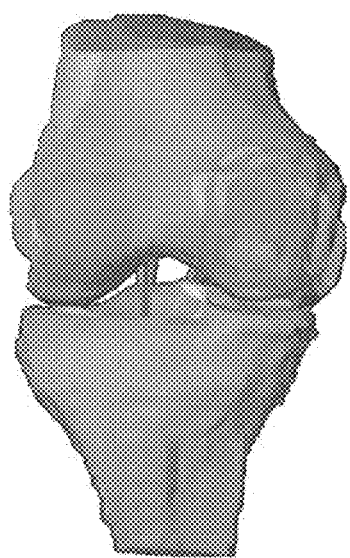
FIG. 80 is a knee joint bone model showing estimation of normal joint alignment and change in ligament length.

Referring to FIG. 80, a flow chart is provided depicting an exemplary process for calculating patient specific ligament stiffness as part of the normal kinematics prediction element in FIG. 53. In exemplary form, discussed with respect to an ankle arthroplasty procedure, a series of passive kinematic motion aspects are recorded that include, without limitation, motion, speed of motion, acceleration of motion, and ligament length during the motion. These aspects are used as inputs for a passive motion model, which also receives inputs concerning ligament stiffness and mass of the tissues moved during motion. Using these inputs, the passive motion model predicts the force necessary to move the tissues. And this predicted force is compared against a measured force to analyze whether the ligament stiffness values should be adjusted so that the predicted force equals the measured force. In circumstances where the predicted and measured forces are not equal or very closely similar, the ligament stiffness values and/or the mass inputs are optimized and updated to allow subsequent predicted force calculations. This process may be repeated until the predicted and measured forces fall within acceptable tolerances of one another. A more detailed discussion of how the measured force is generated is discussed below.

A force actuator attachment may be connected at the distal end of the tibia near the ankle, thereby forcing the tibia to extend passively from approximately 90 degree flexion with respect to the femur to full extension while under fluoroscopic surveillance. The actuator force may be constant during the whole activity. During this activity, care should be taken so as the femur is not moved but only the tibia extends. Multiple passive trials may be conducted by varying the amount of constant force in each trial. Care should be taken so that the activity is conducted at slow speeds so that the patient does not feel a sense of imbalance causing him to tighten his muscles to prevent the activity. The kinematics of the tibia and the patella with respect to the femur may be calculated from the fluoroscopic images using 2D to 3D reconstruction. An inverse dynamic model of the lower extremity should be created to simulate the passive leg raise activity. This model should incorporate the femur, tibia, and patella and the major ligaments (patellar ligament, ACL, PCL, MCL, LCL) spanning the joint. The reconstructed bone models, along with the loci location of the soft tissues, may be used to setup the geometry of the model. The model may start off with initial stiffness values of the ligaments, mass, inertia of the components based on previous published values and the amount of force required to perform the activity may be predicted. Finally, the patient specific values of these parameters may be calculated by using an optimization algorithm that matches the predicted force to the actuator force recorded during the multiple trials.

Returning to FIG. 53, the output from the normal kinematics prediction substep 23 may be utilized as inputs for the patient specific dynamic creation step 24 and the instrument creation step 2-4.

Figure 81:
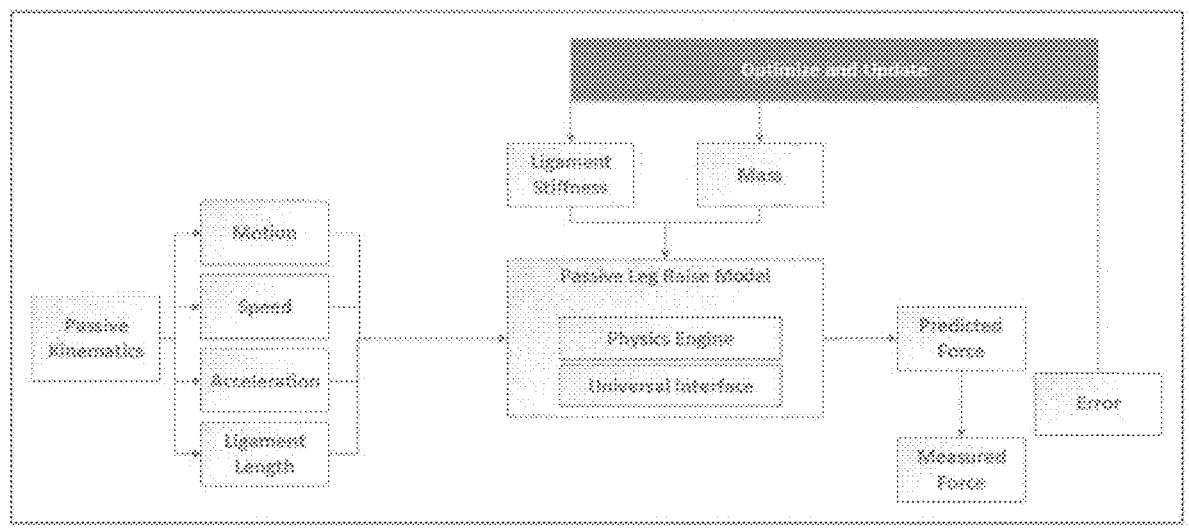
FIG. 81 is a flow chart of an exemplary process to calculate patient specific ligament stiffness.

As depicted in FIG. 81, a flow diagram is provided setting forth an exemplary process for creating patient specific dynamic implants. There may be at least three potential paths to generate patient specific dynamic implants, all of which may rely on a database containing healthy joints' data including profiles, kinematics, and soft tissues properties. One of the paths may utilize active motion performed by the patient in combination with the healthy kinematic database to estimate the patient specific healthy kinematic profile 23-B, and utilize soft tissue properties 23-C. The outputs from substeps 23-B and 23-C may be input to an implant shape optimization substep 28 to optimize the implant kinematics and shape. Another path may utilize the estimate of the patient specific healthy kinematic profile as described in 23-B and input it to a deep neuron network model in substep 27, where the implant shape may be created directly.

Figure 82:
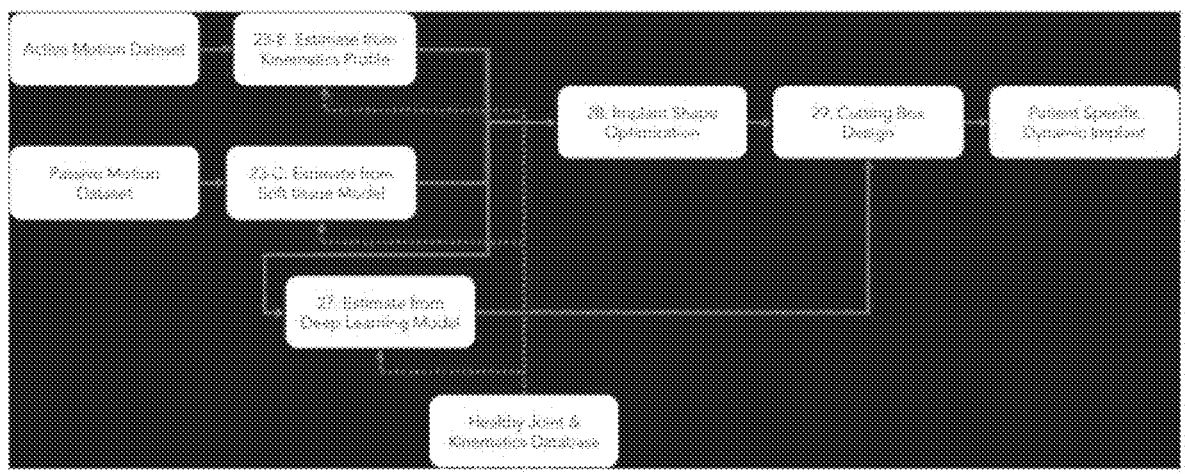
FIG. 82 is a process flow diagram of an overview of the process for creating a patient specific dynamic implant.

FIG. 82 depicts and exemplary process flow for creation of patient specific implants using estimation from either healthy kinematic profiles or ligament stiffnesses.

Using the stiffness values of the ligaments obtained previously as explained with respect to FIG. 81 and based on feedback from the surgeon, a decision is made regarding what kind of implant the patient needs to have. For example, in the context of a knee replacement, the decision may be whether the patient will receive a cruciate retaining, posterior stabilized, BCS, or BCR implant. Since manufacturing custom polyethylene bearing components may not always be a cost effective business model, it is proposed to have a wide family of polyethylene geometry templates and corresponding femoral templates to capture statistical shape variations of the normal knee anatomy. There should be a different family for each implant type with different sizes of implants within a family to account for different sized bones corresponding to a particular shape. Because it is impossible to perfectly match the properties of the multiple tissues involved in joint articulation (cartilage, meniscus) and still obtain a reliable component, the shape of the articulating surface should be optimized to constrain motion appropriately while distributing load to optimize component age. Current implant families rely on sagittal and coronal polyethylene curvature to constrain motion (ultra-congruent) by matching the femoral curvature or reduce constraints (unconstrained) by reducing curvature or creating a completely flat articulating surface. The latter is more common in partial joints or when ligaments are retained, as these soft tissues will partially constrain kinematics.

Depending on the situation, the dynamically designed tibia surface can be optimized for contact throughout the range of motion corresponding to a femoral template family. This allows true matching of surface to expected load for added longevity and improved performance. Based on the curvatures of the predicted normal anatomy of the patient, first the implant family, and then the best size of femoral and polyethylene templates within the family, are chosen as the base models. The idea is to have the best model that fits the patient's anatomy and preserves neutral alignment of the patient.

Figure 83:
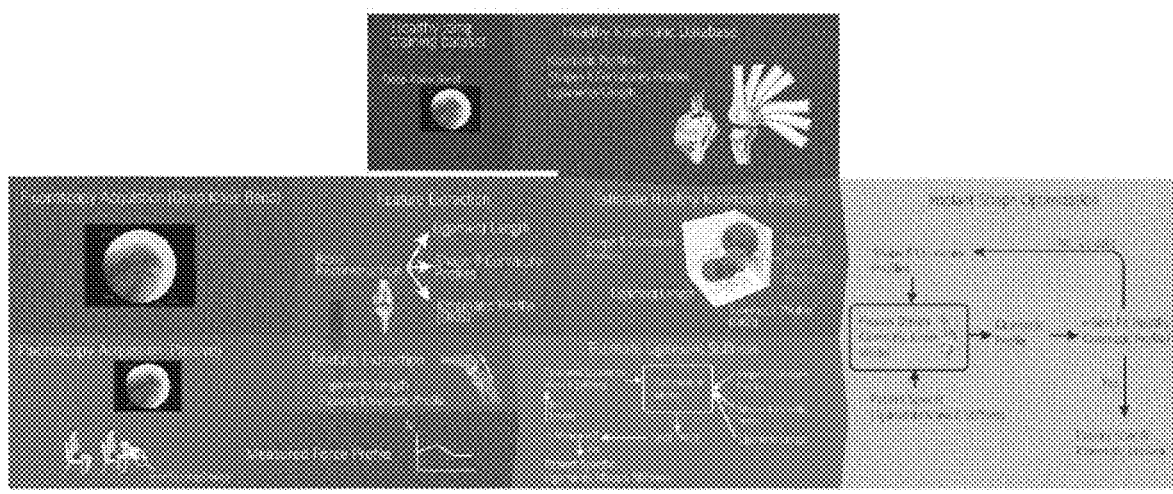
FIG. 83 is a chart illustrating an exemplary process for utilizing estimation from either healthy kinematic profile or ligament stiffness as part of creating a patient specific dynamic implant.

As depicted in FIG. 83, a pair of examples of differing polyethylene sagittal curvatures (femoral curvature on top). On the top left, a less constrained congruent curvature. This design allows more anterior-posterior translation through flexion. On the top right is an ultra-congruent design, which increases contact area while constraining translation due to the curvature more closely mirroring the femoral curvature. Custom designs should be optimized based on static, non-weight bearing image data. The dynamic implant disclosed herein utilizes imaging that allows analysis of weight bearing kinematics, which are used to define the correct curvature based on expected implant load, contact surfaces, and desired post-operative kinematics.

Figure 84:
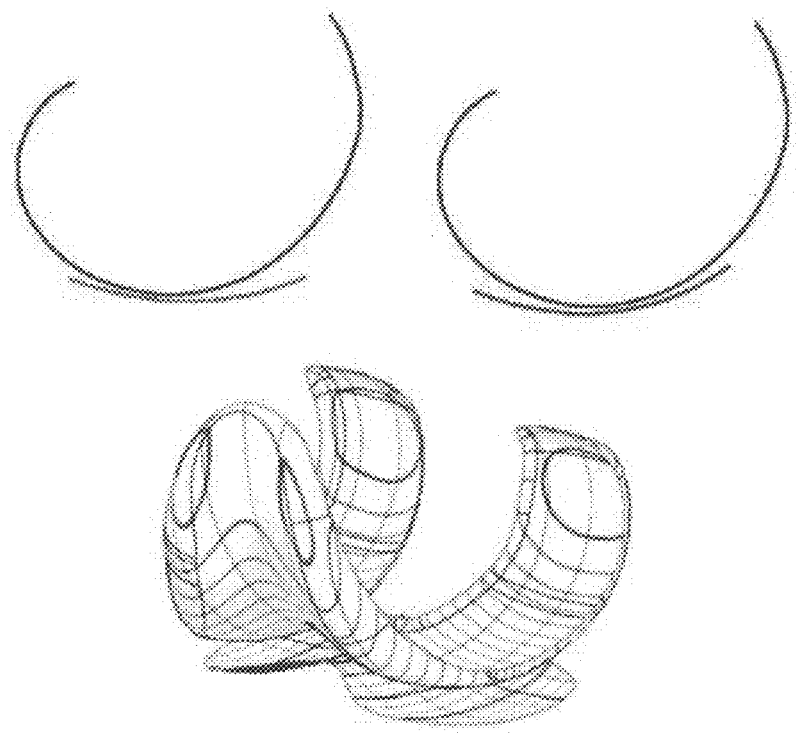
FIG. 84 is a depiction of differing polyethylene sagittal curvatures and a corresponding femoral implant.

Referring to FIGS. 81 and 84, once the kinematics profile and the soft tissue model have been identified, the implant shape optimization substep 28 may include a forward dynamic flexion driven simulation for the lower extremity. Based on the implant type, relevant soft tissues may be retained in the model and the template implants are fit on the bones using natural joint alignment. For this simulation, the femoral flexion with respect to the tibia should be prescribed while the remaining five degrees of freedom (three translations, axial rotation, abduction/adduction) predicted. Based on the normal data as reference, that has previously been identified suitable for the patient, an optimization may be performed to change the sagittal and coronal curvatures of the femoral implant condyles (and cam as applicable) so that the difference between the desired and observed degrees of freedom is minimized. Once the best template models have been optimized for (as a double check the simulation is repeated with two corresponding to lower and higher size implants to generate an optimal femoral profile per polyethylene geometry template), the final design may be chosen based on a weighted combination of the one that gives the best replication of the normal knee geometry and maintains sufficient contact areas with the polyethylene bearing to ensure reduced wear and improved longevity.

Figure 85:
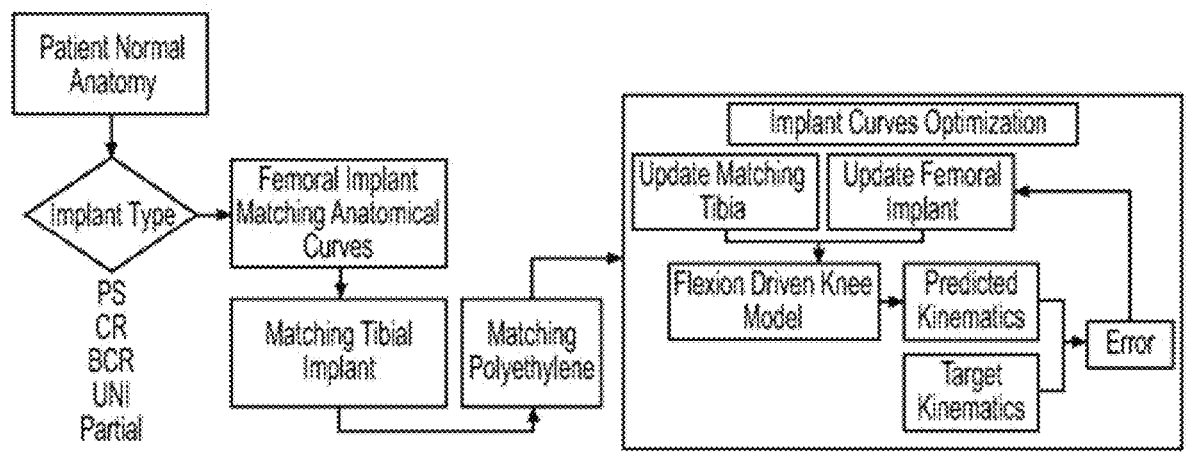
FIG. 85 is a flow chart depicting an exemplary process for implant shape optimization.

Referencing FIG. 85, from Newton's equation of the motion, F=ma (force=mass×acceleration). Therefore, if the acceleration (kinematics) of the related components are known, the force that is driving the motion can be predicted, which is a process known as inverse dynamics. For the passive model, depicted in FIG. 85, the geometry will consist of the femur, tibia and patella bones assumed as rigid bodies with appropriate ligaments (ACL, PCL, MCL, LCL) connecting the femur and tibia and the extensor mechanism (quadriceps and patellar ligament). Since the femur is stationary, the system has 12 degrees of freedom (6 for the tibia and 6 for the patella) allowing one to calculate for 12 outputs. The inputs to the model may consist of the translation and rotational kinematics of the tibia and the patella with respect to the femur, the spring stiffnesses of the ligaments, and assumed inertia parameters. Therefore, the ligaments should be modeled as massless non-linear springs that generate load only when extended and forces in them should be specified as inputs based on the amount of stretch they exhibit. The quadriceps and the patellar ligament may be modeled as a massless system, forces in which may be predicted. Finally a force may be applied at the distal tibia to simulate the actuator force. The outputs from the model may be the prediction of the distal actuator force and contact forces at the femorotibial and patellofemoral joints. The joint contact forces are of no interest in this case and the input kinematics per trial are also measured. Therefore, a multivariate optimization may be performed to identify the best spring stiffness parameter and inertia values that predict the actuator force most accurately.

Figure 86:
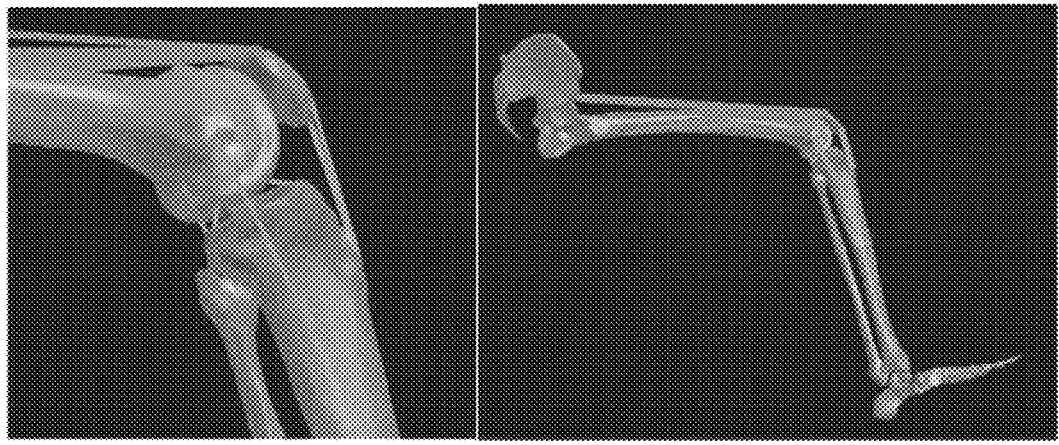
FIG. 86 is a computer generated model of a passive knee model.

Referring to FIG. 86, one embodiment of the kinematic driven model is the flexion driven model. This model is a forward dynamics model and is opposite in nature to the passive model discussed immediately above. The idea is to predict accelerations once force and inertia values are known. The geometry may consist of the femur, femoral implant, tibia, tibia implant and patella bones assumed as rigid bodies with appropriate ligaments (ACL, PCL, MCL, LCL) connecting the femur and tibia and the extensor mechanism (quadriceps and patellar ligament). The implant components may be assumed to be rigidly fixed to the bones. This model is boundary condition driven. The point on the distal end of the tibia corresponding to the ankle joint should be held fixed and the head of the femoral head should be pushed down with constant velocity to simulate knee flexion. The system generates 18 equations (6 for tibia, 6 for femur and 6 for patella). Given an interest in femorotibial kinematics only, 5 degrees of freedom (axial rotation, 3 translations, and abduction/adduction) of the femur with respect to the tibia may be solved for. All other equations should be suitably constrained. The kinematics of the femur may be affected by the contacting geometry of the implant condyles. The sagittal and coronal curvature of the femoral and implant should be updated using a multivariate optimization algorithm that tries to match the observed kinematics with the target kinematics of the femur with respect to the tibia.

Figure 87:
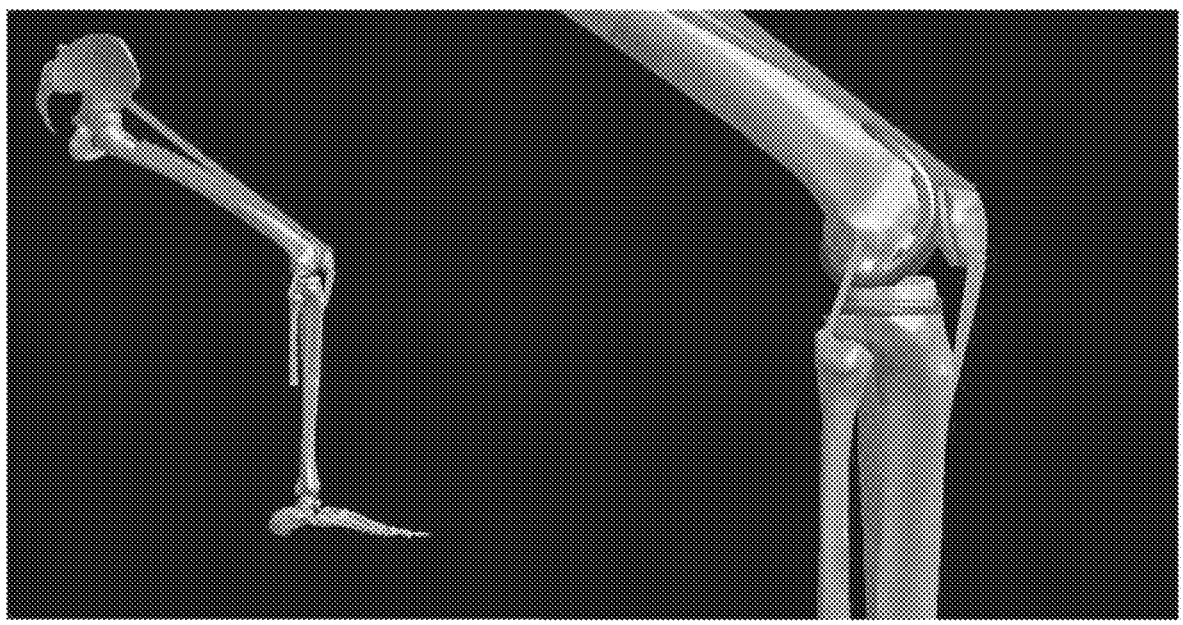
FIG. 87 is a computer generated model of a flexion driven model with customizable ligament model to match implants being created.
Figure 88:
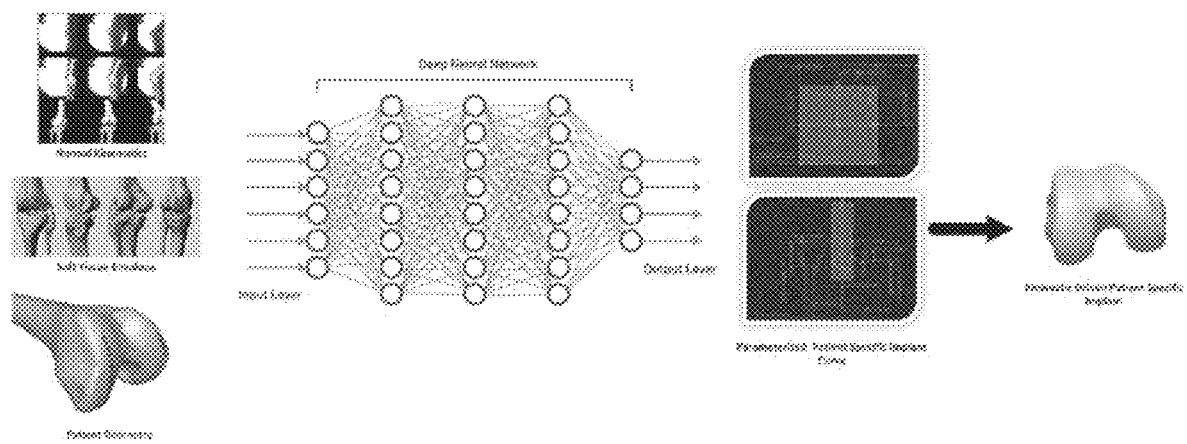
FIG. 88 is a flow diagram of an exemplary process of creating and using networks for defining optimal CAD parameters for a restorative patient implant from kinematic data.
Figure 89:
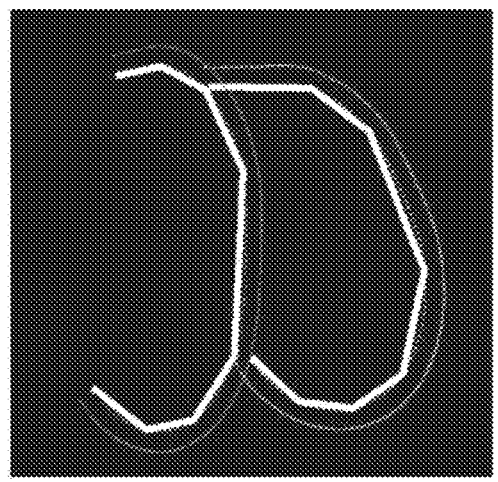
FIG. 89 is a representation of approximation of offsetted implant J Curve with line segments as an initial guess for a patient optimized cutting box.
Figure 90:
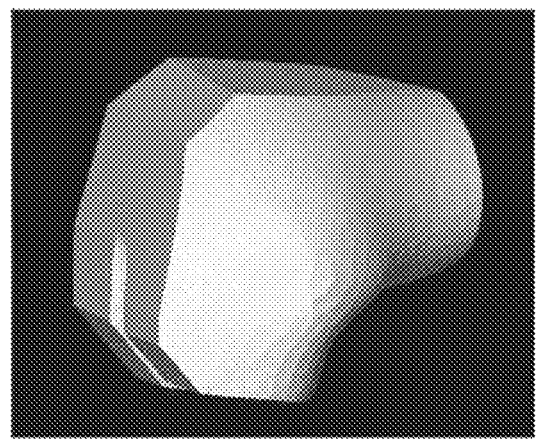
FIG. 90 is a computer generated resected femur bone model using a patient optimized cutting box.
Figure 91:
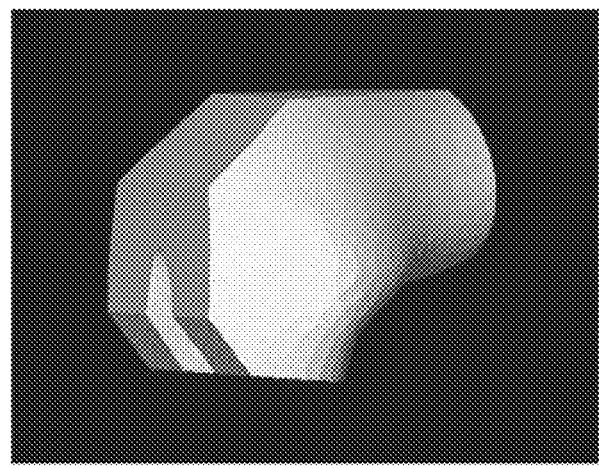
FIG. 91 is a computer generated resected femur bone model having been recut using a traditional revision implant cutting box.
Figure 92:
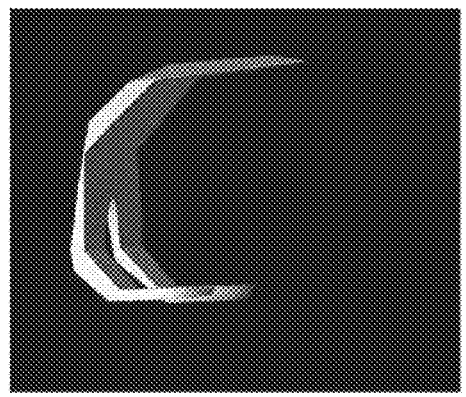
FIG. 92 is a computer generated bone model showing the amount of additional bone resected using a traditional revision implant cutting box versus using a patient optimized cutting box.

Turning to FIGS. 81 and 87, a more detailed discussion of the deep learning model substep 27 follows. In exemplary form, one may utilize a process of creating and using networks for defining optimal CAD parameters for a restorative patient implant from kinematic data. The inputs to the deep neural network may include patient geometry, soft tissue data, and kinematic data, all of which are processed by the network to determine best shape of the patient specific implant that restores patient anatomy and aids in achieving optimal post-operative kinematics. Those skilled in the art are familiar with neural networks and, accordingly, a detailed discussion of neural networks has been omitted in furtherance of brevity.

Returning to FIG. 53, post implant creation, the process may move on to the manufacturing substep 25. The manufacturing processing for the patient specific dynamic knee may encompass generation or creation of patient specific implants, patient specific instruments, and patient specific resection cutting guides. The optimized knee implant may converse bone loss during the surgery by creating patient specific resection planes where the information may be passed to a smart cutting guide (as previously described) to be executed during the surgery.

Referencing FIGS. 89-92, the geometry of the femoral implant cutting box is designed to minimize the amount of resected bone (or the amount of recut bone in case of revision) based on the patient anatomy and the implant curvature. Inputs for the implant cutting box design may include the implant J-curves, patient anatomy, and the cutting box of the closest traditional implant. Due to the unique resection planes, which are different from conventional implant resection planes, a smart cutting guide (as discussed previously) may be used to optimize and execute the resection in the operating room (see FIGS. 34-37).

Returning to FIG. 53, the outputs from the manufacturing substep 25 provide inputs for the intra-operative navigation substep 5-10.

Figure 93:
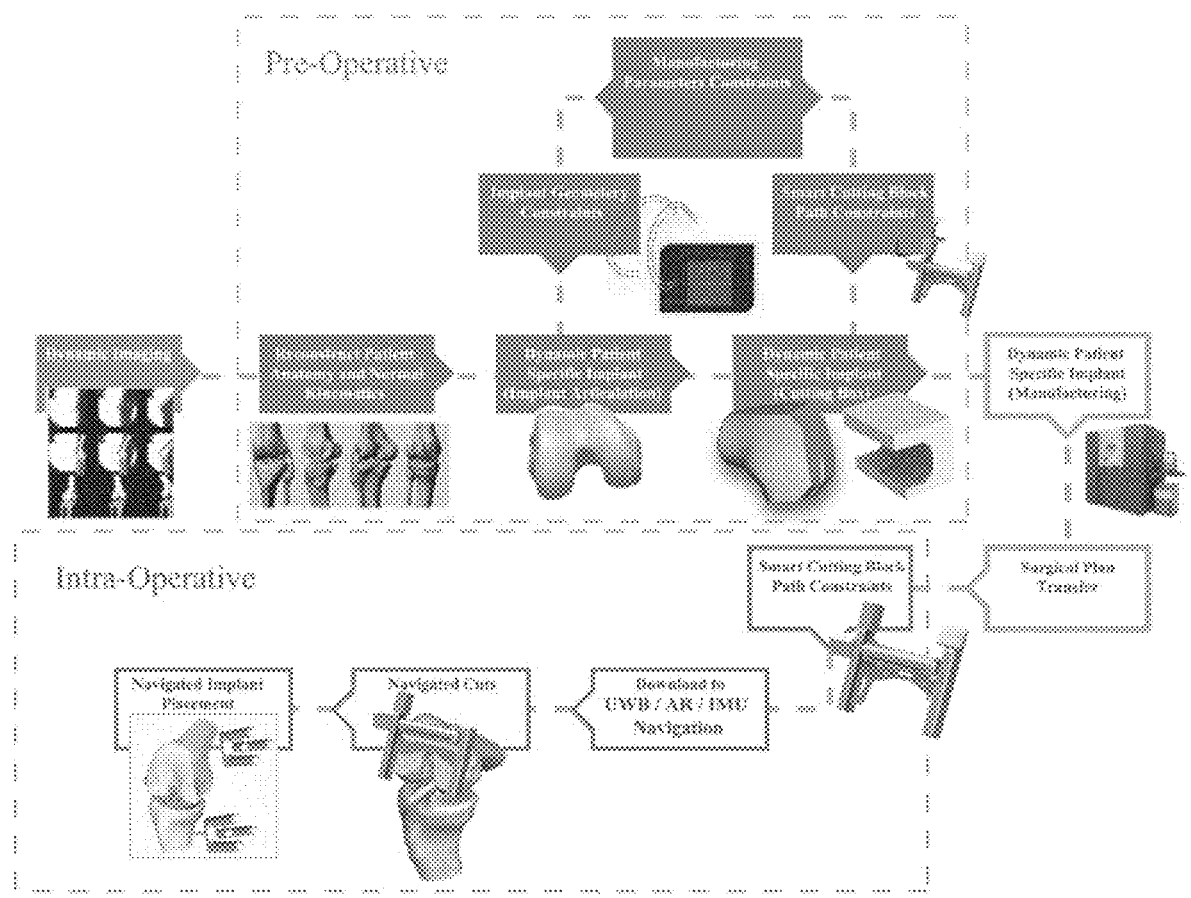
FIG. 93 is a flow chart outlining the overarching concept of dynamic implant creation and execution of the surgical plan intraoperatively using the smart cutting guide.

As shown in FIG. 93, an exemplary flow chart outlines the overarching concept of dynamic implant creation and execution of the surgical plan intraoperatively using the smart cutting guide. Pre-operatively dynamic imaging data is collected and used to create patient anatomy as outlined earlier in FIG. 56 (Patient anatomy creation). Anatomical and kinematic data are then used for creating dynamic implant articulation as outlined earlier in FIGS. 81-84 (Dynamic Implant Creation). This creation is bounded by manufacturing and approved implant geometry constraints. Creation of a patient specific cutting box as outlined in FIGS. 88-91 (patient specific cutting box creation). The design of this patient specific cutting box more readily allows one to execute the planned surgical cuts intraoperatively using the smart cutting block discussed previously. The cutting box design may be bounded by manufacturing constraints of the box design such as, without limitation, the thickness of the implant and the constraints driven by the motion of the smart cutting block. A design patient specific implant is then prepared for manufacturing, where a pre-operative surgical plan (locations and orientations of the cuts) may used to configure the smart cutting guide. Implant placement information and the pre-operative surgical plan may be stored or sent to the intraoperative navigation system, where the smart cutting guide may be used to facilitate the cuts and the surgical navigation and guidance system is used for implant placement navigation and range of motion verification.

Returning to FIG. 53, after the intra-operative navigation substep 5-10 and the surgical procedure has been completed, the exemplary AR system may be utilized post-operatively to evaluate the patient's condition.

Figure 94:
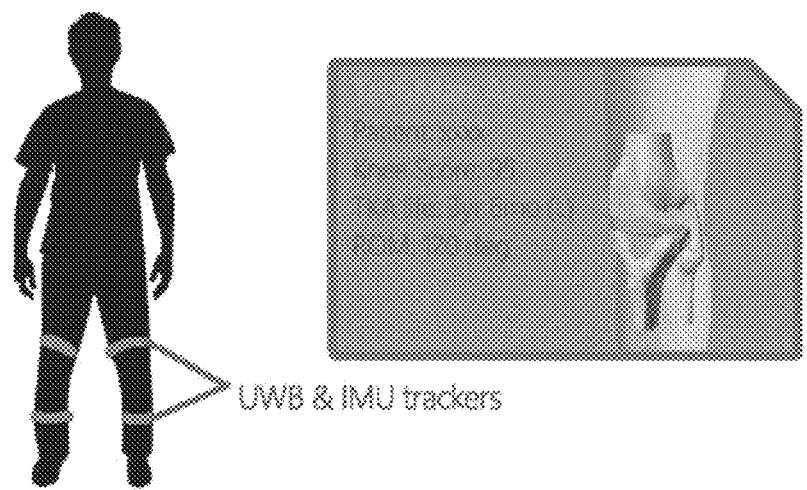
FIG. 94 is an illustration of using UWB and IMU trackers as part of a post operative evaluation.

As depicted in FIG. 94, the foregoing exemplary AR system may be utilized post-operatively in combination with UWB and/or IMU tracking system to examine, monitor, and evaluate the patient's recovery process through quantitative metrics such as range of motion, contact area of the implants, and analyzing muscle activation during motion. In exemplary form, a set of UWB and IMU trackers may be placed on both sides of the joint for post-operative evaluation. The AR system overlays the implant positions based on the patient movement, analyzes the muscle activation, and provides assessment to the physician in real time. In this exemplary application, the UWB and/or IMU tracking system(s) may be implemented as a strap-on device or body-fitting garment.

Figure 95:
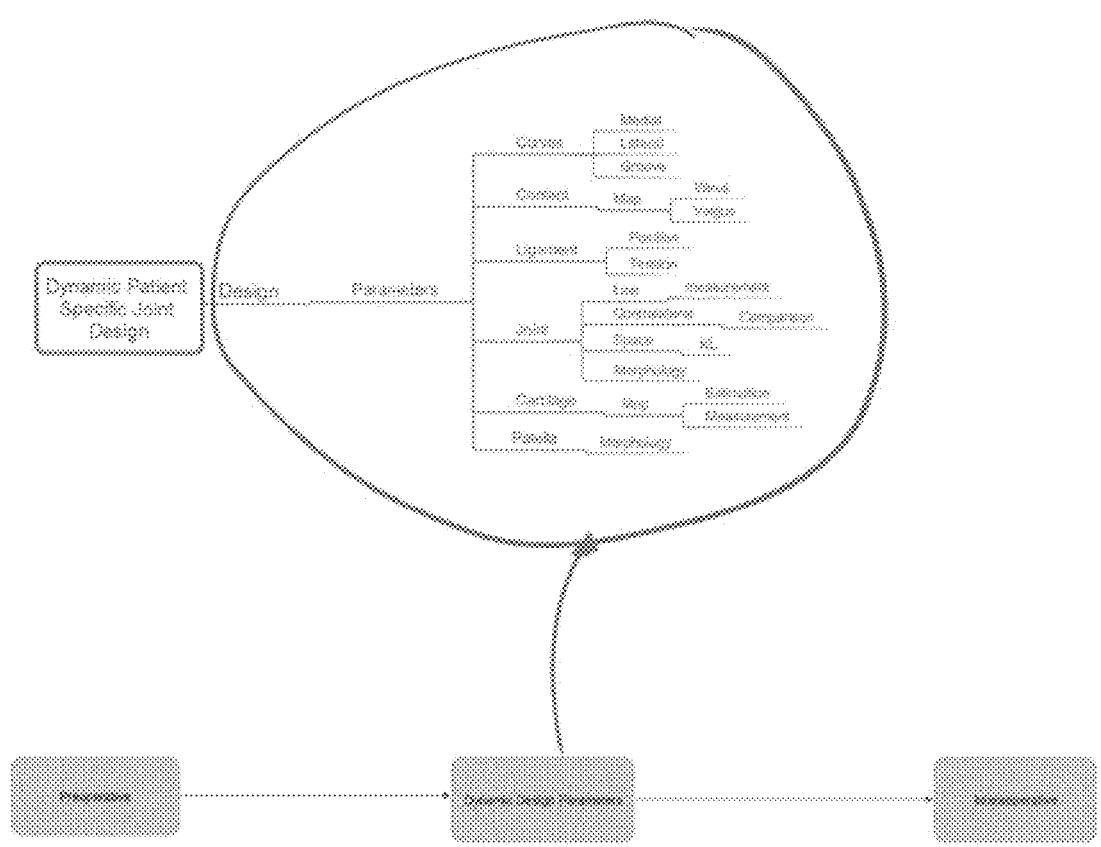
FIG. 95 is an exemplary diagram listing patient specific implants and parameters used to create implants.

Turning to FIG. 95, an exemplary list of patient specific implants and parameters used to create implants are depicted. Of particular relevance to the knee are the curvatures of the medial lateral condyle of the femur, which differ from one another, the patellar groove of the femur (and the curvature of the patellar button) and the lateral lip of the tibia plateau, which is critical for true patient specific femortibial tracking. Coupling these osseous geometries with patient specific soft tissues and pathology restoration techniques discussed previously, a true patient specific knee implant and procedure can be created. In the portion of the flow chart at the bottom, the steps are outlined for preoperative imaging and joint reconstruction, which is used to drive the creation of the implant parameters. From these parameters an implant and plan are created and implemented into the operating room.

Figure 96:
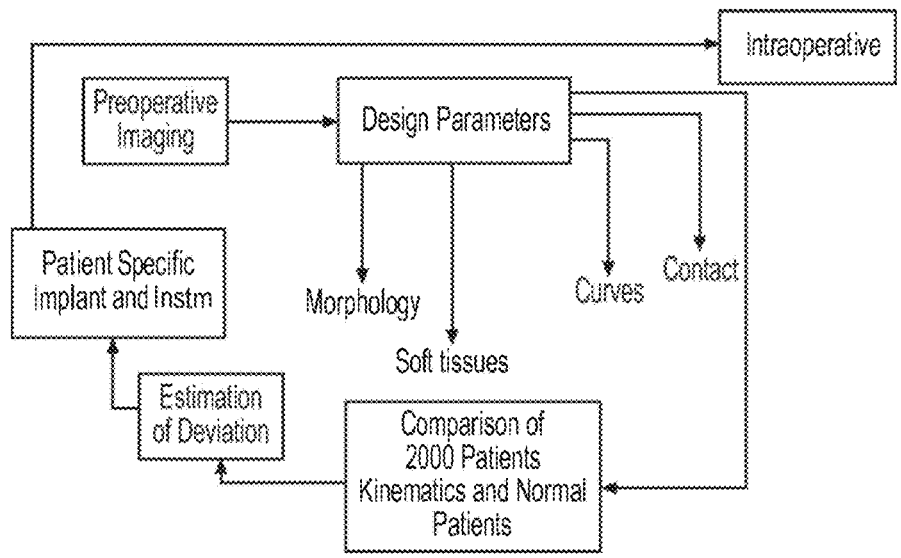
FIG. 96 is an exemplary overview of a process for creating patient specific implants from dynamic data.

Turning to FIG. 96, an overview of an exemplary process for creating patient specific implants from dynamic data is depicted. Preoperative imaging is used to extract patient specific design parameters, which are then compared against a database containing kinematic analysis of normal and implanted patients. This comparison allows for creation of estimates of correction of dynamic data and derivation of restored anatomical curvature as part of the dynamic implant process discussed previously.

Figure 97:
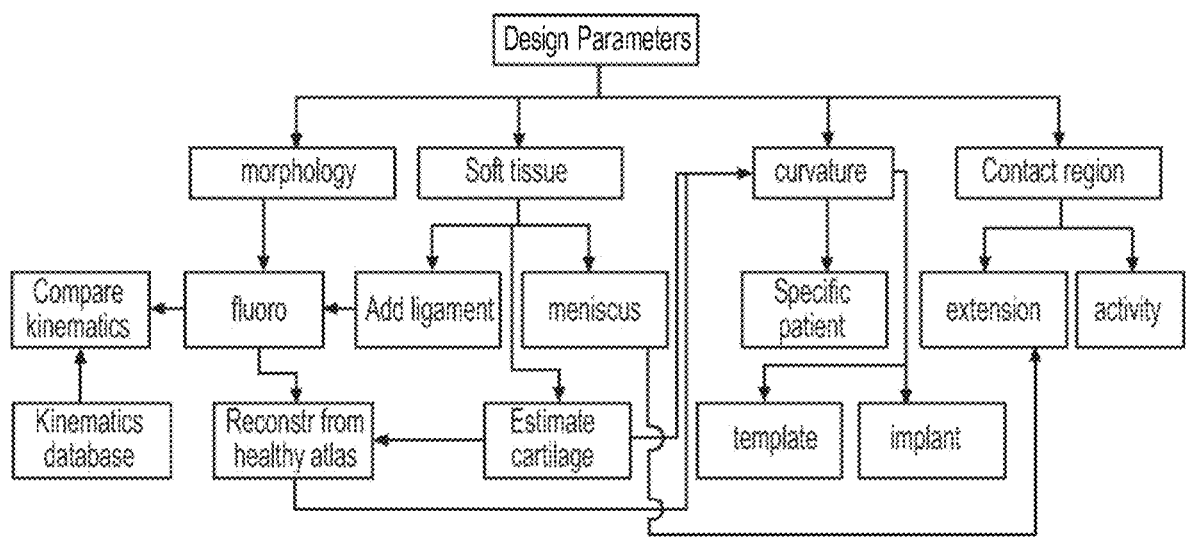
FIG. 97 is a flow diagram indicating information flow for extraction of design parameters from dynamic data and statistical atlases.

Referencing FIG. 97, an exemplary information flow is depicted for extraction of design parameters (such as curvature) from dynamic data and statistical atlases in accordance with the dynamic implant process discussed previously.

Figure 98:
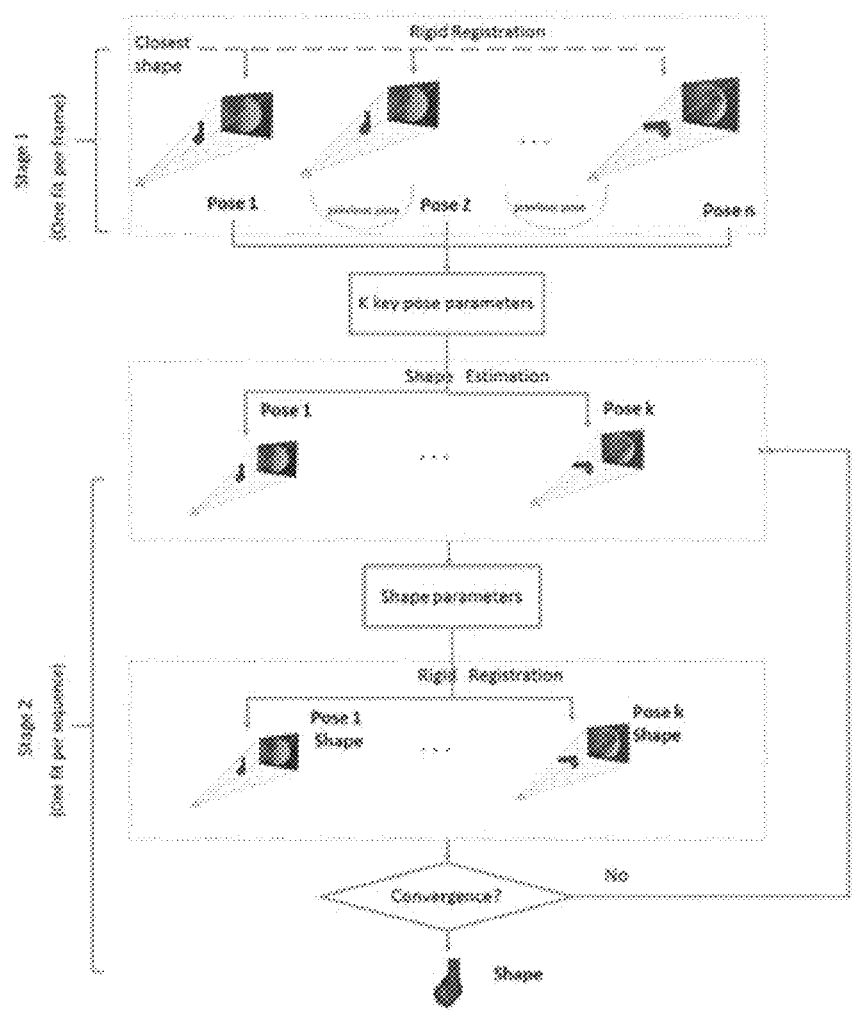
FIG. 98 is a flow diagram depicting reconstruction of a joint from dynamic data.

Referring to FIG. 98, a flow diagram for an exemplary process for construction of a joint implant from dynamic data is depicted. Here a patient specific shape is constructed from analysis of single-plane digital fluoroscopy images. This patient specific data can be fed back into the dynamic data to extract patient specific contact and soft tissue envelopes for implant creation from a single image capture in accordance with the dynamic implant process discussed previously.

Figure 99:
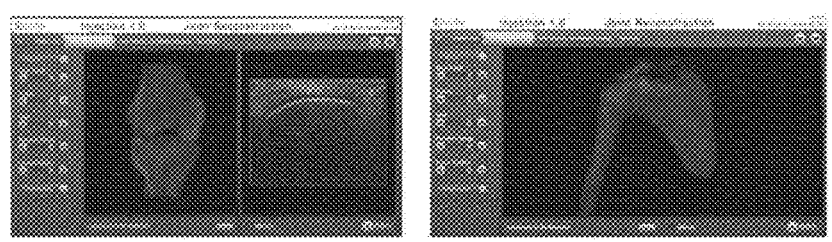
FIG. 99 are screenshots from a software package representing examples of dynamic joint reconstruction.

Turning to FIG. 99, another example of dynamic joint reconstruction is depicted. Here 3D bone information can be captured from ultrasound images (RF Data, B-Mode images or IQ data). Pictured are reconstruction for the knee or shoulder. Coupling the imaging device with trackers on the patient provides the ability to reconstruct more of the anatomy as well as capture dynamic information needed for creating the patient specific kinematics and soft tissue envelopes used for the described implant design method capture in accordance with the dynamic implant process discussed previously.

Figure 100:
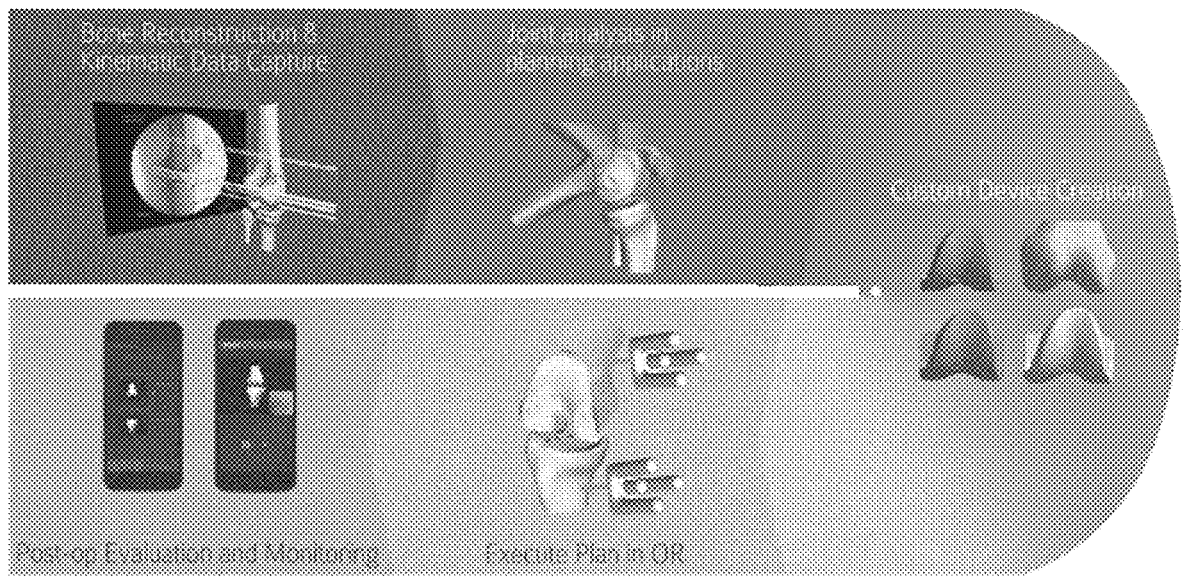
FIG. 100 is a process flow diagram of an exemplary process of utilizing dynamic data across the episode of surgical care to create patient-specific implants and instruments, place the implant and monitor performance post-operatively.

Moving to FIG. 100, an exemplary process is laid out for utilizing dynamic data across the episode of surgical care to create patient-specific implants and instruments, place the implant, and monitor performance post-operatively. The process begins with a kinematic assessment using fluoroscopic or other dynamic imaging modality (as opposed to traditional, static imaging), which is uploaded to a processing CPU to reconstruct motion and anatomical structures from the imaging data. The kinematics and anatomical structures are used as inputs to a prediction model for determining optimal reconstructive shape and normal kinematics. The output shape parameters are used to construct the dynamically created patient specific implant and associated instruments. The implants and instruments are manufactured and coupled with the surgical plan and smart instrumentation in the operating room to achieve precise placement. Finally, to monitor performance, post-operative data, such as kinematics and range of motion, along with patient reported outcomes, is collected through any number of sensors, including IMU, UWB or combinations thereof. This data can then be utilized in a feedback loop with the predictive engine to optimize future patient implant parameters. In such a way, data from the entire episode of care can be utilized to drive implant and instrument design.

Figure 101:
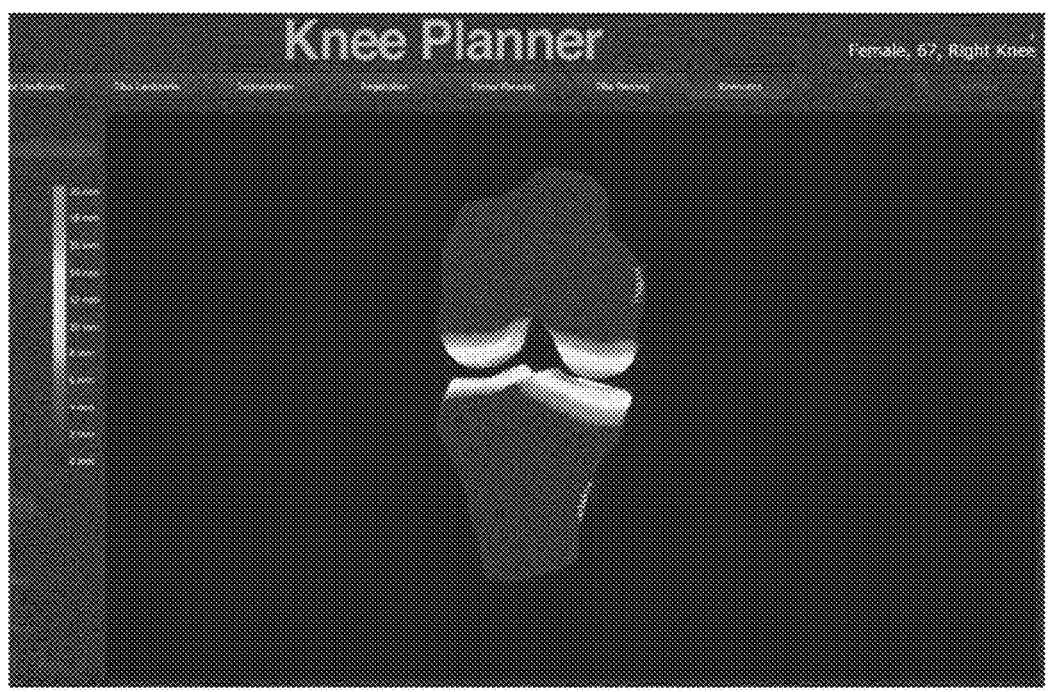
FIG. 101 is a screen shot from a knee planning software application that includes kinematic data as captured by the dynamic imaging process and allows information to be created regarding the soft tissue envelope throughout the range of motion to help improve ligament balancing when developing the surgical plan, as opposed to adjusting in the operating room.

FIG. 101 depicts an exemplary screen shot from a knee planning software application that includes kinematic data as captured by the dynamic imaging process and allows information to be created regarding the soft tissue envelope throughout the range of motion to help improve ligament balancing when developing the surgical plan, as opposed to adjusting in the operating room.

Figure 102:
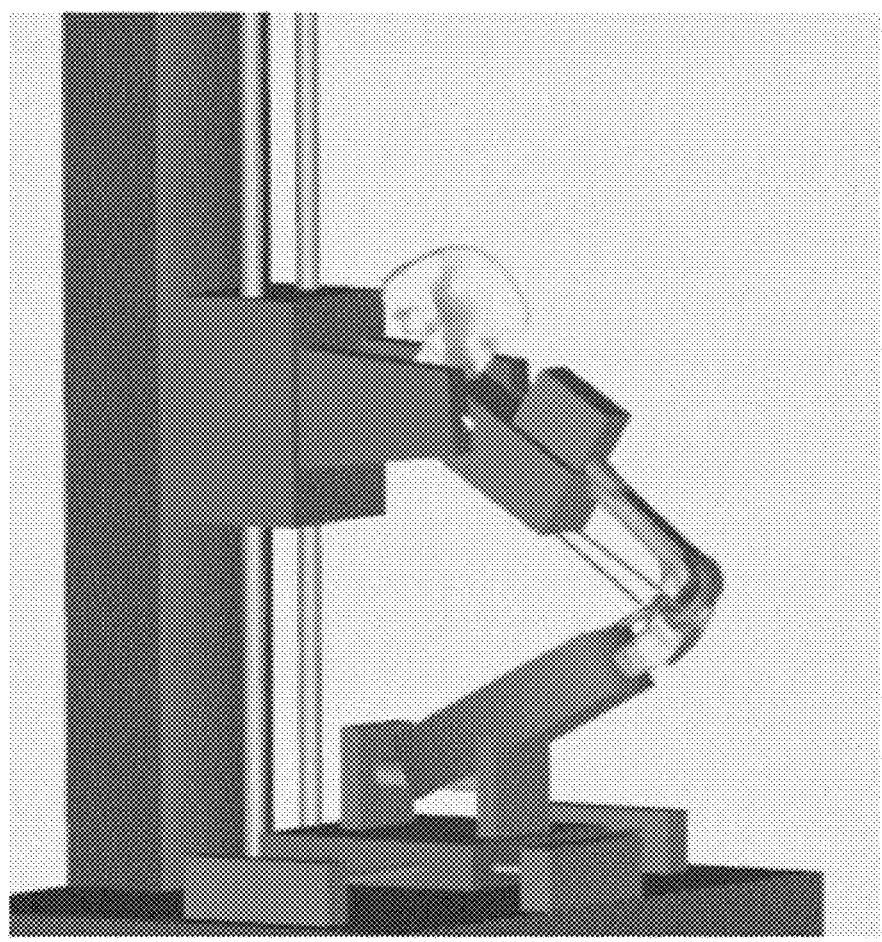
FIG. 102 is a depiction of a flexion driven kinematic knee model.
Figure 103:
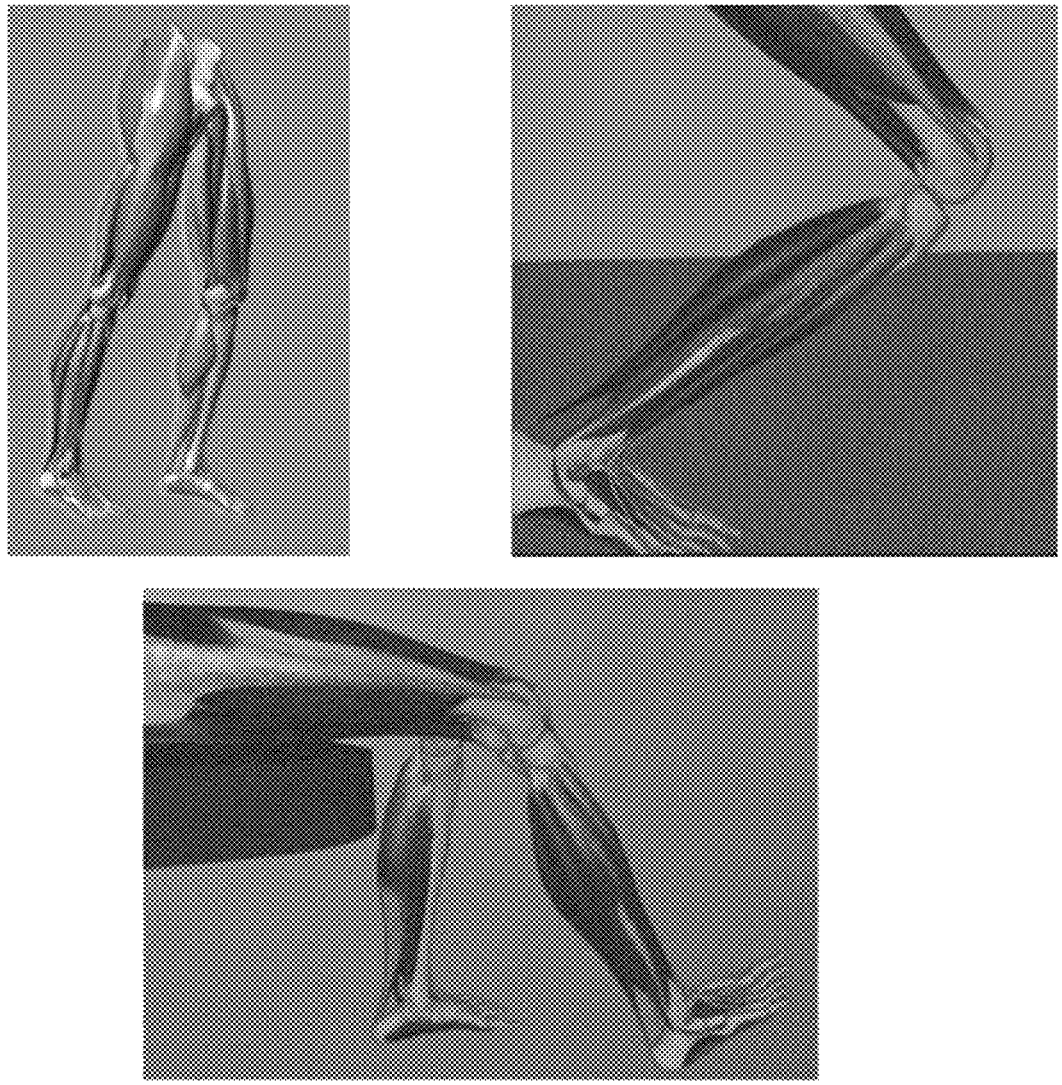
FIG. 103 comprises a series of simulation models for analyzing patient motion and dynamics for input into and output of dynamic implant design process.

Referencing FIGS. 102 and 103, another simulation step may be performed to model the deep knee bend and results stored for comparison with the original data that was observed for the patient during the pre-operative scenario discussed previously that include weight-bearing and non-weight bearing activities that can be captured with the pre-operative fluoro and used to drive simulated post-operative performance. Based on the simulation, the femoral shape may be further optimized so as to ensure the implant has sufficient contact areas with the polyethylene bearing to ensure reduced wear and improved longevity. This model can be established using the patient kinematics, soft tissue attachments, proposed implant designs and anatomical structures as input. The output should be optimized based on the input to achieve estimated implanted kinematics and dynamics, including implant loading, throughout flexion. If an achieved result is not acceptable due to laxity or improper loading, the shape, or more specifically the curvature parameters, may be iteratively optimized until desired results are achieved. In such a way, the implant shape parameters for femur, tibia or patella can be optimized based on multiple patient activities.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of preparing a joint for a joint replacement implant, the method comprising:
   fixing a first bone tracker to a first bone, the first bone tracker providing data associated with at least one of a position of the first bone and an orientation of the first bone from a first bone tracker inertial measurement unit;
   registering the first tracker to the first bone;
   fixing a second bone tracker to a second bone, the second bone tracker providing data associated with at least one of a position of the second bone and an orientation of the second bone from a second bone tracker inertial measurement unit;
   registering the second bone tracker to the second bone;
   attaching a first cutting guide to at least one of the first bone and the second bone;
   cutting one of the first bone and second bone using the first cutting guide;
   attaching a second cutting guide to at least one of the first bone and the second bone; and
   cutting the other of the first bone and the second bone using the second cutting guide;
   wherein the first bone and the second bone are associated with a joint;
   wherein attaching the first cutting guide comprises attaching the first cutting guide to the first bone;
   wherein cutting the one of the first bone and the second bone using the first cutting guide comprises cutting the second bone;
   wherein attaching the second cutting guide comprises attaching the second cutting guide to the first bone; and
   wherein cutting the other of the first bone and the second bone using the second cutting guide comprises cutting the first bone.

2. The method of claim 1, wherein registering the first bone tracker to the first bone comprises palpating a surface of the first bone with a surface tracker, the surface tracker being configured to provide data associated with at least one of a position of the surface of the first bone and an orientation of the surface of the first bone, the surface tracker comprising a surface tracker inertial measurement unit.

3. The method of claim 1, wherein registering the first bone tracker to the first bone comprises registering a plurality of first bone surface points to a first bone virtual surface model.

4. The method of claim 3, further comprising creating the first bone virtual surface model using pre-operative imaging.

5. The method of claim 1, wherein registering the first tracker to the first bone comprises
   placing a first bone mapper at a predetermined location relative to the first bone; and
   providing data associated with at least one of a position of the first bone mapper and an orientation of the first bone mapper from a first bone mapper tracker, the first bone mapper tracker comprising a first bone mapper inertial measurement unit.

6. The method of claim 5, wherein the first bone mapper comprises a first bone mapper surface configured to match a portion of the first bone so that a position and an orientation of the first bone mapper tracker relative to the first bone is known.

7. The method of claim 1,
   wherein the first bone tracker inertial measurement unit comprises at least one of an accelerometer, a gyroscope, and a magnetometer; and
   wherein providing data associated with the at least one of the position of the first bone and the orientation of the first bone from the first bone tracker inertial measurement unit comprises providing data associated with the at least one of the position of the first bone and the orientation of the first bone from the at least one of the accelerometer, the gyroscope, and the magnetometer.

8. The method of claim 1, further comprising imaging the joint including at least a portion of the first bone and at least a portion of the second bone.

9. The method of claim 1, further comprising tracking at least one of a position and an orientation of the first cutting guide using a first cutting guide tracker, the first cutting guide tracker comprising an inertial measurement unit.

10. The method of claim 9, further comprising comparing the at least one of the position and the orientation of the first cutting guide to a patient-specific pre-operative surgical plan developed from pre-operative patient imaging.

11. The method of claim 1, further comprising, before cutting the one of the first bone and the second bone, manipulating at least one of the first bone and the second bone into a desired position.

12. The method of claim 11, further comprising, after manipulating the at least one of the first bone and the second bone into the desired position, locking the joint by installing at least one bone pin.

13. The method of claim 1, further comprising tracking at least one of a position and an orientation of the second cutting guide using a second cutting guide tracker, the second cutting guide tracker comprising an inertial measurement unit.

14. The method of claim 13, further comprising comparing the at least one of the position and the orientation of the second cutting guide to a patient-specific pre-operative surgical plan developed from pre-operative patient imaging.

15. The method of claim 1, further comprising, before attaching the second cutting guide, removing the first cutting guide.

16. The method of claim 1,
wherein the first bone comprises a tibia;
wherein the second bone comprises a talus; and
wherein the joint comprises an ankle.

17. The method of claim 16, further comprising
securing a talus cutting guide on the tibia;
locking the ankle by installing at least one locking bone pin into the talus through the talus cutting guide;
resecting the talus using the talus cutting guide;
securing a tibia cutting guide to the tibia; and
resecting the tibia using the tibia cutting guide.

18. The method of claim 17,
wherein securing the talus cutting guide to the tibia comprises securing the talus cutting guide to the tibia using at least one mounting bone pin; and
wherein securing the tibia cutting guide to the tibia comprises securing the tibia cutting guide to the tibia using the at least one mounting bone pin.

19. A kit for preparing an ankle joint for a joint replacement implant, the kit comprising:
a first tibia inertial measurement unit (IMU) adapter for mounting to a tibia;
a second talus IMU adapter for mounting to a talus;
a first tibia cutting guide, that includes an IMU, for mounting to the tibia; and
a first talus cutting guide, that includes an IMU, for mounting to the tibia and the talus.

20. The kit of claim 19, wherein the first talus cutting guide includes a slot configured to guide a bone cutting blade during talus resection.

21. The kit of claim 19, wherein the first tibia cutting guide includes a slot configured to guide a bone cutting blade during tibia resection.

22. The kit of claim 19,
wherein the first talus cutting guide is configured to receive at least one bone pin for securing the first talus cutting guide to the tibia; and
wherein the first talus cutting guide is configured to receive at least one bone pin for securing the first talus cutting guide to the talus.

* * * * *